(12) United States Patent
Role et al.

(10) Patent No.: US 6,933,122 B1
(45) Date of Patent: Aug. 23, 2005

(54) A-FORM OF CYTOPLASMIC DOMAIN OF NARIA (CRD-NEUREGULIN) AND USES THEREOF

(75) Inventors: Lorna W. Role, New York, NY (US); David Talmage, New York, NY (US); Jianxin Bao, Riverdale, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/312,596

(22) Filed: May 14, 1999

(51) Int. Cl.[7] ...................... G01N 33/53; G01N 33/543; G01N 33/545; G01N 33/552; G01N 33/566
(52) U.S. Cl. ........................ 435/7.1; 435/7.2; 435/7.92
(58) Field of Search ........................ 435/7.1, 7.2, 7.92

(56) References Cited

U.S. PATENT DOCUMENTS

| | | | |
|---|---|---|---|
| 5,578,482 A | | 11/1996 | Lippman et al. |
| 5,602,096 A | * | 2/1997 | Goodearl et al. |
| 6,284,535 B1 | * | 9/2001 | Role |

OTHER PUBLICATIONS

Rudinger, J. In *Peptide Hormones*, J. A. Parsons, Ed. University Park Press, Baltimore, pp. 1–7, 1976.*
Mahanthappa, N. K. et al., (Aug. 1, 1996) Glial Growth Factor 2, a Soluble Neuregulin, Directly Increases Schwann Cell Motility and Indirectly Promotes Neurite Outgrowth, *J. Neuroscience* 16 (15) :4673–4683, (Exhibit 2).
International Search Report from International Searching Authority for PCT International Application No. PCT/US00/13157, dated Apr. 20, 2001, (Exhibit 3).
Poster for seminar entitled "A role of HEN1 in Neurogenesis and Recent Data on Neuregulin" dated May 20, 1999, (Exhibit 4).
Bao, J. et al. (Oct. 1997) Abstract for Society for Neuroscience Meeting, CNIP: A Novel Interactor Protein Specific for the Cytoplasmic Domain of CRD Neuregulin., (Exhibit 5).
Bao, J. et al. (Oct. 1999) Abstract for Society for Neuroscience Meeting, Novel Functions of the Cytoplasmic Domain of Neuregulin. (Exhibit 6).
Wolpowitz, D. et al. (Nov. 1998) Abstract for Society for Neuroscience Meeting, CRD–NRG In Mouse Peripheral Nervous System Development, (Exhibit 7).
Yang, X, et al. (Feb. 1998) A Cysteine–Rich Isoform of Neuregulin Controls the Level of Expression of Neuronal Nicotinic Receptor Channels During Synaptogenesis, *Neuron*, 20:255–270, (Exhibit 8).
Chu, G.C. et al., (1995) Regulation of the acetylcholine receptor and subunit gene by recombinant ARIA: an in vitro model for transynaptic gene regulation. *Neuron* 14:329–339, (Exhibit 9).

Corfas, G. et al., (1995) Differential expression of ARIA isoforms in the rat brain. *Neuron* 14:103–115 (Exhibit 10).
Falls, D.L. et al., (1993) ARIA, a protein that stimulates acetylcholine receptor synthesis, is a member of the neu ligand family. *Cell* 72:801–815 (Exhibit 11).
Ho, W–H, et al., (1995) Sensory and motor neuron–derived factor. *J. of Biol. Chem.* 270(24) :14523–14532 (Exhibit 12).
Holmes, W.E. et al., (1992) Identification of heregulin, a specific activator of $p185^{erbB2}$. *Science* 256:1205–1210 (Exhibit 13).
Kuo, Y. et al., (1994) Isolation and characterization of chick and human nARIA, a novel member of the ERBB2/HER ligand family which lacks the immunoglobin domain. *Soc. for Neurosc. Abstr.* 20:1095. (Exhibit 14).
Kuo, Y. et al., (1993) Expression of members of the neu (ARIA) ligand family in chick and rat central nervous system. *Soc. for Neurosc. Abstr.* 19:1725 (Exhibit 15).
McGehee, D.S. et al., (1995) Nicotine enhancement of fast excitatory synaptic transmission in CNS by presynaptic receptors. *Science* 269:1692–1696 (Exhibit 16).
Mudge, A.W. et al., (1993) New ligands for neu? *Current Biol.* 3(6) :361–364 (Exhibit 17).
Sivilotti, L. and Colquhon, D. (1995) Acetylcholine receptors: too may channels, too few functions. *Science* 269:1681–1682 (Exhibit 18).
Vartanian, T. et al., (1994) A role for the acetylcholine receptor–inducing protein ARIA in oligodendrocyte development. *PNAS, U.S.A.* 91:11626–11630 (Exhibit 19).
Wen, D. et al., (1992) Neu differentiation factor: a transmembrane glycoprotein containing an EGF Domain and an immunoglobulin homology unit. *Cell* 69:559–572 (Exhibit 20).
Yang, X. et al., (1994) Identification of different ARIA splice variants expressed by chick cns and pns neurons during development. *Soc. for the Neurosc. abstr.* 20:1095 (Exhibit 21).
Wolpowitz, D. et al., Isoform Specific Knockout of Neuregulin–1 gene products: Selective Disruption of Only Cysteine–Rich Domain (CRD) –containing Isoforms, Mouse Genetics Conference, Cold Spring Harbor (1998) (Exhibit 23).

* cited by examiner

*Primary Examiner*—Brenda Brumback
*Assistant Examiner*—Stephen Gucker
(74) *Attorney, Agent, or Firm*—John P. White, Esq.; Cooper & Dunham LLP

(57) ABSTRACT

This invention provides nARIA-based assays for defining whether a subject has or is predisposed to developing a neoplastic disease. This invention further provides a nARIA-based method for maintaining synaptic connections between a neuron and a target cell.

5 Claims, 33 Drawing Sheets

FIGURE 1A

```
   1  CGGATGCTGC TGCTACTGTC ACTTCTGCCG CTGCCGCTGT TGTTACAGAT
  51  TTTGCTTTTG CTCCTTCTAC CGCATGACAA TTGTTTTCCT CGCCTAAGCA
 101  GATACCAGCC TCAGATGCTC AAGGTGAGAG TCTTGCCTTT CGCTCTGGGC
 151  TATTGGTTCA CTTAATCCGG TCAATTTGTT CGCTGCTCGT GGTTGTCTTT
 201  CTCCCCGCCC TCCTTCCCCC TGTTTTGTTT TGTTTCGCTT GCTTTCGGGG
 251  GGACGCTCCT TCCCTCAGTC AGAAGAGCTG GAATTGCTTG AGAGGCGTAT
 301  AAGGAATTAT AAAAGTGGCC AGGAAACACG AGCGCAGTGA CTGCAGAGCT
 351  GCCCTTGGCT TCGGCAAGGC AGCGTGAGCG GCAGAGGGCT CGGGCAGGGG
 401  GCGGGGGGTC TCCTTTTTCC CGTGCGTTCC TCTTCTCCCA GTTCGGATGA
 451  TGTTGCTGTT TCGGACCTCT CGCTGACTCC TGCCCTGTGA TTTTTGCTGA
 501  GCGCTGTGAC TGTTACTCCG TCTCTTTCTG TCTGTGTTTC ACAGTAATGG
 551  ACTGTGATAG AGTTAAGGCC TTTTGGAGGT GAGCTGTGTC ACAGCTGATG
 601  CTTAAACATG TCTGAAGTAG GCACCGAGAC TTTCCCCAGC CCCTCGGCTC
 651  AGCTGAGCCC TGATGCATCC CTTGGCGGGC TCCCGGCTGA GGAGAACATG
 701  CCGGGGCCCC ACAGAGAGGA CAGCAGGGTC CCAGGTGTGG CAGGCCTGGC
 751  CTCGACCTGC TGCGTGTGCC TGGAAGCAGA GCGACTGAAG GGCTGCCTCA
 801  ACTCTGAGAA GATCTGCATC GCCCTATCC TGGCTTGCCT GCTCAGCCTC
 851  TGCCTCTGCA TTGCTGGCCT CAAGTGGGTC TTTGTGGACA AGATTTTTGA
 901  GTATGACTCT CCTACACACC TTGACCCTGG GAGGATAGGA CAAGACCCAA
 951  GGAGCACTGT GGATCCTACA GCTCTGTCTG CCTGGGTGCC TTCGGAGGTG
1001  TATGCCTCAC CCTTCCCCAT ACCTAGCCTT GAGAGCAAGG CTGAAGTGAC
1051  AGTGCAAACT GACAGCTCGC TCGTGCCCTC CAGGCCCTTC CTTCAGCCTT
1101  CTCTCTACAA CCGCATCCTA GATGTCGGGT TGTGGTCCTC TGCCACACCG
1151  TCACTGTCAC CATCCTCCCT GGAGCCTACC ACGGCATCTC AGGCACAAGC
1201  AACAGAAACC AATCTCCAAA CTGCTCCAAA ACTTTCCACT TCTACATCTA
1251  CAACTGGGAC AAGTCATCTC ACAAAATGTG ACATAAAGCA GAAAGCCTTC
1301  TGTGTAAATG GGGAGAGTG CTACATGGTT AAAGACCTCC CAAACCCTCC
```

FIGURE 1B

```
1351  ACGATACCTA TGCAGGTGCC CAAATGAATT TACTGGTGAT CGCTGCCAAA
1401  ACTACGTAAT GGCCAGCTTC TACAAGCATC TTGGGATTGA ATTTATGGAA
1451  GCTGAGGAAC TGTACCAGAA ACGGGTGCTG ACCATAACTG GCATTTGCAT
1501  TGCTCTTCTA GTAGTTGGCA TCATGTGTGT GGTGGCCTAC TGCAAAACCA
1551  AGAAGCAGAG GAAAAAGTTG CATGACCGCC TTCGGCAGAG CCTTCGCTCA
1601  GAGAGGAACA ACGTTATGAA CATGGCAAAT GGGCCACACC ACCCCAACCC
1651  ACCACCAGAC AATGTCCAGC TGGTGAATCA GTACGTTTCA AAAAACATAA
1701  TCTCCAGTGA ACGTGTCGTT GAGCGAGAAA CCGAGACCTC GTTTTCCACA
1751  AGCCACTACA CCTCAACAAC TCATCACTCC ATGACAGTCA CCCAGACGCC
1801  TAGCCACAGC TGGAGTAATG GCCATACCGA AAGCATTCTC TCCGAAAGCC
1851  ACTCCGTGCT CGTCAGCTCC TCAGTGGAGA ATAGCAGGCA CACCAGCCCA
1901  ACAGGGCCAC GAGGCCGCCT CAATGGCATT GGTGGGCCAA GGGAAGGCAA
1951  CAGCTTCCTC CGGCATGCAA GAGAGACCCC TGACTCCTAC CGAGACTCTC
2001  CTCACAGTGA AAGGTATGTC TCAGCTATGA CCACACCAGC TCGCATGTCA
2051  CCCGTTGATT TCCACACTCC AACTTCTCCC AAGTCCCTC CATCTGAAAT
2101  GTCACCACCA GTTTCCAGCT TGACCATCTC CATCCCTTCG GTGGCGGTGA
2151  GTCCCTTTAT GGACGAGGAG AGACCGCTGC TGTTGGTGAC CCCACCACGG
2201  CTGCGTGAGA AGTACGACAA CCACCTTCAG CAATTCAACT CCTTCCACAA
2251  CAATCCCACC CATGAGAGCA ACAGTCTGCC ACCCAGTCCT CTGAGGATAG
2301  TGGAGGATGA AGAGTATGAG ACCACGCAGG AGTACGAACC AGCACAGGAG
2351  CCTCCAAAGA AACTCACCAA CAGCCGGAGG GTGAAAAGAA CAAAGCCCAA
2401  TGGCCATATT TCCAGCAGGG TAGAAGTGGA CTCCGACACA AGCTCTCAGA
2451  GCACTAGCTC TGAGAGCGAA ACAGAAGATG AAAGAATAGG TGAGGATACA
2501  CCATTTCTTA GCATACAAAA TCCCATGGCA ACCAGTCTGG AGCCAGCCGC
2551  TGCATATCGG CTGGCTGAGA ACAGGACTAA CCCGGCAAAT CGCTTCTCCA
2601  CACCAGAAGA GTTGCAAGCA AGGTTGTCCA GTGTAATAGC TAACCAAGAC
2651  CCTATTGCTG TATAAGACAT AAACAAAACA CATAGATTCA CATGTAAAAC
```

FIGURE 1C

```
2701  TTTATTTTAT ATAATGAAGT ATTCCACCTT TAAATTAAAC AATTTATTTT
2751  ATTTTAGCAA TTCCGCTGAT AGAAAACAAG AGTGGAAAAA GAAACTTTTA
2801  TAAATTAAGT ATACGTATGT ACAAATGTGT TATGTGCCAT ATGTAGCAAT
2851  TTTTTACAGT ATTTCCAAAA TGGGGAAAGA TATCAATGGT GCCTTTATGT
2901  TATGTTATGT TGAGAGCAAG TTTTGTACAG CTACAATGAT TGCTGTCCCG
2951  TAGTATTTTG CAAAACCTTC TAGCCCTCAG TTGTTCTGGC TTTTTTGTGC
3001  ATTGCATTAT AATGACTGGA TGTATGATTT GCAAGAATTG CAGAAGTCCC
3051  CATTTGCTTG TTGTGGAATC CCCAGATCAA AAAGCCCTGT TATGGCACTC
3101  ACACCCTATC CACTTCACCA GGAAAAAAAA AAAATCAAAA AAAAAAAAA
3151  AAAAAAAAGA AAAGAAAGAG AAAAAAGAAA AGAAAAAGAA AAAAAAAGCT
3201  GAAAAAATAA AA
```

FIGURE 2

```
   1  GCCCYCHFCR CRCCYRFCFC SFYRMTIVFL A*ADTSLRCS R*ESCLSLWA
  51  IGSLNPVNLF AARGCLSPRP PSPCFVLFRL LSGGRSFPQS EELELLERRI
 101  RNYKSGQETR AQ*LQSCPWL RQGSVSGRGL GQGAGGLLFP VRSSSPSSDD
 151  VAVSDLSLTP AL*FLLSAVT VTPSLSVCVS Q*WTVIELRP FGGELCHS*C
 201  LNMSEVGTET FPSPSAQLSP DASLGGLPAE ENMPGPHRED SRVPGVAGLA
 251  STCCVCLEAE RLKGCLNSEK ICIAPILACL LSLCLCIAGL KWVFVDKIFE
 301  YDSPTHLDPG RIGQDPRSTV DPTALSAWVP SEVYASPFPI PSLESKAEVT
 351  VQTDSSLVPS RPFLQPSLYN RILDVGLWSS ATPSLSPSSL EPTTASQAQA
 401  TETNLQTAPK LSTSTSTTGT SHLTKCDIKQ KAFCVNGGEC YMVKDLPNPP
 451  RYLCRCPNEF TGDRCQNYVM ASFYKHLGIE FMEAEELYQK RVLTITGICI
 501  ALLVVGIMCV VAYCKTKKQR KKLHDRLRQS LRSERNNVMN MANGPHHPNP
 551  PPDNVQLVNQ YVSKNIISSE RVVERETETS FSTSHYTSTT HHSMTVTQTP
 601  SHSWSNGHTE SILSESHSVL VSSSVENSRH TSPTGPRGRL NGIGGPREGN
 651  SFLRHARETP DSYRDSPHSE RYVSAMTTPA RMSPVDFHTP TSPKSPPSEM
 701  SPPVSSLTIS IPSVAVSPFM DEERPLLLVT PPRLREKYDN HLQQFNSFHN
 751  NPTHESNSLP PSPLRIVEDE EYETTQEYEP AQEPPKKLTN SRRVKRTKPN
 801  GHISSRVEVD SDTSSQSTSS ESETEDERIG EDTPFLSIQN PMATSLEPAA
 851  AYRLAENRTN PANRFSTPEE LQARLSSVIA NQDPIAV*DI NKTHRFTCKT
 901  LFYIMKYSTF KLNNLFYFSN SADRKQEWKK KLL*IKYTYV QMCYVPYVAI
 951  FYSISKMGKD INGAFMLCYV ESKFCTATMI AVP*YFAKPS SPQLFWLFCA
1001  LHYNDWMYDL QELQKSPFAC CGIPRSKSPV MALTPYPLHQ EKKKIKKKKK
1051  KKRKEREKRK EKEKKS*KNK
```

FIGURE 3

```
   1  CGGCCTGTAA GATGCTGTAT CATTTGGTTG GGGGGGCCTC TGCGTGGTAA
  51  TGGACCGTGA GAGCGGCCAG GCCTTCTTCT GGAGGTGAGC CGATGGAGAT
 101  TTATTCCCCA GACATGTCTG AGGTCGCCGC CGAGAGGTCC TCCAGCCCCT
 151  CCACTCAGCT GAGTGCAGAC CCATCTCTTG ATGGGCTTCC GGCAGCAGAA
 201  GACATGCCAG AGCCCCAGAC TGAAGATGGG AGAACCCCTG GACTCGTGGG
 251  CCTGGCCGTG CCCTGCTGTG CGTGCCTAGA AGCTGAGCGC CTGAGAGGTT
 301  GCCTCAACTC AGAGAAAATC TGCATTGTCC CCATCCTGGC TTGCCTGGTC
 351  AGCCTCTGCC TCTGCATCGC CGGCCTCAAG TGGGTATTTG TGGACAAGAT
 401  CTTTGAATAT GACTCTCCTA CTCACCTTGA CCCTGGGGGG TTAGGCCAGG
 451  ACCCTATTAT TTCTCTGGAC GCAACTGCTG CCTCAGCTGT GTGGGTGTCG
 501  TCTGAGGCAT ACACTTCACC TGTCTCTAGG GCTCAATCTG AAAGTGAGGT
 551  TCAAGTTACA GTGCAAGGTG ACAAGGCTGT TGTCTCCTTT GAACCATCAG
 601  CGGCACCGAC ACCGAAGAAT CGTATTTTTG CCTTTTCTTT CTTGCCGTCC
 651  ACTGCGCCAT CCTTCCCTTC ACCCACCCGG AACCCTGAGG TGAGAACGCC
 701  CAAGTCAGCA ACTCAGCCAC AAACAACAGA AACTAATCTC CAAACTGCTC
 751  CTAAACTTTC TACATCTACA TCCACCACTG GGACAAGCCA TCTTGTAAAA
 801  TGTGCGGAGA AGGAGAAAAC TTTCTGTGTG AATGGAGGGG AGTGCTTCAT
 851  GGTGAAAGAC CTTTCAAACC CCTCGAGATA CTTGTGCAAA GGCGGAGGAG
 901  CTGTACCAGA AGAGAGTGCT GACCATAACC GGCATCTGCA TCGCCCTCCT
 951  TGTGGTCGGC ATCATGTGTG TGGTGGCCTA CTGCAAAACC AAGAAACAGC
1001  GGAAAAAGCT GCATGACCGT CTTCGGCAGA GCCTTCGGTC TGAACGAAAC
1051  AATACGATGA ACATTGCCAA TGGGCCTCAC CATCCTAACC CACCCCCCGA
1101  GAATGTCCAG CTGGTGAATC AATACGTATC TAAAAACGTC ATCTCCAGTG
1151  AGCATATTGT TGAGAGAGAA GCAGAGACAT CCTTTTCCAC CAGTCACTAT
1201  ACTTCCACAG CCCATCACTC CACTACTGTC ACCCAGACTC CTAGCCACAG
1251  CTGGAGCAAC GGACACACTG AAAGCATCCT TTCCGAAAGC CACTCTGTAA
1301  TCGTGATGTC ATCCGTAGAA AACAGTAGGC ACAGCAGCCC AACTGGGGCC
1351  G
```

FIGURE 4

```
  1  ACKMLYHLVG GASAW*WTVR AARPSSGGEP MEIYSPDMSE VAAERSSSPS
 51  TQLSADPSLD GLPAAEDMPE PQTEDGRTPG LVGLAVPCCA CLEAERLRGC
101  LNSEKICIVP ILACLVSLCL CIAGLKWVFV DKIFEYDSPT HLDPGGLGQD
151  PIISLDATAA SAVWVSSEAY TSPVSRAQSE SEVQVTVQGD KAVVSFEPSA
201  APTPKNRIFA FSFLPSTAPS FPSPTRNPEV RTPKSATQPQ TTETNLQTAP
251  KLSTSTSTTG TSHLVKCAEK EKTFCVNGGE CFMVKDLSNP SRYLCKGGGA
301  VPEESADHNR HLHRPPCGRH HVCGGLLQNQ ETAEKAA*PS SAEPSV*TKQ
351  YDEHCQWASP S*PTPRECPA GESIRI*KRH LQ*AYC*ERS RDILFHQSLY
401  FHSPSLHYCH PDS*PQLEQR TH*KHPFRKP LCNRDVIRRK Q*AQQPNWG
```

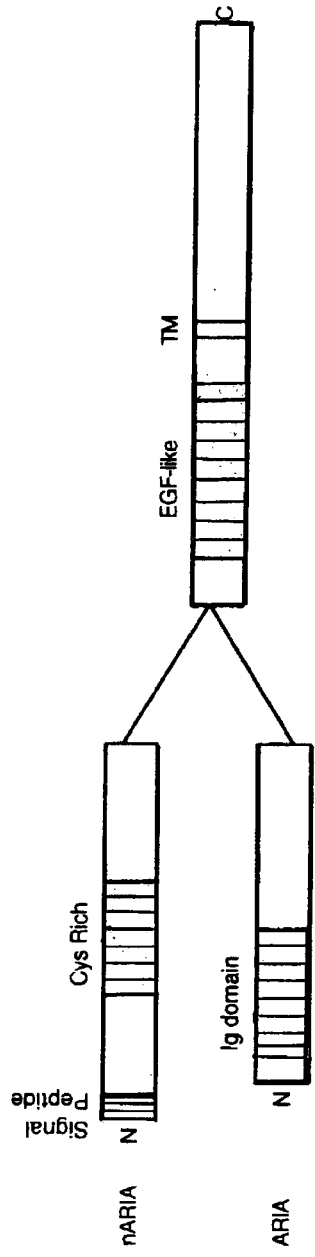
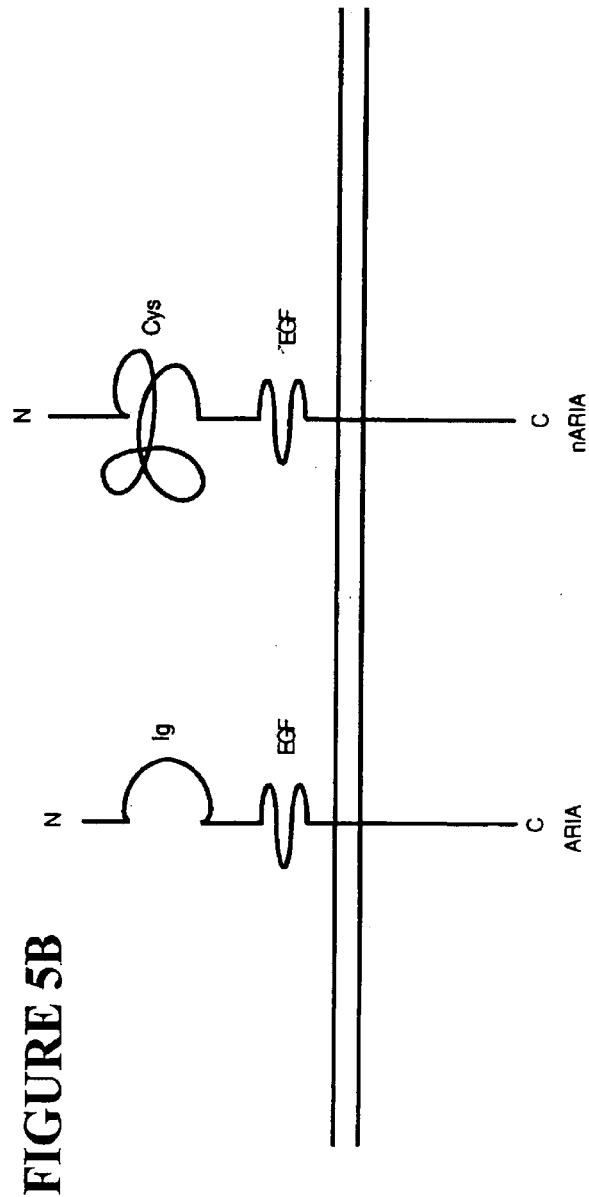
FIGURE 5A
FIGURE 5B

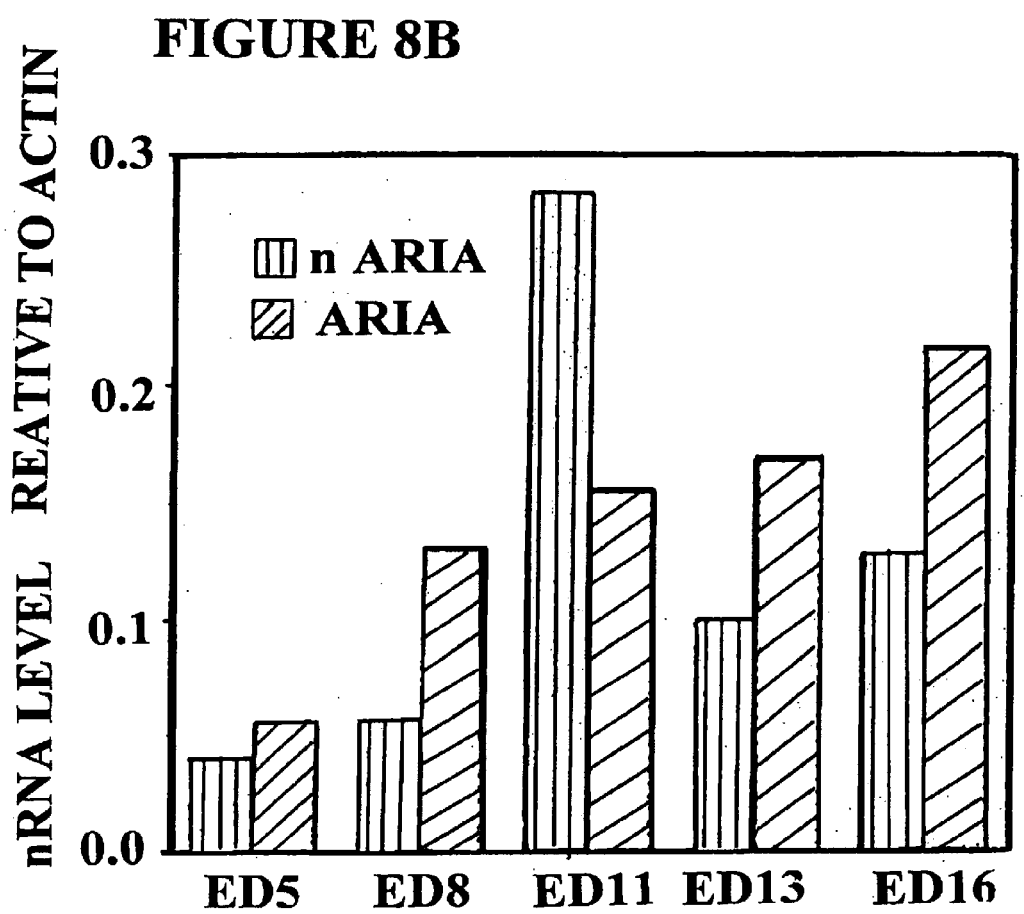

ED5 trunk cross-section
ARIA specific probe

ED5 trunk cross-section
nARIA specific probe

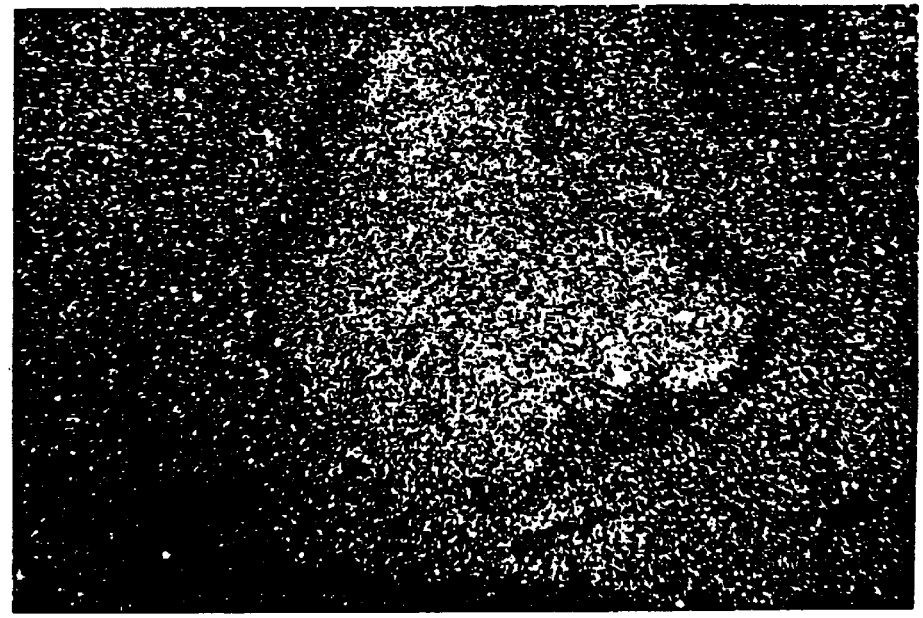
FIGURE 10D ARIA specific probe — ED7 trunk cross-section
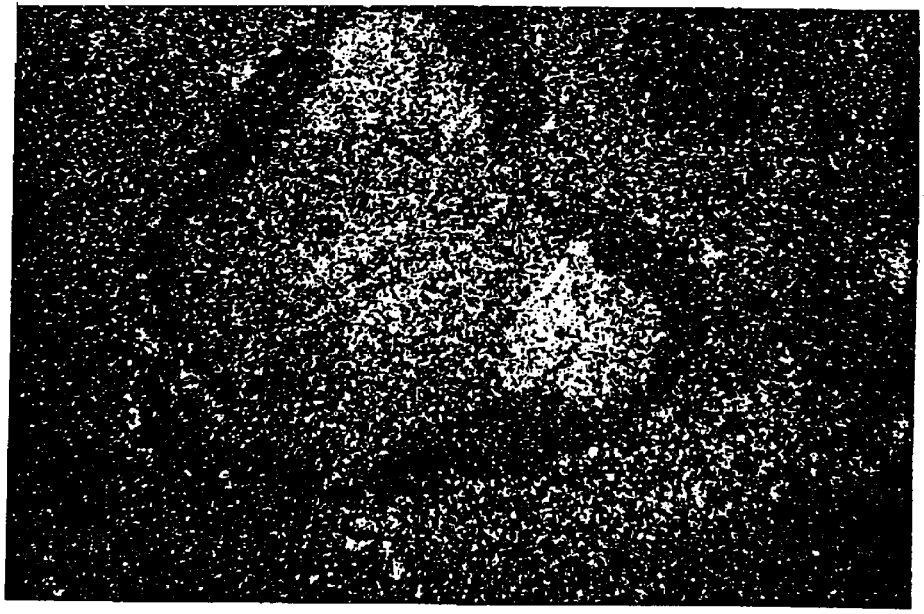
FIGURE 10C nARIA specific probe — ED7 trunk cross-section

A. MCF-7

B. LSG

C. TIME COURSE

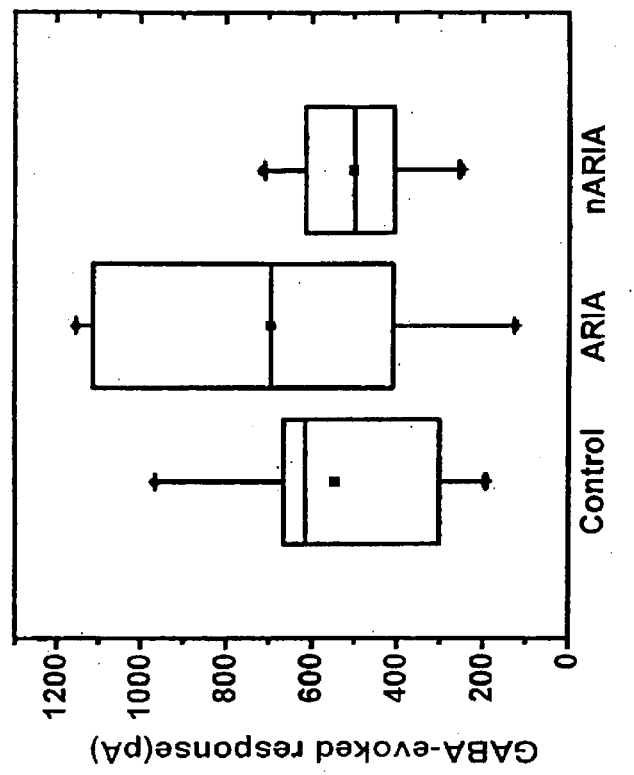
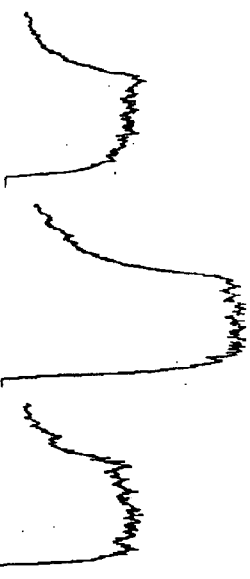
FIGURE 13D
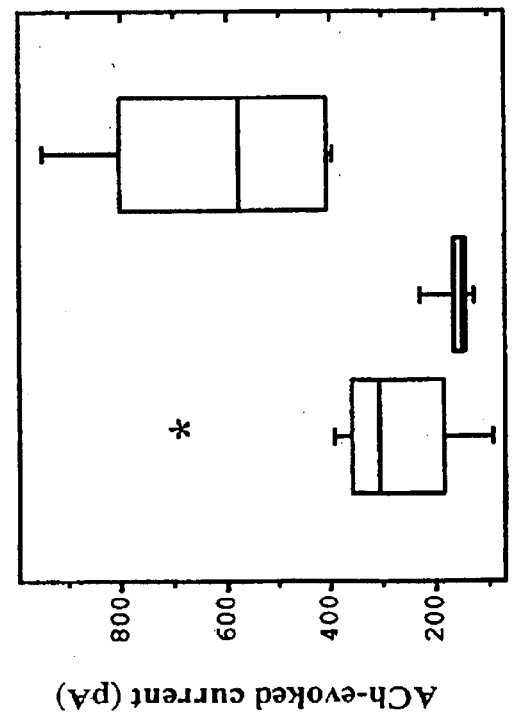
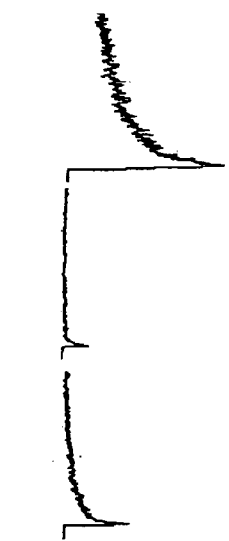
FIGURE 13C no treatment=sympathetic neurons alone
'Pre'=treatment of sympathetic neurons with presynaptic input-conditioned media+various oligos
mmAS=mismatch antisense control
nARIA AS=nARIA specific antisense oligonucleotides
ARIA AS=ARIA specific antisense oligonucleotides

A-FORM OF CYTOPLASMIC DOMAIN OF NARIA (CRD-NEUREGULIN) AND USES THEREOF

A portion of the invention disclosed herein was made with Government support under NIH Grant No. NS29071 from the Department of Health and Human Services. Accordingly, the U.S. Government may have certain rights in this invention.

BACKGROUND OF THE INVENTION

Throughout this application, various publications are referenced by author and date and by arabic numbers in superscript. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

The development and differentiation of embryonic neurons culminates in synapse formation. Neuronal development is an intricate process that involves a cascade of inductive interactions between a neuron and the pre- and postsynaptic partners of that neuron. These highly regulated events are important for the establishment of reliable, yet plastic, synaptic formation and transmission. Correct expression of an array of transmitter-gated channels by neurons is clearly essential to synaptic differentiation, and yet the developmental regulation of this process is poorly understood. In fact, despite overwhelming advances in probing the molecular and biophysical details of ion channels gated by gamma-amino butyric acid (GABA), glycine, glutamate and acetylcholine (ACh) (Betz, 1990; Deneris et al., 1991; McGehee et al., 1995; Role, 1992; Sargent, 1993) the corresponding embryonic versions of these receptors have evaded analysis. Characterization of the biophysical properties of ligand-gated channels in developing neurons and description of their evolution to the mature receptor profile is limited (Brussard et al., 1994; Moss and Role, 1993; Margiotta and Gurantz, 1989). Furthermore, little is known about the mechanism of these changes.

The study of embryonic ligand-gated channels and subsequent modifications of their functional profile during neural development is difficult. Receptor expression prior to synaptogenesis is at a low level. Synapse formation is not synchronous. In the few cases studied, the developmental changes in receptor function are vast (Berg et al., 1989; Engisch and Fischbach, 1992; Arenella et al, 1993; Deneris et al, 1991; McGehee and Role, 1995; Role, 1992; Sargent, 1993). In the establishment of mature synapses, profound alterations in the expression profile of neuronal ligand-gated channels occur. In addition to these changes in expression levels, changes in the cellular distribution, the subunit composition and the biophysical and pharmacological properties occur as well (Margiotta and Gurantz, 1989; Moss and Role, 1993; Moss et al., 1989; Devay et al, 1994; Arenella et al, 1993; Jacob, 1991; Mandelzys et al, 1994; Smith et al, 1983; Vernallis et al, 1993). The interactions between presynaptic and target neurons may play a large role in the extrinsic influences which are believed to modify receptor function throughout development. The mechanism of receptor development remains unclear, however, presynaptic input, target cell regulation, synaptic activity or molecular signals independent of transmission may be involved.

Diversity of Neuronal Nicotinic Receptors

One important feature of neuronal ligand-gated channels, nicotinic acetylcholine receptors (nAChRs) in particular, is the diversity of component subunits and the resultant diversity in channel subtypes (Boulter et al, 1986; Conroy et al., 1992; Grynkiewicz et al., 1985; Lindstrom et al., 1990; Luetje and Patrick, 1991; McGehee and Role, 1995; Papke and Heinemann, 1991; Ramirez-Latorre et al., submitted; Role, 1992). Neuronal nAChRs were the first of the ligand-gated ion channels studied to display this degree of structural and functional complexity. Although nAChRs comprise only two distinct subunit types, there are multiple homologous forms of each subunit encoding gene. There are 8 neuronal "α" subunit genes ($\alpha 1-\alpha 8$) and 3 neuronal "β" subunit genes ($\beta 2-\beta 4$) cloned to date (Boulter et al., 1986; Heinemann et al., 1990; Nef et al., 1988; Seguela et al., 1993; Wada et al., 1989). With this array as a starting point, there could be more than $10^5$ varieties of pentameric nAChR complexes (McGehee et al., 1995 and Role, 1992). Study of native nAChRs indicates that the actual number of subunit combinations is less than theory would predict. Biochemical, immunochemical, and antisense deletion experiments to identify native compositions of nAChRs demonstrate that relatively few subunit combinations are likely to be found in native nAChRs. For example, the nAChRs expressed by autonomic and habenula neurons have been studied in detail (Brussard et al., 1994; Devay et al., 1994; Listerud et al., 1991; Clarke et al., 1986) and provide specific examples of the subunit composition of each nAChR channel subtype expressed. In view of the documented evolution of these neuronal nAChR channels during embryonic development, and the array of molecular and biophysical tools available to study these channels in detail, an understanding of the developmental regulation of nAChR subunit and channel subtype diversity may be close at hand. Numerous studies implicate the interaction during the formation of synaptic connections between the presynaptic and postsynaptic cells in the development of mature neuronal receptors (Arenella et al., 1993; Boyd et al., 1988; Brussaard et al., 1994b; Brussaard et al., 1994; Devay (in preparation; Devay et al., 1994; Gardette, et al., 1991; Jacob 1991; Levey et al., 1994; Mandelzys et al., 1994; Moss et al., 1989).

Regulation of Neuronal Phenotype During Development: Contribution of Target Interactions.

Neuronal differentiation is induced by the interaction of developing neurons with target cells. One example is that of the evolution of transmitter phenotype in a special class of sympathetic neurons that evolve from an adrenergic to a cholinergic phenotype in the course of normal development. Although early on, these neurons synthesize, package and release catecholamines, the formation of synapses with the target sweat glands is accompanied by a change in transmitter expression that ultimately produces a mature cholinergic phenotype. This change in transmitter expression requires both pre- and postsynaptic signals. Thus, catecholamine release from the embryonic neuron is required to induce the release of a cell differentiation factor\leukemia inhibitory factor (CDF/LIF)-like factor called sweat gland factor (SGF) from the presumptive sweat glands. SGF, released via activation of target adrenergic receptors, interacts, with specific receptors on the innervating neuron. SGF induces the cellular machinery required for ACh synthesis and release in the presynaptic neuron. Thus, the attainment of a mature transmitter phenotype is regulated by both synaptic activity and target derived signals, offering an explanation for how the innervation of target tissues regulates nAChR expression in CNS and PNS neurons.

This example is one of many implicating target-derived factors in the control of neuronal survival, proliferation, differentiation, migration, and neurite outgrowth. Although there are many factors that could mediate target effects on neuronal differentiation, the expression patterns and biological activities of factors identified to date identify a few candidates for proposed studies of nAChR regulation. (1) Ciliatory neurotropic factor (CNTF) mimics the effect of SGF in inducing a cholinergic phenotype. It has also been shown to promote differentiation of sympathetic precursor cells and likely participates in target-induced changes in nAChR expression. CNTF is expressed in numerous sympathetic targets including smooth muscle and kidney. (2) Activin and related members of the Transforming Growth Factor β (TGFβ) family, can also regulate the differentiation of the transmitter phenotype in autonomic neurons. These factors are expressed in sympathetic targets such as smooth muscle, sweat glands etc. (3) CDF/LIF mimics SGF by inducing a cholinergic phenotype. This factor is secreted by smooth muscle and heart muscle. Although less is known about either the activity or the distribution of these factors in the central nervous system (CNS), it is likely that CNS and peripheral nervous system (PNS) neurons may be regulated by similar signaling molecules.

Regulation of Receptor Synthesis and Distribution in Muscle: Contribution of Presynaptic Signals Classical studies of Fischbach, Cohen, and McMahan of the nerve-muscle junction demonstrate that the incoming motor nerve is a potent regulator of muscle-nAChRs. Prior to innervation, muscle expresses an embryonic form of nAChR which is diffusely distributed over the cell surface. The expression of the muscle-nAChR is eventually down-regulated to a diffuse distribution. Elimination of muscle-nAChRs by innervation is accompanied by an increase in local synthesis, insertion and formation of high-density clusters of muscle-nAChR at the synaptic site. At later stages of synaptic development, there are marked changes in the biological properties of muscle-nAChR channels due to alterations in subunit gene expression. This produces "adult" type muscle-nAChR complexes of distinct subunit composition. Molecular signals that are believed to mediate these changes in muscle-nAChR distribution and synthesis have been identified and cloned, namely, agrin and AChR Inducing Activity (ARIA). Recombinant agrin alters the distribution of pre-existent muscle-nAChRs with no effect on synthesis or insertion of new receptors. In contrast, recombinant ARIA induces muscle-nAChR subunit gene expression, increasing the rate of appearance of new surface receptors from 3–5%/hr to 10–20%/hr.

It is possible that there are common regulatory mechanisms between nAChR and muscle-nAChR. It is believed that nAChRs on both CNS and PNS neurons evolve from low density and diffuse distribution to clustered and highly dense synaptic patches following innervation. Finally, like muscle-nAChRs, there are marked changes in the biophysical properties of nAChRs during development and presynaptic input may induce some of these changes, e.g., channel conductance and opening frequency.

Despite the essential role of ligand-gated ion channels in synaptic transmission between neurons, little is known about changes in their expression, function, distribution and subunit composition during neural development. Nicotine-induced enhancement of acquisition and consolidation of short term memories is believed to be mediated by presynaptic nAChR activation since this activation facilitates a broad array of CNS synapses. In view of the impact that developmental changes in nAChRs have on neuronal excitability, synaptic efficacy and synaptic plasticity, studies of the regulatory controls of nAChR expression are essential. One avenue of study focuses upon the proteinaceous factors that appear to modulate receptor gene expression. One factor previously identified and cloned is heregulin (See Vandlen and Holmes, U.S. Pat. No. 5,367,060).

To date, 10 different proteins that result from alternative splicing of the heregulin gene have been described. Among these are the growth factors neu differentiation factor (NDF) (Wen et al., 1992), glial growth factor (GGF) (Marchionni et al., 1993), ARIA (Falls et al, 1993; Fischbach et al., 1994), and the heregulin isoforms (Holmes, 1992; Wen et al., 1994). The reported isoforms are principally membrane bound proteins which can be solubilized by proteolysis. The extracellular domains of these proteins consist of an N-terminal domain followed by an immunoglobulin-like (Ig-like) domain, a linker region, an EGF-like domain, and a second linker region (FIG. 5). These proteins are ligands for the epidermal growth factor (EGF) family of receptor tyrosine kinases. Binding of the ligand to the EGF receptor family members erbB3/HER3 or HER4 results in activation of the tyrosine kinase activity of the receptor. Other family members can be activated by trans-phosphorylation via the activated members.

Other members of the heregulin/NDF/ARIA family have been described in previous patent publications. PCT International Publication No. WO 94/08007, published Apr. 14, 1994, entitled "Trophic factor having ion channel-inducing activity in neuronal cells" describes neurotrophic factors designated as ARIA, which are able to induce the formation of ion channels. This publication also shows how ARIA is associated with both nervous tissue and skeletal muscle. ARIA has an Ig-like domain and an EGF-like domain in the extracellular region. U.S. Pat. No. 5,367,060, issued Nov. 22, 1994, entitled "Structure, production and use of heregulin", from U.S. Ser. No. 847,743, filed Mar. 6, 1992 by Richard L. Vandlen and William E. Holmes, discloses a polypeptide with a binding affinity for the $p185^{HER2}$ receptor. Vandlen and Holmes also disclose purification methods required to isolate heregulin and uses of the heregulins and antibodies specific to the heregulins as therapeutic agents. This polypeptide is related to but distinct from the ARIA protein.

SUMMARY OF THE INVENTION

This invention provides an assay for diagnosing whether a subject has or is predisposed to developing a neoplastic disease which comprises: a) obtaining a biological sample from the subject; b) contacting the sample with an agent that detects the of an extracellular domain of nARIA (CRD-neuregulin) or an isoform thereof; c) measuring the amount of agent bound by the sample; d) comparing the amount of agent bound measured in step )c with the amount of agent bound by a standard normal sample, a higher amount bound by the sample from the subject being indicative of the subject being predisposed to developing a neoplastic disease. One embodiment of this invention is a method for maintaining synaptic connections between a neuron and a target cell comprising contacting the target cell with an nARIA polypeptide or a nucleic acid molecule encoding nARIA in an amount sufficient to induce the formation of a synaptic junction.

BRIEF DESCRIPTION OF THE FIGURES

FIGS. 1A–1C: Nucleotide sequence of chicken nARIA (SEQ ID NO: 1).

A nucleic acid sequence encoding a splice variant from the heregulin gene is shown. This sequence is a compilation of the sequences derived from the ExoIII deletion series on the pBluescript II KS (+) subclone of phage #3 from a chick E13 total brain cDNA library screened with a rat pro-heregulin beta 1 probe generated by PCR amplification. The sequence was determined using the M13 reverse primer. The length is 3212 bases. The break in homology to the ARIA sequence occurs at a known splice site. The nucleotide sequences from base pair number 1293 downstream to the poly-A tail of the nARIA clone are identical to ARIA. The sequences upstream from base pair number 1293 encode a unique splice variant (i.e. bp 1293-bp 3212), nARIA.

FIG. 2: Amino acid sequence of chicken nARIA (SEQ ID NO: 2).

An amino acid sequence encoding a splice variant from the heregulin gene is shown. This sequence is a compilation of the sequences derived from the ExoIII deletion series on the pBluescript II KS (+) subclone of phage #3 from a chick E13 total brain cDNA library screened with a rat pro-heregulin beta 1 probe generated by PCR amplification. The sequence was arrived at using the M13 reverse primer. The length is 1070 amino acids. The asteriks denote unclear results these stop condons.

FIG. 3: Nucleotide sequence of the unique portion of the human nARIA gene (SEQ ID NO: 3).

A nucleic acid sequence encoding the human nARIA (hnARIA) a splice variant from the heregulin gene, nARIA is shown. The product was subcloned into pBluescript II KS (+) the 5' end of the transcript is at the M13 end of the multiple cloning site (MCS). The length is 1351 bases. The unique portion of nARIA spans from base 93 to base 758.

FIG. 4: Amino Acid sequence of the unique portion of the human nARIA protein (SEQ ID NO: 4).

An amino acid sequence encoding the unique portion of the human nARIA is shown. The product was subcloned into pBluescript II KS (+) the 5' end of the transcript is at the M13 end of the MCS. The length is 449 amino acids.

FIGS. 5A–5B: Comparison of gene structure of nARIA with ARIA (A) Comparison of the gene structure of the chicken nARIA cDNA with ARIA human nARIA, heregulin, and NDF. (B) Comparison of the exon structure of splice variants of the ARIA/NDF/Heregulin gene. The sequence we cloned (nARIA) has a unique N terminal domain devoid of Ig-like repeats common to other ARIA variants.

Figure 6:
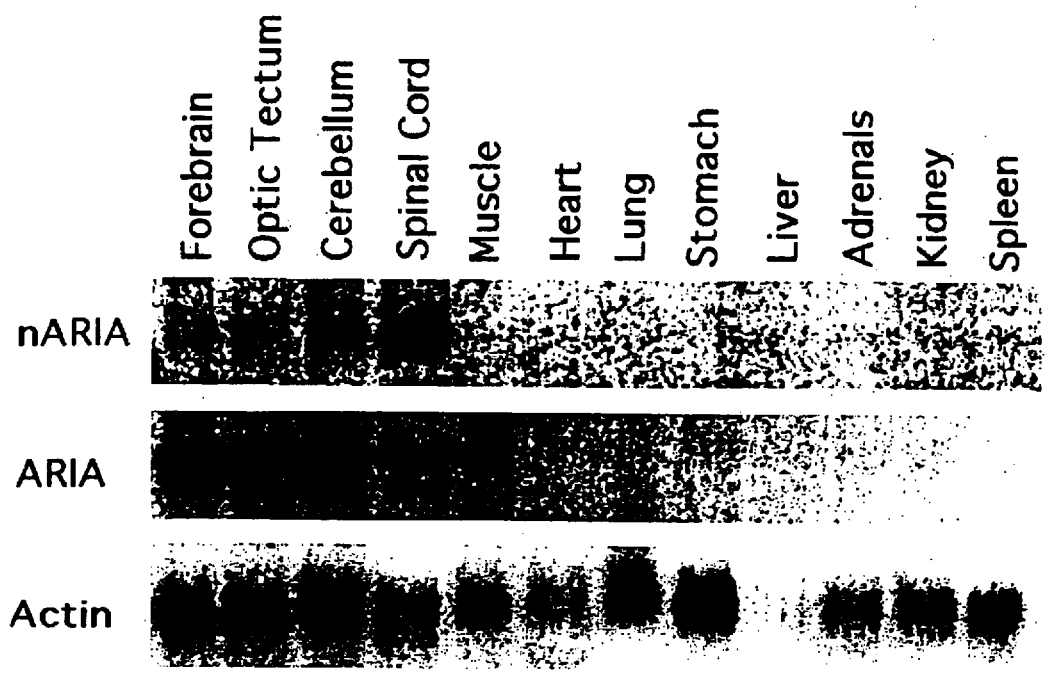

FIG. 6: Stage E13 multiple tissue Northern blot.

Multiple tissue Northern blots were screened with probes specific for unique domains of nARIA and were compared with those probed with an ARIA specific probe. The ARIA probe indicates that this form is present in skeletal muscle (pectoral muscle) whereas expression of nARIA is restricted to nervous tissue.

Figure 7:
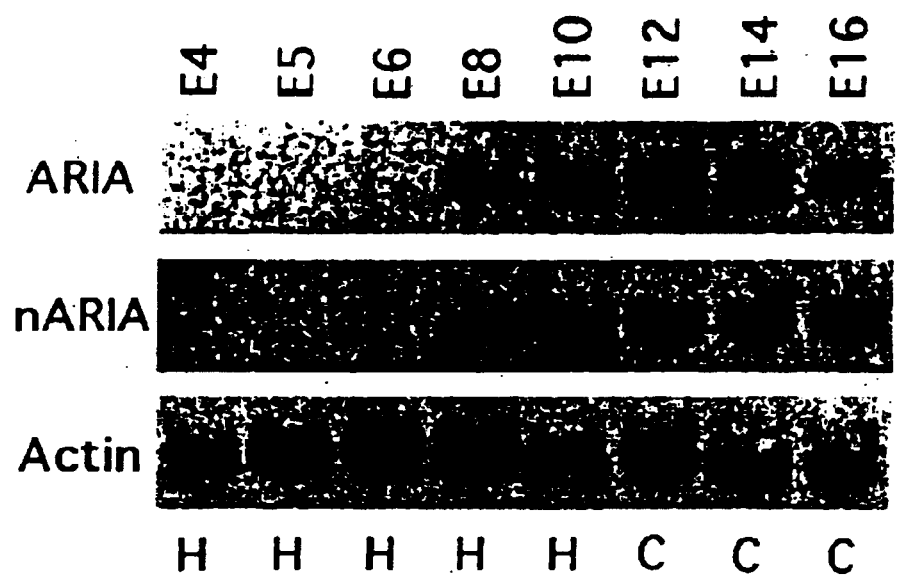

FIG. 7: Developmental Northern analysis of ARIA and nARIA in the chick hindbrain and cerebellum Northern blot analysis was performed on RNA samples from chick embryonic stages E4 through E16. Oligonucleotides specific for either nARIA or ARIA were used as probes. H-hindbrain; C-cerebellum.)

Figure 8A:
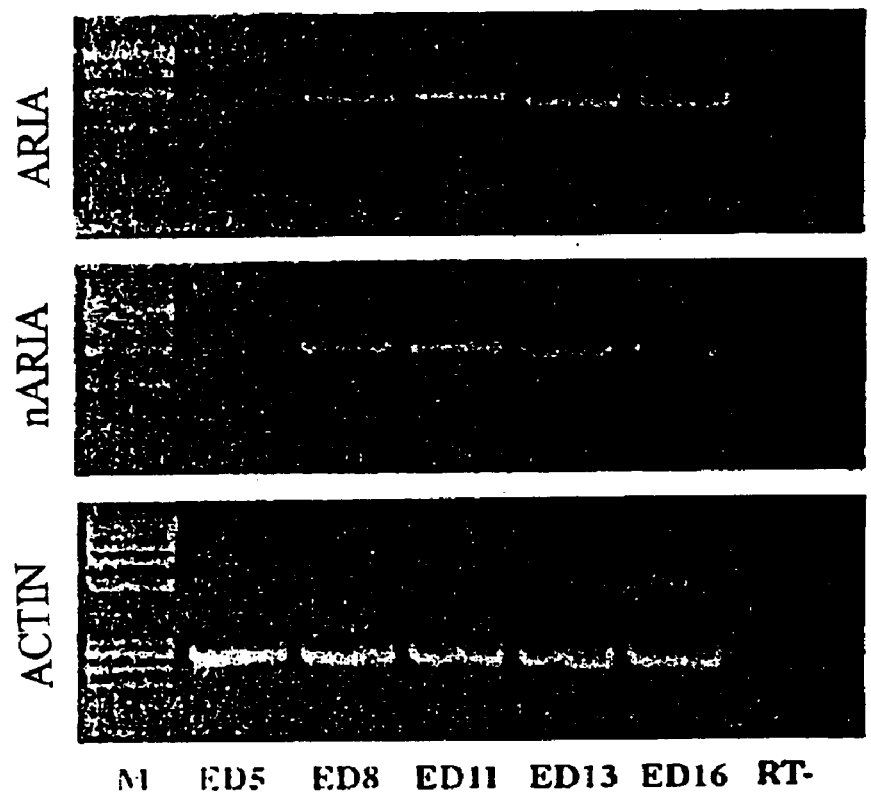

FIGS. 8A–8B: RT-PCR analysis of the developmental expression pattern of nARIA in the chick brain compared with ARIA.

(A) The developmental expression pattern of nARIA and ARIA in chick brain as detected by RT-PCR is shown. (B) Relative quantification of ARIA and nARIA mRNA levels normalized with actin mRNA levels is shown.

Figure 9A:
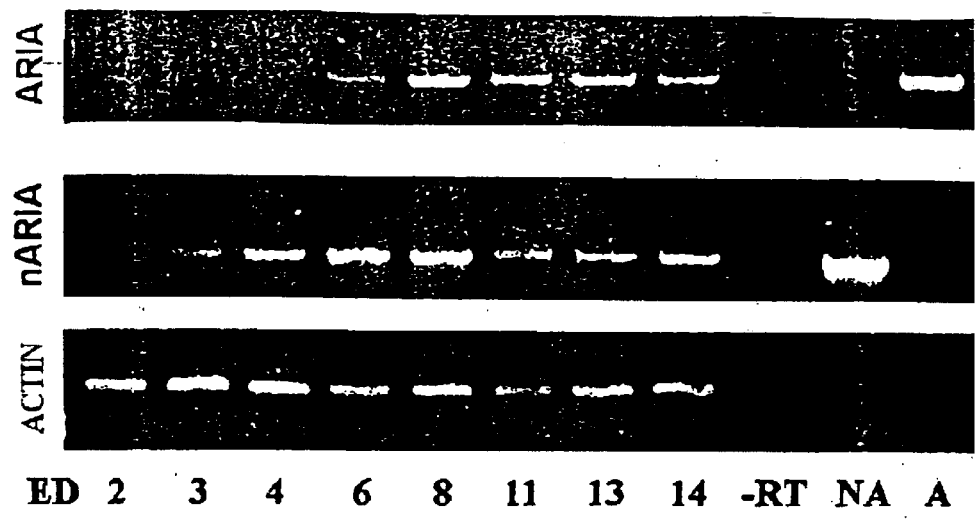
Figure 9B:
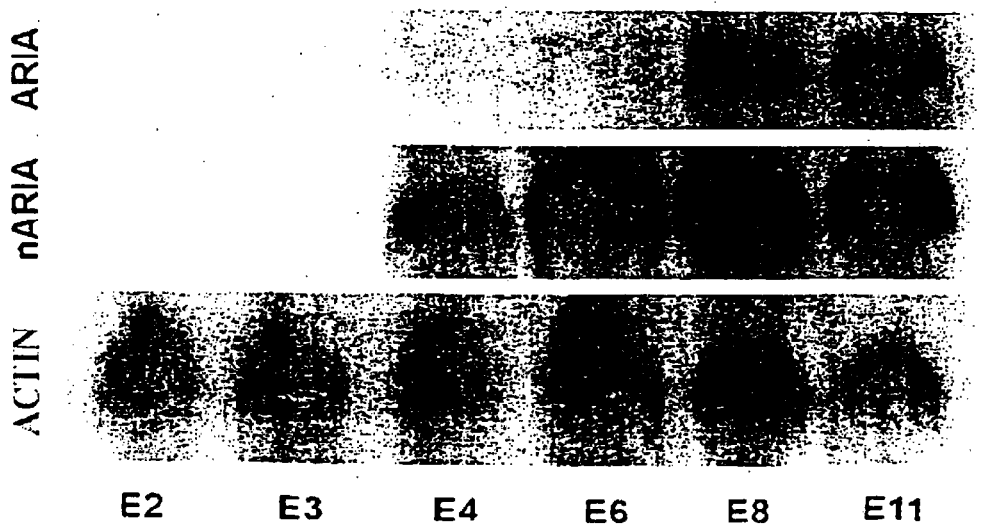
Figure 9C:
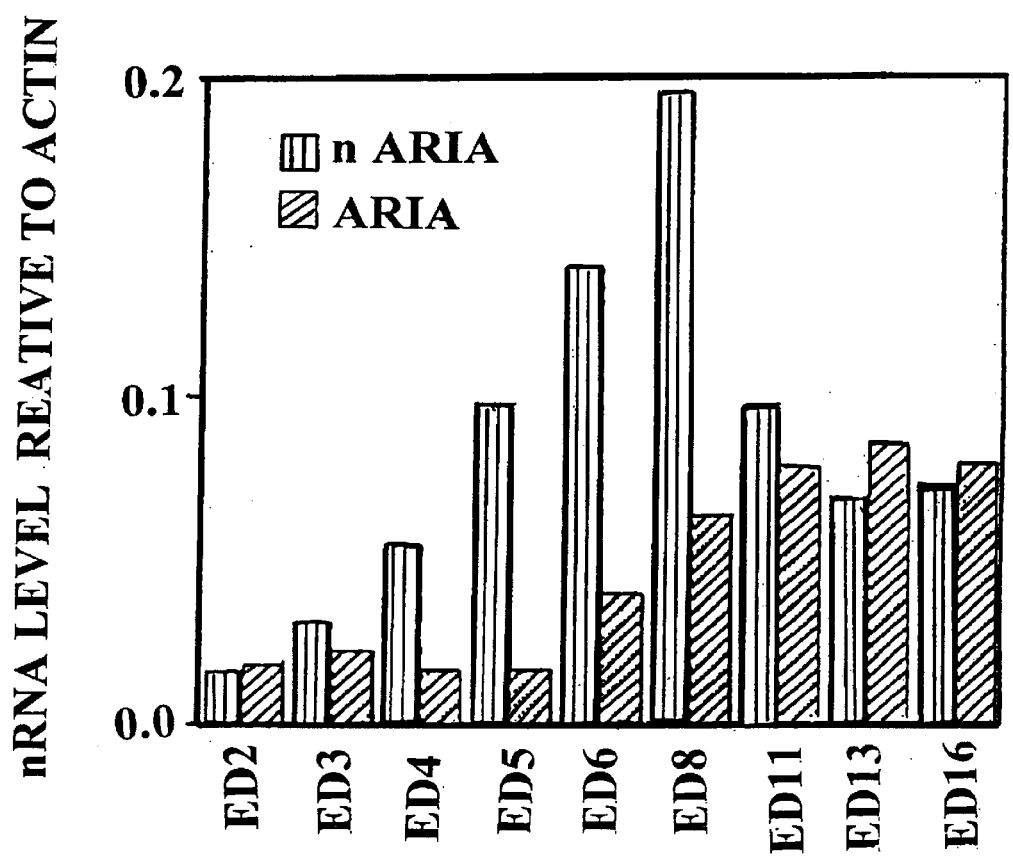
Figure 10B:
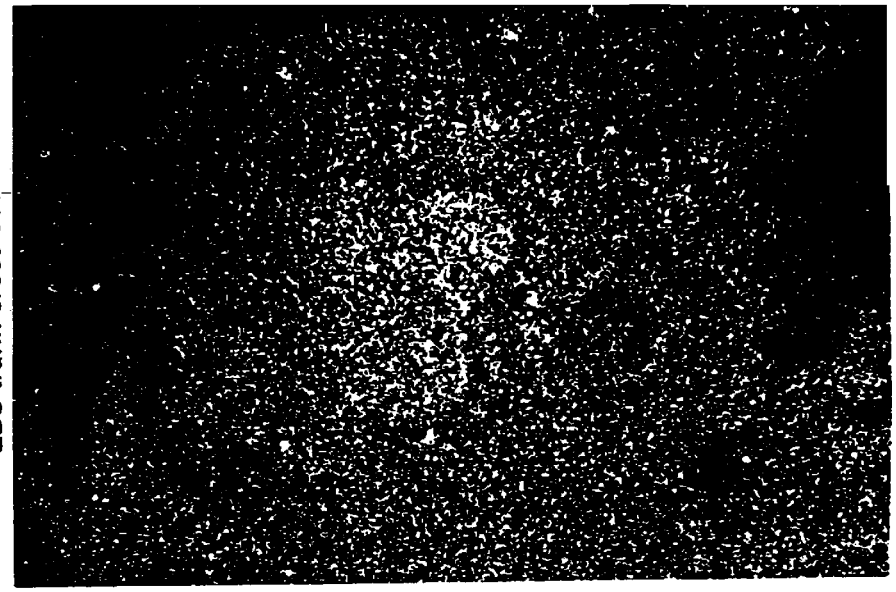
Figure 10A:

FIGS. 9A, 9B and 9C: nARIA and ARIA expression in the developing chick spinal cord as detected by PCR and Northern hybridization analysis.

(A) Northern blot of ARIA (top) and nARIA (bottom). All probes and primers are directed against sequences specific to nARIA and/or ARIA. Northern analysis indicates the mRNA of nARIA is detectable by E3 and robust by E4 whereas initiation of ARIA expression occurs later (e6-8) and is detectable at E6, but not robust until E8. (B) PCR detection of mRNA expression of ARIA and nARIA in developing chick spinal cord. Note specificity of primers tested on full length cDNAs (NA, A) (—RT: no reverse transcriptase reaction; NA—nARIA positive control; A—ARIA positive control). (C) Comparison of nARIA and ARIA mRNA levels relative to actin.

FIGS. 10A–10D: In situ hybridization of chick ED5 trunk cross-section of neural tissue with probes specific for nARIA and ARIA.

The probe specific for nARIA contains the Cys-rich domain and the probe specific for ARIA contains the Ig domain. Different patterns of expression are observed. A positive signal is observed in the presumptive preganglionic neurons with the nARIA probe but not with the ARIA probe. (A-D) ED5 trunk cross section. (A,C) nARIA specific probe. (B,D) ARIA specific probe.

Figure 11A:
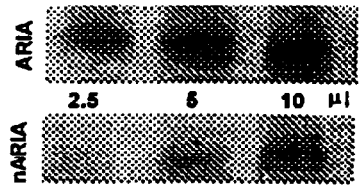
Figure 11B:
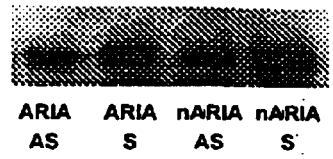
Figure 11C:

FIGS. 11A, 11B and 11C: nARIA induces tyrosine phosphorylation.

(A) Phosphorylation of MCF7 cell line demonstrating activity of both recombinant ARIA and nARIA as ligands for tyrosine kinase-linked receptors. Dose (A) and time (C) dependence of ARIA (A) and nARIA (A,C) phosphorylations in MCF-7 cells. (B) Comparison of recombinant nARIA and ARIA tyrosine phosphorylation of E9 lumbar sympathetic ganglia (LSG).

Figure 12:
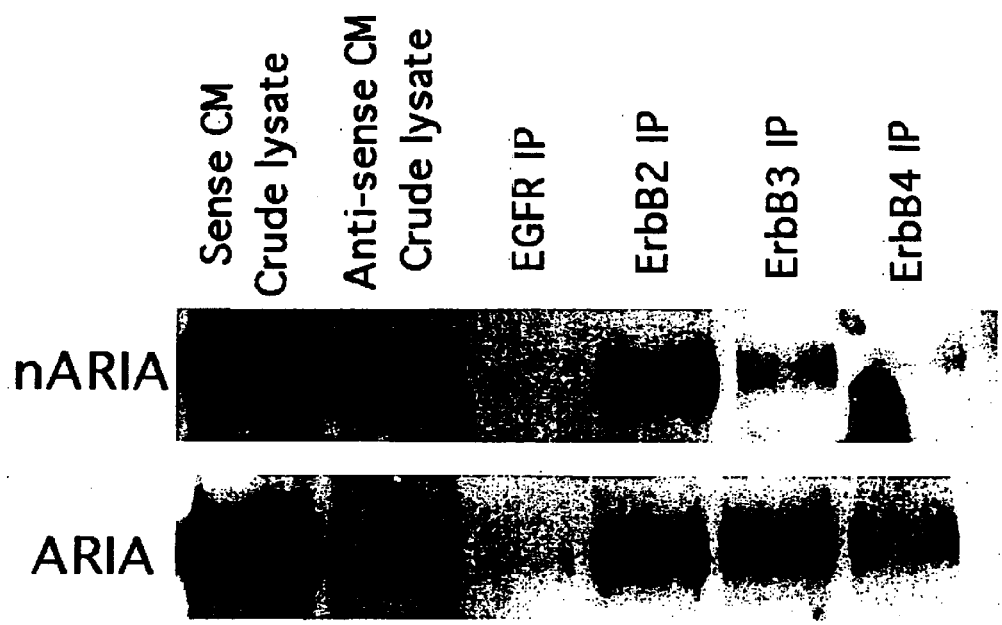
Figure 13A:
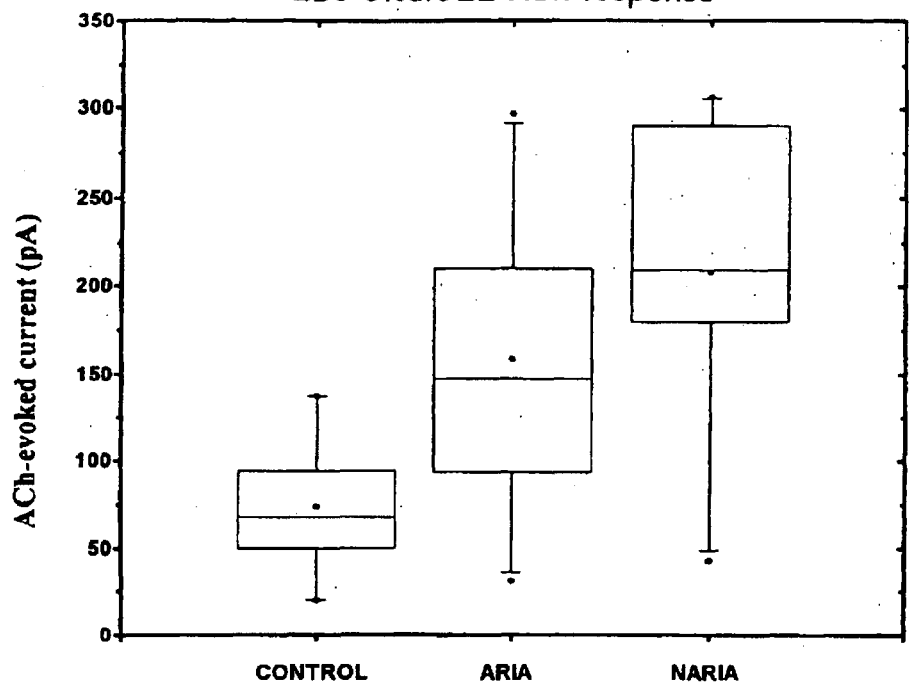
Figure 13B:
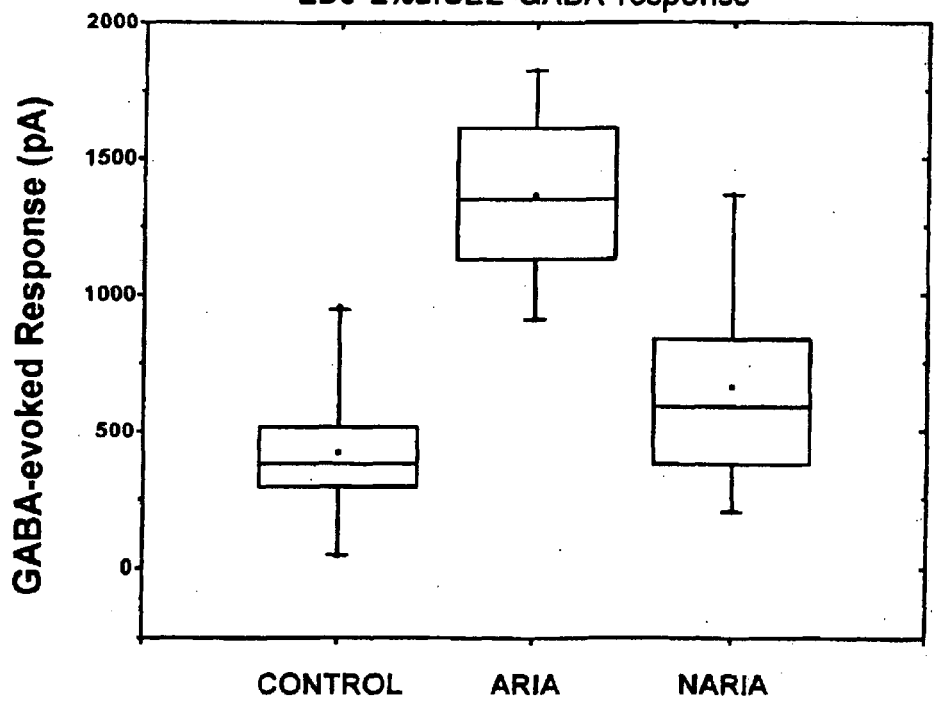

FIG. 12: Anti Phosphotyrosine Western Blot of MDA-MB-453 cells treated with conditioned media.

Media conditioned by COS1 or HEK293 cells transiently transfected with the nARIA clone (sense configuration) activates tyrosine kinase activity in the breast tumor cell lines MCF7 or MDA-MB-453 above the basal levels of tyrosine kinase activity (antisense configuration). The levels of phosphorylation of EGFR family members relative to one another was different between ARIA and nARIA.

FIGS. 13A–13D: Electrophysiological assay of transmitter gated macroscopic currents.

(A,C) ACh-evoked current. (B,D) GABA-evoked response. Treatment of primary cultures of sympathetic neurons from E11 chicks with recombinant nARIA for two days increases the magnitude of macroscopic currents activated by acetylcholine and appears to decrease the currents gated by GABA.

Figure 14A:
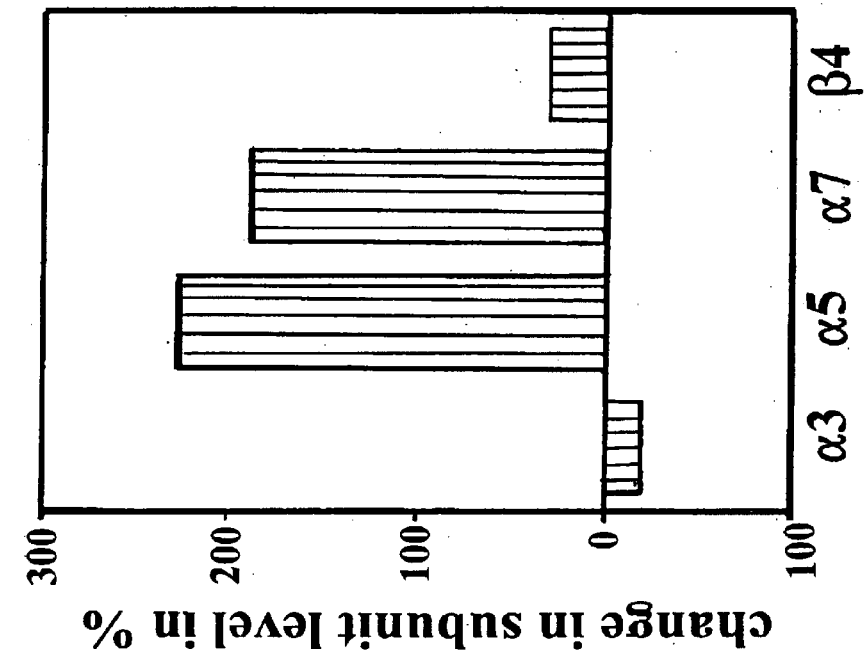
Figure 14B:
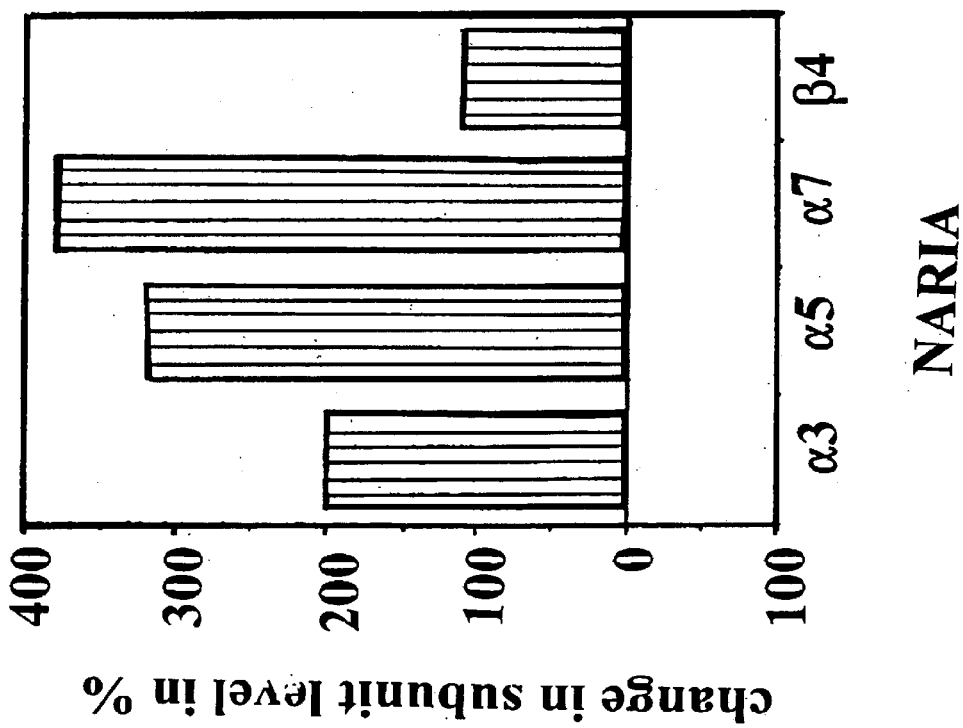

FIGS. 14A–14B: nARIA enhances expression of the nAChR subunit genes α3, α5, α7 and β4 and increases the magnitude of $I_{P\,(ACh)}$.

(A) Assay of nAChR subunit gene expression in E9 neurons maintained in vitro for 3 days and then treated for 24 hrs with 10 µl of recombinant nARIA (left) of ARIA (right) by quantitative RT-PCR. (B) Assay of $I_{P(ACh)}$ in E9 neurons maintained in vitro for 3 days and then treated for 48 hrs with 10 µl of recombinant nARIA or ARIA or antisense construct of each (control). Macroscopic currents evoked by 500 µM ACh. Peak current ($I_{P(ACh)}$) analyzed with non parametric tests appropriate for non-normally distributed values. Box-plots reveal the mid 50% of the data, whiskers delineate the 90% distribution. * indicates outliers. The nARIA induced increase and ARIA induced decrease in ($I_{P(ACh)}$) peak current are significant vs antisense controls at p<0.01, respectively.

Figure 15:
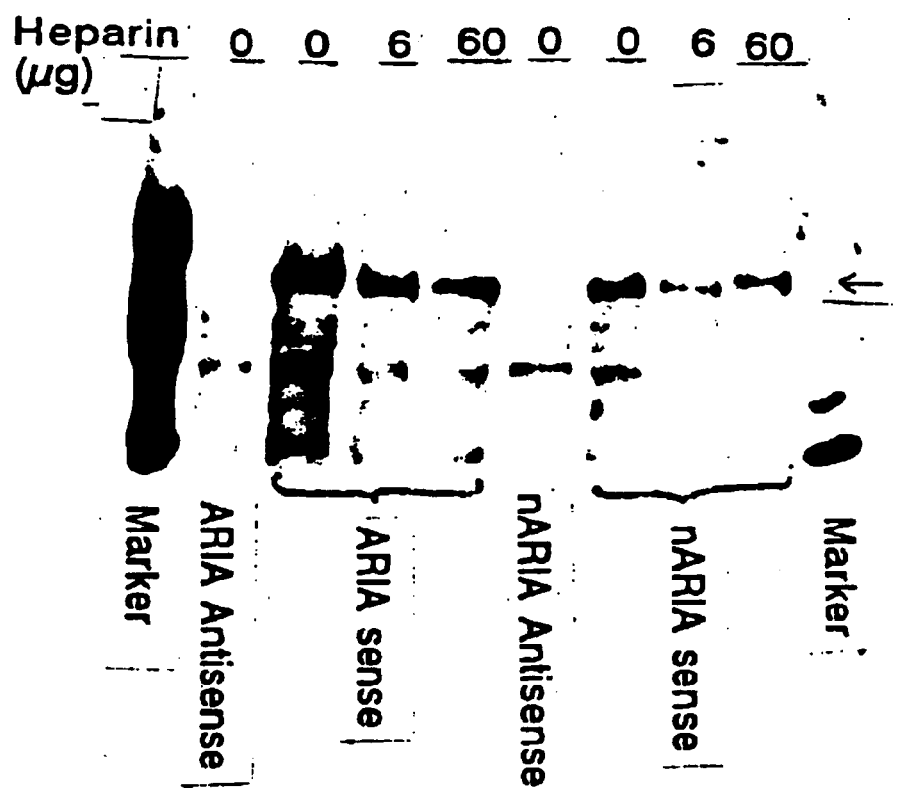

FIG. 15: Comparison of the affinity of nARIA vs ARIA for heparin sulfate proteoglycan.

MCF7 breast tumor cells were treated with conditioned media from either ARIA or nARIA transiently transfected COS1 cells. Some of the media was prebound with heparin attached to glass beads. Prior to treatment, the beads were pelleted by centrifugation to remove any heparin associated proteins. The supernatant was used to treat the MCF7 cells and tyrosine phosphorylation of the ARIA/nARIA receptor was analyzed.

Figure 16:
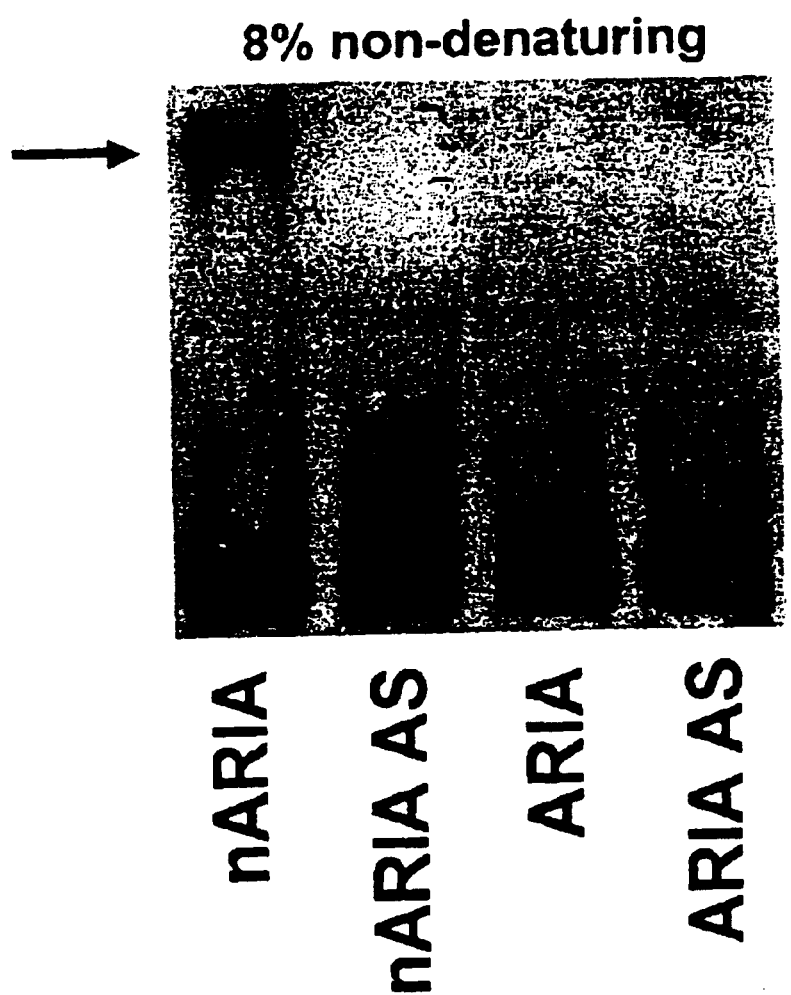

FIG. 16: The anti-nARIA antibody is specific for recombinant nARIA

Figure 17:
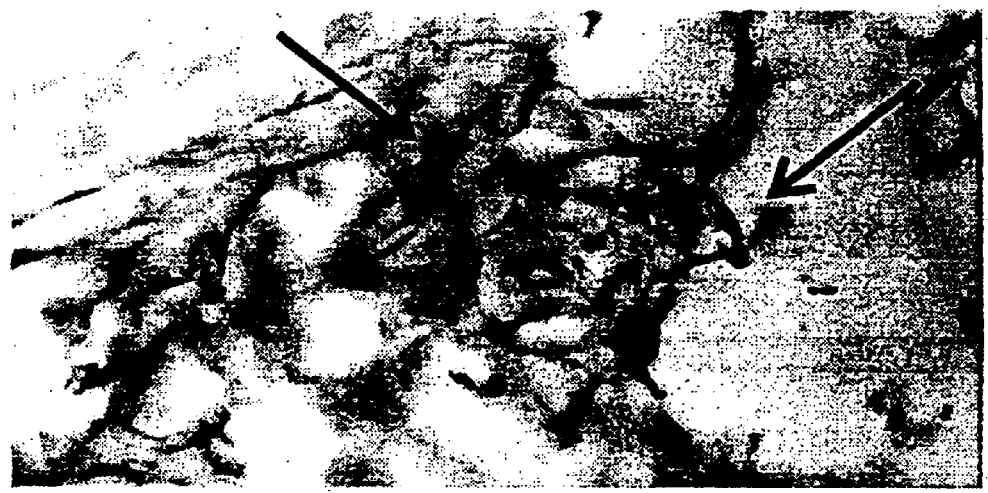

FIG. 17: Anti-nARIA antibodies reveal targeting of nARIA to azon terminals at CNS and PNS synapses FIG. 18: nARIA induction of nAChR expression is more potent that the Ig-Containing isoforms.

Figure 19:
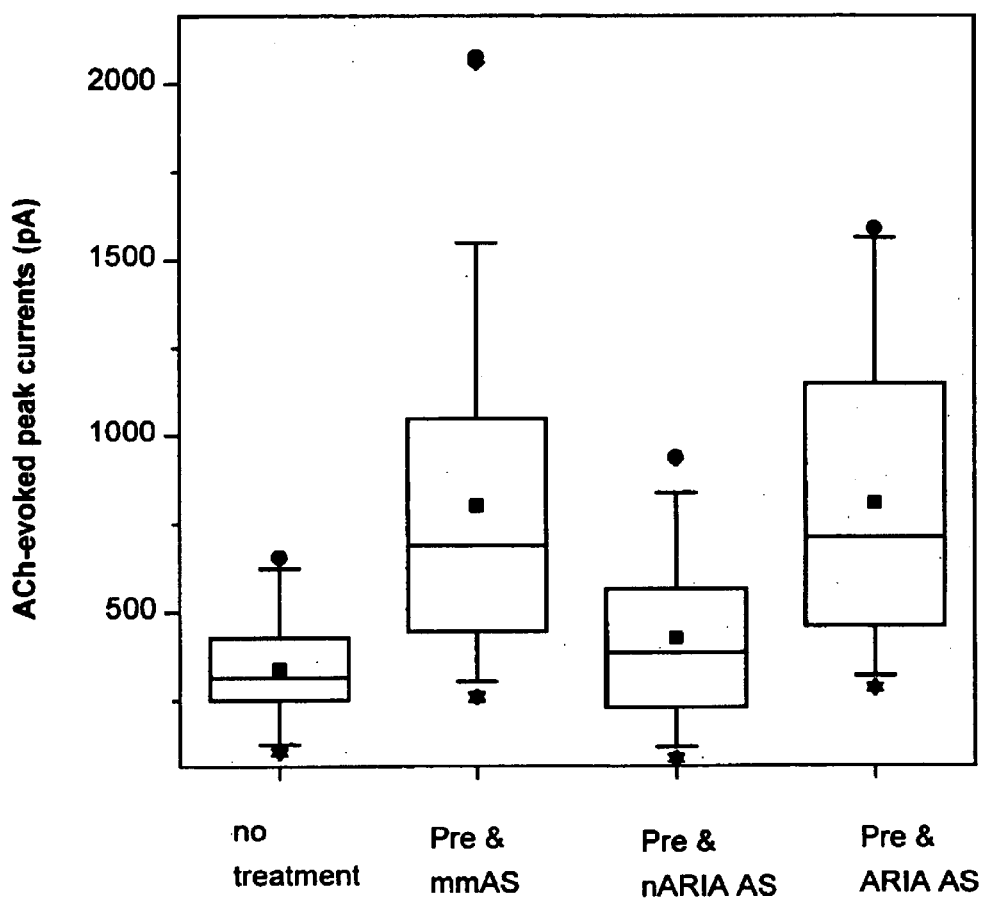

FIG. 19: Deletion of nARIA with isoform-specific antisense oligonucleotides reveals that nARIA is both necessary ans sufficient for the regulation of nAChR expression by presynaptic input.

FIG. 20: Disruption of CRD-NRG-1 gene products.

(A) Schematic diagram of β-form neuregulin-1 gene products (.β-forms differ from α-forms in the EGF-like domain). Splice variants of the NRG-1 gene and the various nomenclatures used in the literature are shown. a,b,c refer to three variants of the cytoplasmic domain. Ext, extracellular, Tm, transmembrane, CYTO, cytoplasm.

(B) Schematic diagram of the wild-type CRD-containing allele, the targeting vector, and the mutated allele. The barbell indicates the site of the nonsense mutation/Xba I site. Arrow and circled X schematically indicate that the nonsense mutation creates a translation stop codon. Note that the neo cassette is inserted in the antisense orientation into the intron 3' to the CRD-exon.

(C) Southern blot analysis of genomic DNA. Left. EcoRI/Eco RV double digest, with probe A; Right, Xba I digest, with probe B.

(D) Southern Blot analysis of cDNA to examine neonatal neuregulin-1 transcripts. Top. Schematic representation of CRD and Ig containing neuregulin-1 cDNAs. Arrowheads are per primers; solid bands are Ig and TM oligo probes used for Southerns; hatched area is CRD-specific otigo probe. Note the presence of CRD-containing, Ig-containing, and EGF-TM-cytoplasmic containing transcripts in CRD-NRG-1 $^{(+/+)}$ and CRD-NRG-1 $^{(-/-)}$ mice and that CRD transcripts are digested with Xba I only in CRD-NRG-1 $^{(-/-)}$ mice.

(E) a Newborn CRD-NRG-1 $^{(-/-)}$ mice lack spontaneous movement and are cyanotic. b,b' Whole-mount in situ hybridization with CRD-specific probe of E11 CRD-NRG-1 $^{(+/-)}$ & $^{(-/-)}$ mice. N5g, trigeminal: N10g, vagal ganglia; sc, spinal cord; drg, dorsal root ganglia. c,c' Paraffin-section of PO lung stained with H&E. (c) asterisks indicate expanded alveoli in CRD-NRG-T $^{(+/-)}$ mice, (c') carets point to collapsed airspaces in CRD-NRG-1 $^{(-/-)}$ mice.

FIG. 21: Defective Neuromuscular Synaptogenesis in CRD-NRG-1 (–/–) mice.

(A) a,a' Immunofluorescence labeling (100X) of PO diaphragm with anti-neurofilament antibodies (red) or with b,b' anti-neurofilament antibodies (red) & α-bungarotoxin (αBgTx) (green). (a') arrows point to remnant neurofilament(+) staining in mutants, carets (b) and arrow (b') point to colocalization of neurofilament and αBgTx staining. c,c' Acetylcholinesterase staining (AChE) (400X) of PO diaphragm, (c) carets point to strong, aligned AChE staining in controls, (c¹) arrows point to weak, scattered AChE staining in mutant. d,d' H&E staining of fresh-frozen PO diaphragm muscle, (d) carets indicate eccentric, peripheral nuclei, (d') arrows point to central nuclei. (B) f,f Immunofluorescence with anti-neurofilament antibodies (red); e,e',g,g' anti-neurofilament and anti-synaptophysin antibodies (red) & αBgTx (green); h,h' anti-neurofilament antibodies (green) & anti-S100β antibody (red). (e,e') E18.5 intercostal muscle (400X), (e) asterisks point out overlap of neurofilament and αBgTx, (e') arrows indicate examples where staining does not overlap. f,f E14.5 diaphragm (100X). (f) asterisks indicate normal branching pattern of phrenic nerve and termination of intradiaphragmatic branches in central region of muscle, (f) arrows highlight defasciculated axons with irregular branching patterns, repeated neurite crossings, and aberrant extension to the most lateral edges of the diaphragm. g,g' E14.5 diaphragm (400X). (g) asterisks indicate the organized endplate zone where nerve terminals overlie clusters of αBgTx-labeled AChRs. (g') arrows indicate examples where synaptophysin & αBgTx do not overlap. Note, disorganized endplate zone with nerve terminals approaching AChRs from many directions and some nerve terminals passing over αBgTx staining h.h' E14.5 diaphragm (400X). arrows in (h) indicate S100β(+) cells along peripheral nerves absent in (h').

Figure 22A:
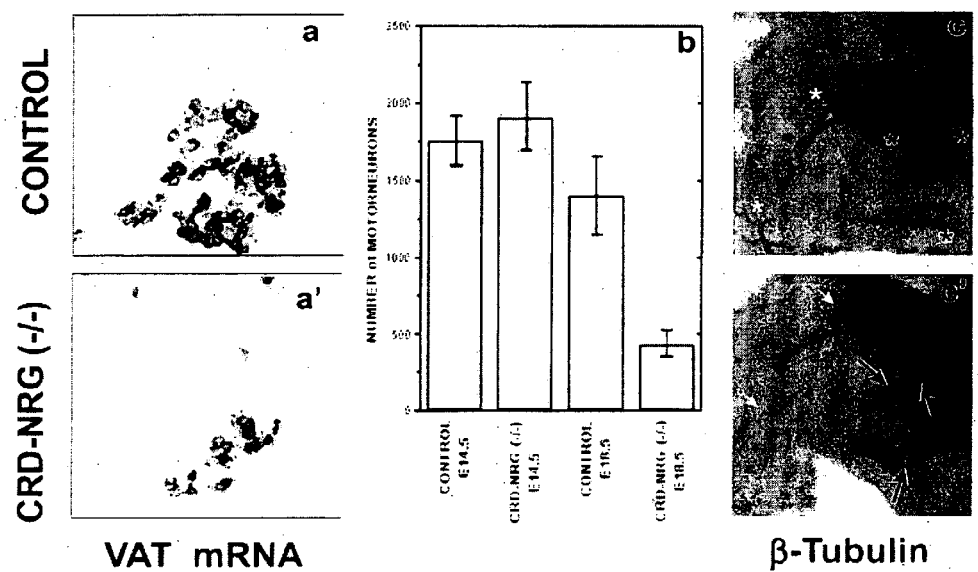
Figure 22B:
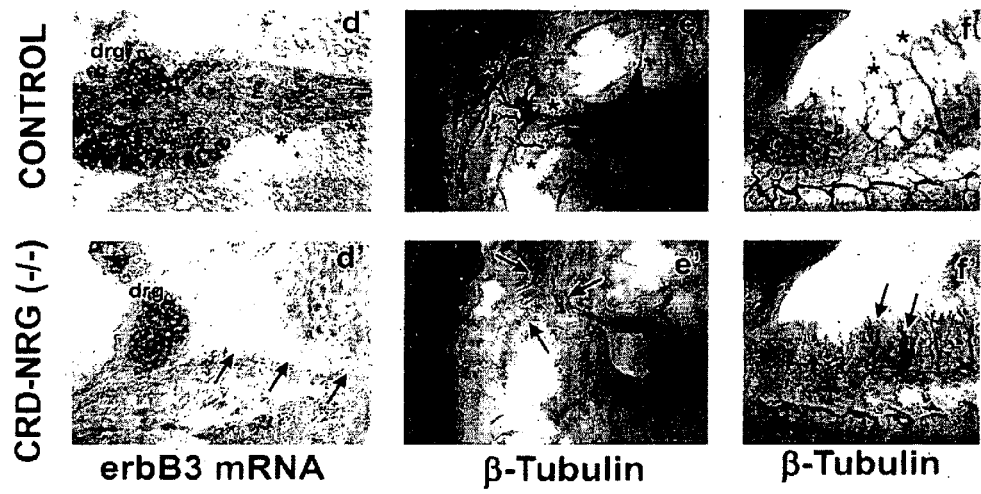
Figure 22C:
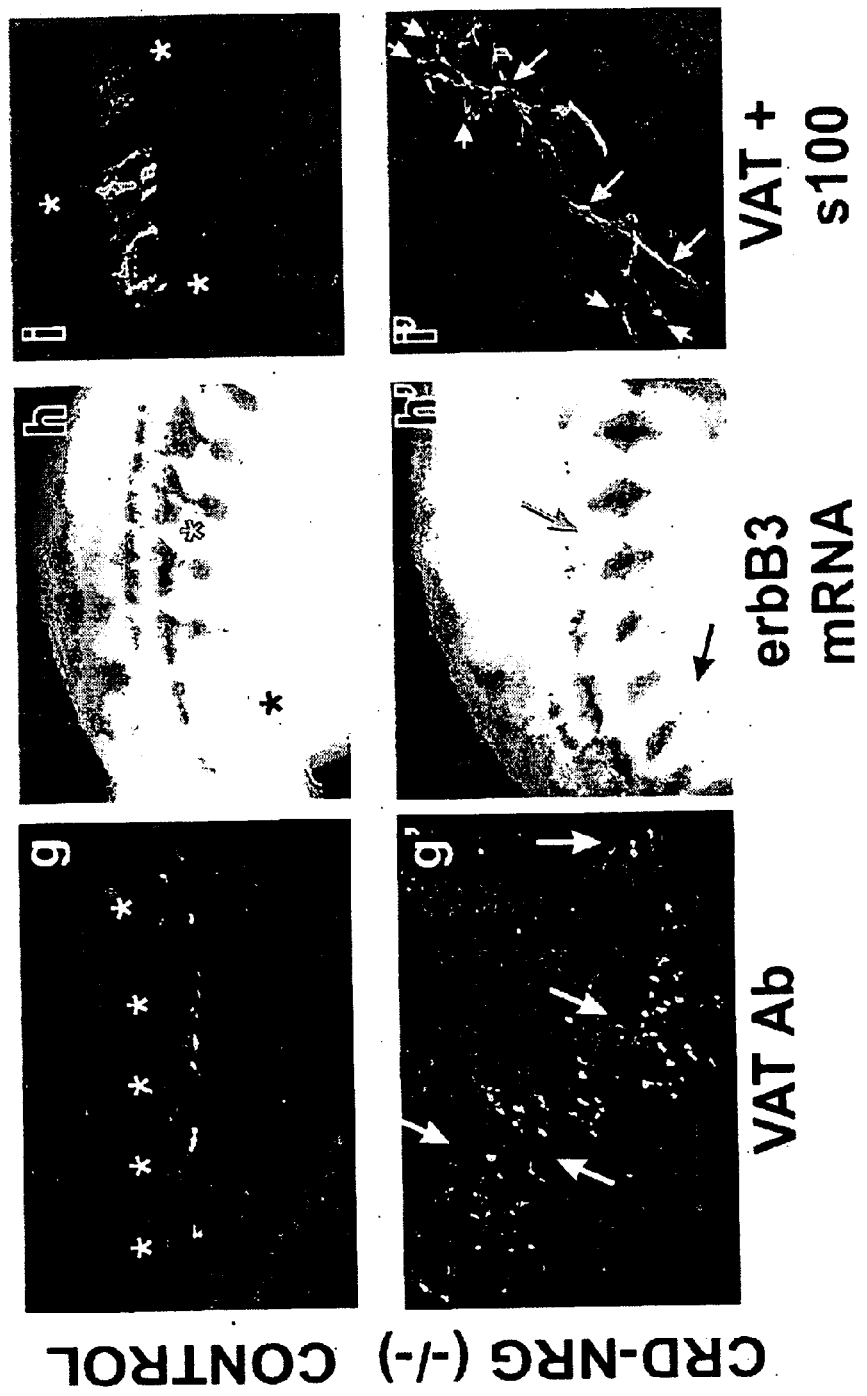

FIG. 22: Abnormal projections and subsequent degeneration of peripheral nerves in CRD-NRG-V $^{(-/-)}$ mice.

(A) a,a' In situ hybridization with vesicular ACh transporter (VAT)-specific probe of 10 µm sections through cervical enlargement of E18.5 spinal cord (200X). b Number of motor neurons present in spinal cord levels C1–C6 in control and mutant embryos (n=3 for each age and genotype). c,c' Whole-mount immunostaining of E12.5 limb with β-Tubulin III antibody (70X). (c) black and yellow asterisks show splayed nerve terminations of spinal nerves and cutaneous sensory projections in controls, respectively. (c') black and yellow arrows indicate bulbous, compact terminations of spinal nerves and cutaneous sensory projections in CRD-NRG-V $^{(-/-)}$ mice, respectively. (B) d,d' In situ hybridization with erbBS-specific probe of 10 µm sections through cervical enlargement of E18.5 spinal cord (200X). d asterisks indicate sensory root lined with erbB3(+) cells, d' arrows point to the sensory root that is devoid of erbB3(+) cells. e,e',f,f Whole-mount immunostaining of E12.5 embryos with β-Tubulin III antibody (70X); lmb, limb. (e,e') asterisks and arrows indicate the cervical sensory cutaneous projections. (f,f) asterisks and arrows point to trunk lateral cutaneous sensory branches. g,g' Immunofluorescence with anti-VAT antibodies of E18.5 hindlimb muscle (green) (200X). Asterisks (g) & arrows (g') arrows point to nerve terminals. h,h' Whole-mount in situ hybridization of E12 embryos with erbBS-specific probe (70X). (h) asterisks point to erb3(+) staining along peripheral nerves emanating from caudal spinal cord levels, (h') arrows point to peripheral nerves which show decreased erbB3(+)staining. Note that embryo in (h') is older than embryo in (h). i,i' Immunofluorescence with anti-neurofilament antibodies (green) & anti-S100β antibody (red) (400X). (i) asterisks indicate colocalization of neurofilament & S100β staining in nerve terminations of control, (i') yellow arrows point to colocalization of neurofilament and S100β along preterminal branches; white arrows point to nerve terminations devoid of S100β staining.

FIG. 23: Hindbrain Deficits and Loss of Schwann cell precursors in CRD-NRG-1$^{(-/-)}$ mice.

(A) a-b In situ hybridization of 10 μm transverse serial sections of trigeminal ganglion of E14.5 embryos, (a) CRD-NRG-1-specific probe (100X). (b) Pan-NRG-1-specific probe (100X). c-e In situ hybridization of 10 μm coronal serial sections of vibrissa follicles of E18.5 embryos, (c) CRD-specific probe (200X); (d) erbB5-specific probe (200X); (e) erbB4-specific probe (200X). f,g In situ hybridization of 10 μm coronal sections of E18.5 embryos with CRD-NRG-1-specific probe, (f) trigeminal motor nucleus (200X) (g) facial motor nucleus (200X). (B) h,h' Whole-mount immunostaining of E11 embryos (70X) with anti-p-tubulin III antibody, (h') Arrows indicate the onset of abnormal branching of cranial nerve projections N5n$_{man}$& N7n. N5g, trigeminal; N7g/N8g, vestibulo-cochlear; N9g, petrosal; N10g, nodose ganglia; op, opthalmic, max, maxillary, man, mandibular branches of N5n, trigeminal nerve; N7n, facial; N10n, vagus; N11n, spinal accessory; N12n, hypoglossal nerve; C1,C2 cervical dorsal root ganglion and cervical spinal cord projections. i,i' In situ hybridization with erbB5-specific probe of trigeminal ganglion of E14.5 embryos, (i) asterisks indicate peripheral projections lined with erbB3(+) cells. T-bar indicates the width of nerve (100X). (i') arrows point to the peripheral nerve projection in mutants (100X). (j,j') Whole-mount in situ hybridization with erbB5-specific probe of E12 embryos (70X). (j) black and green arrows point to erbB5-positive cells along N11n and its convergence with N10n and along peripheral nerve projections of cervical dorsal root ganglia, respectively. White arrows point to erbB3(+)positive cells in developing muscle, (j') black and green arrows point to the dramatic loss of erbB3(+)-staining along N11n, the coalescence of N10n, and along the projections of cervical dorsal root ganglia, respectively. White arrowhead points to the remaining erbB5 staining in developing muscle in CRD-NRG-$^{(-/-)}$ mice. k,k',l,l' In situ hybridization of E18.5 coronal sections through hindbrain with a vesicular ACh transporter (VAT)-specific probe. Note the reduction in size of facial motor nucleus (50X) (k vs k') and of trigeminal motor nucleus (200X) (I vs I') and abnormal cell migration (arrows, k') in CRD-NRG-1 $^{(-/-)}$ mice. Aq, aqueduct of IVth ventricle, m, midline, LOT, lateral dorsal tegmenal nucleus; PBr, parabrachial nucleus; N6n, abducens nucleus; N7n, facial nucleus. Dotted line in k,k' indicates the midline, m.

DETAILED DESCRIPTION OF THE INVENTION

This invention provides an isolated nucleic acid molecule encoding nARIA. This nucleic acid molecule may encode human nARIA (hnARIA), wherein the nucleic acid comprises the sequence shown from base 93 to base 758 of FIG. 3 (SEQ ID NO: 3). This invention also provides for an isolated nucleic acid molecule encoding nARIA, wherein the nucleic acid molecule encodes chicken nARIA (cnARIA) which comprises the sequence shown from base 608 to base 1234 of FIG. 1 (SEQ ID NO: 1). The nucleic acid molecule may be DNA, cDNA or RNA. The isolated nucleic acid molecule encoding nARIA includes nucleic acids encoding functionally equivalent variants or mutants of nARIA including nucleic acid molecules which, due to the degeneracy of the genetic code, code for nARIA polypeptide such as the polypeptide shown in FIGS. 2 (SEQ ID NO: 2) and 4 (SEQ ID NO: 4).

The isolated nucleic acid molecule encoding nARIA includes nucleic acids encoding biologically active variants of nARIA. This includes nucleic acid molecules which are capable of specifically hybridizing with an nARIA sequence. Biologically active variants may include nucleic acids variants which have at least 75% amino acid sequence identity with an nARIA sequence, more preferably at least 80%, even more preferably at least 90% and most preferably at least 95%. Identity or homology with respect to an nARIA sequence is defined herein as the percentage of amino acid residues in the candidate sequence that are identical with nARIA residues in FIGS. 2 (SEQ ID NO: 2) and 4 (SEQ ID NO: 4), after aligning the sequences and introducing gaps, if necessary, to achieve the maximum percent homology, and not considering any conservative substitutions to be identical residues. None of N-terminal, C-terminal or internal extensions, deletions, or insertions into nARIA sequence shall be construed as affecting homology. The isolated nucleic acid molecule encoding nARIA also includes any splice variants having nARIA biological activity as defined hereinafter.

As used herein, the purified nARIA polypeptide includes biologically active nARIA polypeptides which include each expressed or processed nARIA sequence, fragments thereof having a unique consecutive sequence of at least 5, 10, 15, 20, 25, 30 or 40 amino acids residue as shown in the underlined regions in FIGS. 2 (SEQ ID. NO: 2) and 4 (SEQ ID. NO: 4). Biologically active amino acids residue has been inserted N- or C-terminal to, or within the nARIA sequence. Amino acid sequence variants include nARIA wherein an amino acid residue has been replaced by another residue, nARIA polypeptides including those containing predetermined mutations by, e.g. site-directed or PCR mutagenesis. nARIA includes nARIA from such species as rabbit, rat, porcine, non-human primate, Drosophila, equine, murine, opine, human and chicken and alleles or other naturally occurring variants of the foregoing; derivatives of nARIA wherein it has been covalently modified by substitution, chemical, enzymatic or other appropriate means with a moiety such as an enzyme or radioisotopes. nARIA may be labeled with a detectable moiety including a fluorescent label, a biotin, a digozigenin, a radioactive aton, a paramagnetic ion, and a chemiluminescent abel. This invention also provides for glycosylaion variants of nARIA (as in the insertion of a glycosylation site or deletion of any glycosylation site by deletion insertion or substitution of an appropriate residue); and soluble forms of nARIA, such as nARIA which lacks a functional transmembrane domain.

As used herein, the purified nARIA polypeptide includes amino acid variants of nARIA which are prepared by introducing appropriate nucleotide changes into nARIA nucleic acid or by in vitro synthesis of the desired nARIA polypeptide. Such variants include, for example, deletions from, or insertions or substitutions of, residus within the amino acid sequence shown for human nARIA sequence. Any combination of deletions, insertion, and substitution of, residues within the amino acid sequence shown for human nARIA sequence. Any combination of deletions, insertion, and substitution can be made to arrive at the final construct possesses the desired characteristics. The amino acid changes also may alter post-translational modifications of nARIA, such as changes in the glycosylation sites, altering the membrane anchoring characteristics, altering the location of nARIA by inserting, deleting or otherwise affecting the transmembrane sequence of native nARIA or modifying its susceptibility to proteolytic cleavage.

This invention also provides for fusion proteins which contain nARIA polypeptide linked to an unrelated protein domain(s). The fusion proteins may be created by the insertion of amino- and/or carboxyl-terminal fusions ranging in length from one residue to polypeptides containing a hundred or more residues, as well as intrasequence insertions of single or multiple amino acid residues. Intrasequence insertions (i.e. insertions within the nARIA sequence) may range generally from about 1 to 10 residues, or preferably 1 to 5, and most preferably 1 to 3. Examples of terminal insertions include nARIA with an N-terminal methionyl residue (an artifact of the direct expression of nARIA in bacterial recombinant cell culture), and fusion of a heterologous N-terminal signal sequence to the N-terminus of nARIA to facilitate the secretion of mature nARIA from recombinant host cells. Such signal sequences generally will be obtained from, and thus be homologous to, the intended host cell species. Suitable sequences include STII or 1 pp for E. coli, alpha factor for yeast, and viral signals such as herpes gD for mammalian cells.

Other insertional variants of nARIA may include the fusion of the N- or C-terminus to an immunogenic polypeptide, e.g., bacterial polypeptides such as beta-lactamase or an enzyme encoded by the E. coli trp locus, or yeast protein, bovine serum albumin, or chemotactic polypeptides.

As used herein, the purified nARIA polypeptide includes amino acid substitution variants. These variants have at least one amino acid residue in the nARIA molecule removed and a different residue insert in its place. The sites of greatest interest for substitutional mutagenesis include a site(s) identified as an active site(s) of nARIA, and sites where the amino acids found in nARIA ligands from various species are substantially different in terms of side-chain bulk, charge, and/or hydrophobicity.

The amino terminus region of the cytoplasmic region of the nARIA may be fused to the carboxy terminus of heterologous transmembrane domains and receptors, to form a fusion polypeptide useful for intracellular signalling of a ligand binding to the heterologous receptor.

Other sites of interest are those in which particular residues of nARIA-like ligands obtained from various species are identical. These positions may be important for the biological activity of nARIA. These sites, especially those falling within a sequence of at least three other identically conserved sites, are substituted in a relatively conservative manner. Such conservative substitutions may be known as "preferred substitutions" and may include: valine substituted for alanine; lysine for arginine; glutamine for asparagine; glutamate for aspartate; serine for cysteine; asparagine for glutamine, aspartate for glutamate; proline for glycine; arginine for histidine; leucine for isoleucine; arginine for lysine; leucine for methionine, leucine for phenylalanine; glycine for proline, threonine for serine; serine for threonine; tyrosine for tryptophan; phenylalanine for tyrosine and leucine for valine.

Substantial modifications in function or immunological identity of nARIA are accomplished by selecting substitutions that differ significantly in their effect on maintaining (a) the structure of the polypeptide backbone in the area of the substitution, for example as a sheet or helical conformation, (b) the charge or hydrophobicity of the molecule at the target site, or (c) the bulk of the side-chain. Naturally occurring residues are divided into groups based on common side chain properties: hydrophobic; neutral hydrophilic; acidic; basic; residues that influence chain orientation and aromatic. Non-conservative substitutions will entail exchanging a member of one of these classes for another. Such substituted residues may be introduced into regions of nARIA that are homologous with other receptor ligands, or, more preferably, into the non-homologous regions of the molecule.

This invention provides for the creation of a combinatorial library of potential nARIA homologs which can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see Sambrook, et al., 1989; U.S. Pat. Nos. 5,223,409; 5,198,346 and 5,096,815. The purpose of making such a library is to provide in one mixture, all of the sequences encoding the desired set of potential nARIA sequences. This mixture could then be used for seletion of particular affinities, binding properties and separate functionalities.

This invention also provides for a replicable vector which contains nARIA sequence and a host cell containing this vector. This expression vector may be a prokaryotic expression vector, a eukaryotic expression vector, a mammalian expression vector, a yeast expression vector, a baculovirus expression vector or an insect expression vector. Examples of these vectors include PKK233-2, pEUK-C1, pREP4, pBlueBacHisA, pYES2, PSE280 or pEBVHis. Methods for the utilization of these replicable vectors may be found in Sambrook, et al., 1989 or in Kriegler 1990. The host cell may be a eukaryotic cell, a somatic cell, a germ cell, a neuronal cell, a myocyte, a mammary carcinoma cell, a lung cell, a prokaryotic cell, a virus packaging cell, or a stem cell.

This invention also provides for a purified polypeptide or an isolated polypeptide encoding nARIA. This polypeptide may encode human nARIA protein which includes the sequence shown from amino acid 31 to amino acid 252 of FIG. 4 (SEQ ID NO: 4). This polypeptide may also encode chicken nARIA protein which includes the sequence shown from amino acid 203 to amino acid 421 of FIG. 2 (SEQ ID NO: 2). This invention provides for the genomic sequence of human nARIA and chicken nARIA. This invention provides for functionally equivalent variants or mutants of nARIA including polypeptides which contain replacement amino acids which do not affect the functionality of the polypeptide. These variants may be prepared using in vitro mutagenesis techniques, polymerase chain reaction mutagenesis, or site-directed mutagenesis. The invention also provides for nARIA derivatives in vitro which are immobilized on a support for purposes of diagnoses, purification of nARIA binding factors or affinity purification of nARIA antibodies.

According to the present invention, nARIA or neuronal Acetylcholine Receptor Inducing Activity possesses certain biological activities. As used herein, nARIA has the ability to increase both nAChR currents and nAChR subunit gene expression in LSG neurons. The sequence of nARIA is unique throughout the N-terminal portion of the sequence, lacking the Ig-like domain typically upstream of the EGF-like domain in ARIA. nARIA retains the juxtamembrane EGF-like domain, shown to be sufficient for receptor binding and activation of receptor tyrosine kinase activity. Expression of nARIA by Northern blot analysis begins at E4 and is maximal at E8, while expression of ARIA begins at E6 and peaks at EB in the chick embryo. In cultured E11 chick sympathetic neurons treated with cultured media from COS cells transiently transfected with either ARIA or nARIA, an assay of both acetylcholine (ACh) gated currents and subunit mRNA levels was performed. These assays demonstrated differential regulation of nAChRs by nARIA vs ARIA. Specifically, nARIA significantly increased the maximal responses to 500 mM ACh whereas ARIA significantly decreased the maximal responses compared to cultures treated with recombinant protein from the antisense construct. Measurement of nAChR subunit mRNA levels in E9 sympathetic neurons treated with nARIA or ARIA with quantitative RT-PCR revealed different profiles of subunit gene regulation. A 24 hour treatment with nARIA mimicked the effects of innervation, up-regulating α3, α5, α7 and β4 levels, whereas ARIA downregulated β4 and α3. nARIA, therefore, may participate in the increase in nAChR subunit transcription induced by innervation of embryonic sympathetic neurons in vivo during sympathetic neuronal development.

nARIA, as discussed herein, not only has a unique n-terminal region but also displays biological activity distinct from ARIA. Tales I, II and III in the Experimental Details section herein describe these distinctions. nARIA, unlike ARIA, is specifically expressed only in nervous tissue, whereas ARIA can be expressed in other tissues. nARIA expression is higher in the spinal cord and cerebellum than in the forebrain and optic tectum. nARIA expression is first detected at stage E4 in the spinal cord, and expression is first detected in the cerebellum at stage E8. In all E11 sympathetic neurons, nARIA specifically has an effect on ligand gated channels: in response to acetylcholine, nARIA specifically increases the number of functional acetylcholine receptors as indicated by an increase in response to maximal concentrations of acetylcholine. nARIA has little effect on the number of GABA activated channels as indicated by the response to maximal concentrations of GABA. In contrast, at E11, ARIA has little effect on acetylcholine evoked responses and may upregulate GABA evoked responses. The effects of nARIA and ARIA on the acetylcholine evoked responses indicates that nARIA has been quantitated at E9 and is about 15 times more potent than ARIA.

nARIA increases the transcription of the α3 subunit of nAChR in sympathetic neurons. nARIA also increases α5, α3, α7 and β4 subunit gene expression of nAChR.

This invention provides for a method of inducing the expression of a specific nicotinic acetylcholine receptor subunit isoform. AChRs at mature mammalian neuromuscular junctions are pentameric protein complexes composed of four subunits in the ratio of $α_2βεδ$ (Mishina et al 1986). Most, if not all, of embryonic AChRs contain a different subunit, termed "τ" in place of the ε subunit. When mixtures of α,β,δ and τ subunit mRNAs are injected into *Xenopus* oocytes, the expressed channels have the properties of embryonic receptors. It is likely that this change in subunit composition is due to a change in gene expression and accounts for the switch in properties of Ach-activated channels from slow channels to fast channels. This invention provides for the application of nARIA alone or in combination with another agent to neural cells to induce the expression of subunit isoforms.

This invention further provides for nARIA antagonists which are capable of reducing the biological activity of nARIA. This antagonist may be proteinaceous such as an antibody specific for nARIA as described herein, a nucleic acid such as an antisense molecule to the nARIA mRNA as described herein, an enzymatic activity such as a ribozyme directed to nARIA mRNA as described herein or a protease specific for the nARIA polypeptide. The antagonist may also be an agent which is capable of binding the nARIA receptor with higher affinity than nARIA, thus competing away the effects of nARIA binding.

The subject invention also provides for nARIA agonist(s) which would be capable of enhancing the biological activity of nARIA. Such agonists may include other neurotrophic factors such as ciliary neurotrophic factor (see U.S. Pat. No. 4,997,929); nerve growth factor (see U.S. Pat. No. 5,169,762); neurotrophic factor 4/5. (see PCT International Publication No. WO 92/05254); brain-derived neurotrophic factor (see U.S. Pat. No. 5,180,820); glial-derived neurotrophic factor (see PCT International Publication No. WO 93/06116) or any other neurotrophic factor (see European application EP 0 386 752 A1). The disclosures of these publications in their entireties are hereby incorporated by reference into this application in order to more fully describe the state of the art as known to those skilled therein as of the date of the invention described and claimed herein.

This invention also provides for an antibody immunoreactive with an epitope comprising a unique sequence shown in either FIG. 2 (SEQ ID NO: 2) from amino acid 203 to amino acid 421 or in FIG. 4 (SEQ ID NO: 4) from amino acid 31 to amino acid 252.

A further embodiment of the invention is a monoclonal antibody which is specific for nARIA. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. Also, they may be used to remove nARIA from the serum. A second advantage of monoclonal antibodies is that they can be synthesized by hybridoma cells in culture, uncontaminated by other immunoglobins. Monoclonal antibodies may be prepared from supernatants of cultured hybridoma cells or from ascites induced by intraperitoneal inoculation of hybridoma cells into mice. The hybridoma technique described originally by Köhler and Milstein, 1976, has been widely applied to produce hybrid cell lines that secrete high levels of monoclonal antibodies against many specific antigens.

Another embodiment of this invention is a ribozyme which is capable of cleaving nARIA mRNA. See Cech, et al., U.S. Pat. No. 4,987,071; Altman et al., U.S. Pat. No. 5,168,053; Haseloff et al, U.S. Pat. No. 5,254,678 published European application No. Hampel et al., EP 360,257.

This invention provides for a nucleic acid comprising a unique nARIA sequence in a 3' to 5' orientation, antisense to at least a portion of a gene encoding naturally occurring nARIA. This antisense nucleic acid molecule may be labeled with a detectable moiety selected from the group consisting of a fluorescent label, a biotin, a digoxigenin, a radioactive atom, a paramagnetic ion, and a chemiluminescent label. See Inoue et al. U.S. Pat. Nos. 5,208,149 and 5,190,931 and Schewmaker, U.S. Pat. No. 5,107,065.

Labeling of a circular oligonucleotide (such as a replicable vector as described herein) can be done by incorporating nucleotides linked to a "reporter molecule" into the subject circular oligonucleotides. A "reporter molecule", as defined herein, is a molecule or atom which, by its chemical nature, provides an identifiable signal allowing detection of the circular oligonucleotide. Detection can be either qualitative or quantitative. The present invention contemplates using any commonly used reporter molecule including radionucleotides, enzymes, biotins, psoralens, fluorophores, chelated heavy metals, and luciferin. The most commonly used reporter molecules are either enzymes, fluorophores, or radionucleotides linked to the nucleotides which are used in circular oligonucleotide synthesis. Commonly used enzymes include horseradish peroxidase, alkaline phosphatase, glucose oxidase and α-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1.2-phenylenediamine, 5-aminosalicylic acid or toluidine are commonly used. The probes so generated have utility in the detection of a specific nARIA DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al, 1989. This invention also provides a method of amplifying a nucleic acid sample comprising priming a nucleic acid polymerase chain reaction with nucleic acid (DNA or RNA) encoding (or complementary to) an nARIA.

Another embodiment of this invention is the normal expression or overexpression of nARIA ex vivo in human neuronal cells, stem cells or undifferentiated nerve cells and muscle cells. These cells may be utilized for gene therapy in patients (See Anderson et al U.S. Pat. No. 5,399,346).

This invention further provides for a transgenic nonhuman mammal whose germ or somatic cells contain a nucleic acid molecule which encodes nARIA polypeptide or biologically active variants thereof, introduced into the mammal, or an ancestor thereof, at an embryonic stage. This invention provides for a transgenic nonhuman mammal whose cells may be transfected with a suitable vector with an appropriate sequence designed to reduce expression levels of nARIA polypeptide below the expression levels of that of a native mammal. The transgenic nonhuman mammal may be transfected with a suitable vector which contains an appropriate piece of genomic clone designed for homologous recombination. Alternatively, the transgenic nonhuman mammal may be transfected with a suitable vector which encodes an appropriate ribozyme or antisense molecule. See for example, Leder and Stewart, U.S. Pat. No. 4,736,866 for methods for the production of a transgenic mouse.

Biologically functional variants of nARIA are nucleic acid molecules that, due to the degeneracy of the genetic code, code on expression for nARIA polypeptide. The foregoing variant DNA sequences may be translated into variant nARIA polypeptides which display the biological activity of an nARIA polypeptide. These variant nucleic acid molecules may also be expressed in this transgenic mammal. Active variants should hybridize to the wild-type nARIA nucleic acid sequence under highly stringent or moderately stringent conditions (Sambrook et al, 1989).

One embodiment of this invention is a method for inducing the formation of a synaptic junction between a neuron and a target cell, which includes treating the target cell with nARIA polypeptide or nARIA nucleic acid molecule encoding nARIA or a biologically active variant thereof, in an amount sufficient to induce the formation of a synaptic junction. A "sufficient amount" as used herein refers to that amount which provides a therapeutic effect for a given condition and administration regimen. The target cell may be a somatic cell such as a myocyte, a neuronal cell, a glandular cell or any postsynaptic cell. This method provides for the induction of the formation of a synaptic junction in an individual having a neurological disorder involving abnormal synaptic connections. Isolated nARIA may be used as a growth factor for in vitro cell culture or in vivo to promote the growth of cells.

nARIA, nARIA agonists or nARIA antagonists may be used to treat any disease where levels of nARIA metabolism are changed and therefore ion channel levels or activities are not normal as in some neurological disorders. Such disorders would include any disease with an abnormal production of nARIA. Neurological disorders that affect the central nervous system, memory or cognitive functions may also be treated with nARIA. Such disorders may be the result of the normal aging process or the result of damage to the nervous system by trauma, surgery, ischemia, infection or metabolic disease. Such disorders may also include Alzheimer's Disease, Turret's Syndrome, and Parkinson's Disease. These diseases have been shown to respond to nicotine treatment.

The neurological disorder may be a neuromuscular disorder. Examples of neuromuscular disorders which may be treatable with nARIA include Alzheimer's disease, myasthenia gravis, Huntington's disease, Pick's disease, Parkinson's disease, and Turret's Syndrome. Also included are neurogenic and myopathic diseases including chronic atrophies such as amyotrophic lateral sclerosis, Guillain-Barre syndrome, progressive bulbar palsies, spinal muscular atrophies and chronic peripheral neuropathy. Autonomic disorders of the peripheral nervous system may also be included in this treatment which include disorders that affect the innervation of muscle or endocrine tissue such as tachycardia, atrial cardiac arrhythmias and hypertension. These disorders are thought to be associated with an abnormally low level of muscarinic AChRs in the striated muscle.

This invention provides for a method of altering neuro-receptor expression. In this method, nARIA is administered to a subject which may result in a change in the expression of neuro-receptors. The method of administration of nARIA is described more fully hereinafter.

This invention provides for the production of functional mammalian nARIA protein in a prokaryotic expression system, a mammalian expression system, a baculovirus expression system, an insect expression system or a yeast expression system. This production may provide for the post-translational modifications which exist in the naturally occurring nARIA protein. For protocols describing bacterial expression of mammalian proteins, see Sambrook et al, 1989.

Another embodiment of this invention is a method for inducing neuronal regeneration which comprises contacting a target cell with a composition of nARIA and a pharmaceutically acceptable carrier to induce the formation of a synaptic junction between a neuron and a target cell. The target cell may be a neuronal cell, an endocrine cell, a muscle cell or any cell capable of forming a neuro-muscular junction. nARIA may be used to facilitate incorporation of implants into nervous tissue or to promote nerve regeneration following damage by trauma, infarction, infection or postoperatively.

This invention provides for a combination therapy of nARIA with another neurotropic factor or cytokine or growth factor or with other agents known for use in the treatment of malignancies. Such factors may include transforming growth factor beta (TGF-β), ciliary neurotropic factor (CNTF), brain derived neurotropic factor (BDNF), NT-4, NT-5, NT-4/5, nerve growth factor (NGF), activins, agrin, cell differentiation factor (CDF), glial growth factor (GGF), and neu differentiation factor (NDF), ARIA, and heregulins. nARIA may be administered in combination with agrin for effects on the neuromuscular junction. For therapy directed toward the autonomic/enteric nervous system, TGF-β and nARIA is the preferred combination. For therapy directed to the central nervous system, nARIA and CDF is the preferred combination.

When administered parenterally, proteins are often cleared rapidly from the circulation and may therefore elicit relatively short-lived pharmacological activity. Consequently, frequent injections of relatively large doses of bioactive proteins may by required to sustain therapeutic efficacy. Proteins modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified proteins (Abuchowski et al., 1981; Newmark et al., 1982; and Katre et al., 1987). Such modifications may also increase the protein's solubility in aqueous solution, eliminate aggregation, enhance the physical and chemical stability of the protein, and greatly reduce the immunogenicity and antigenicity of the protein. As a result, the desired in vivo biological activity may be achieved by the administration of such polymer-protein adducts less frequently or in lower doses than with the unmodified protein. nARIA compositions may be administered parenterally by injection or directly into the cerebral spinal fluid by continuous infusion from an implanted pump. nARIA may also be administered with one or more agents capable of promoting penetration of nARIA across the blood-brain barrier.

Attachment of polyethylene glycol (PEG) to proteins is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous proteins. For example, a PEG adduct of a human protein might be useful for the treatment of disease in other mammalian species without the risk of triggering a severe immune response. nARIA or cells that produce nARIA may be delivered in a microencapsulation devise so as to reduce or prevent an host immune response against the nARIA producing cells. nARIA may also be delivered microencapsulated in a membrane, such as a liposome.

Polymers such as PEG may be conveniently attached to one or more reactive amino acid residues in a protein such as the alpha-amino group of the aminoterminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Another embodiment of this invention is a method for determining a prognosis of or diagnosing a neoplastic condition in a subject. In this method, one may obtain a biological sample from the subject, and contact the sample with a reagent capable of binding to an element in the sample, the element being an nARIA nucleic acid molecule or polypeptide encoding nARIA, under conditions such that the reagent binds only if the element is present in the sample. One may then detect the presence of the reagent bound to the element and thereby determine the prognosis of the neoplastic condition of the subject. The reagent may be an oligonucleotide capable of hybridizing with a nucleic acid encoding nARIA polypeptide under standard stringency hybridization conditions. The reagent in this method may be an antibody specific for nARIA polypeptide. The element in the biological sample may be a nucleic acid molecule encoding nARIA or a polypeptide encoding nARIA protein. The biological sample may be cerebrospinal fluid, blood, plasma, ascites fluid, tissue, urine, sputum, amniotic fluid, saliva, lung lavage, or cell extracts. This method may be performed with the reagent is affixed to a solid support. The neoplastic condition may be a mammary neoplasm or a small cell carcinoma of the lung.

A further embodiment of this invention is a method for the treatment of a neoplastic condition of a subject. In this method a pharmaceutically acceptable form of nARIA in a sufficient amount over a sufficient time period is administered to a subject to induce differentiation of neoplastic cells and thus treat the neoplastic condition. The composition may be a form of nARIA such as nARIA polypeptide or nARIA nucleic acid, combined with a pharmaceutically acceptable carrier. The carrier may be made up of suitable diluents, preservatives, solubilizers, emulsifiers, or adjuvants and may be in an aerosol, intravenous, oral or topical form.

Also provided by the invention are pharmaceutical compositions comprising therapeutically effective amounts of polypeptide products of the invention together with suitable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of nARIA. The choice of compositions will depend on the physical and chemical properties of the protein having nARIA activity. For example, a product derived from a membrane-bound form of nARIA may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and nARIA coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional. nARIA may be part of a pharmaceutical composition with agrin and an acceptable carrier to recapitulate both the induction of expression of AChR and the clustering of the AChR's on the membrane surface.

Polypeptides of the invention may be "labeled" by association with a detectable marker substance (e.g., radiolabeled or biotinylated) to provide reagents useful in detection and quantification of nARIA or its receptor bearing cells in solid tissue and fluid samples such as blood or urine.

Another embodiment of this invention is a method for determining whether a compound is capable of modulating the binding of an nARIA polypeptide to its receptor. In this method, the compound may be incubated under suitable conditions with an appropriate nARIA polypeptide-affinity derivative or receptor-affinity derivative under appropriate conditions such that an affinity complex may form. Then, one may measure the amount of affinity complex formed so as to determine whether the compound is capable of modulating the binding of the nARIA polypeptide to its receptor. The affinity complex may be an nARIA receptor bound to an affinity derivative or an nARIA polypeptide bound to a derivative. The measurement in this method may comprise binding of an antibody specific for nARIA to the affinity complex to measure the amount of affinity complex formed. The affinity derivative may be sepharose, cellulose, plastic, glass, latex, glass beads, a nylon membrane, a cellulose acetate membrane, an epoxy-activated synthetic copolymer membrane, a nitrocellulose membrane or a streptavidin-coated plastic.

The present invention provides an assay for diagnosing whether a subject has or is predisposed to developing a neoplastic disease which comprises: a) obtaining a biological sample from the subject; b) contacting the sample with an agent that detects the presence of an extracellular domain of nARIA (CRD-neuregulin) or an isoform thereof; c) measuring the amount of agent bound by the sample; d) comparing the amount of agent bound measured in step c) with the amount of agent bound by a standard normal sample, a higher amount bound by the sample from the subject being indicative of the subject having or being predisposed to developing a neoplastic disease.

The present invention also provides assay for determining whether a subject has a neurodegenerative disease which comprises: a) obtaining a biological sample from the subject; b) contacting the sample with an agent that detects the presence of an extracellular domain of nARIA (CRD-neuregulin) or an agent which detects the presence of soluble neuregulin receptor; c) measuring the amount of agent bound by the sample; d) comparing the amount of bound agent measured in step c) with the amount of agent bound by a standard normal sample, a higher amount or a lower amount bound by the sample from the subject being indicative of the subject having a neurodegenerative disease.

In one embodiment, the agent is an antibody or a fragment thereof. In another embodiment, the sample is cerebrospinal fluid (CSF), blood, plasma, sputum, amniotic fluid, ascites fluid, breast aspirate, saliva, urine, lung lavage, or cell lysate or extract derived from a biopsy. In a further embodiment, the agent is an antibody which binds to an epitope formed by the amino acid sequence shown in FIG. 2 (SEQ ID NO: 2) or FIG. 4 (SEQ ID NO: 4). In another embodiment, the agent is an antibody which binds to an epitope of the cytoplasmic domain of nARIA. In another embodiment, the agent is an antibody which specifically binds to the amino acid sequence NQDPIAV (SEQ ID NO: 5). In a further embodiment, the neoplastic disease is breast cancer, prostate cancer, a brain cancer or ovarian cancer. In another embodiment, the neurodegenerative disease is Alzheimer's Disease, Parkinson's Disease, Turrets Syndrome, Amyotrophic lateral Sclerosis, Pick's Disease, Myasthenia Gravis, or Senility.

The present invention also provides a method for maintaining or sustaining a synaptic connection between a neuron and a target cell comprising contacting the target cell with an nARIA polypeptide or a nucleic acid molecule encoding nARIA or biologically active variant thereof, in an amount sufficient to maintain the synaptic junction.

In one embodiment, the target cell is a somatic cell including a myocyte, a neuronal cell, a glandular cell or any postsynaptic cell. In another embodiment, maintenance of the synaptic junction is accomplished in an individual having a neurological disorder involving abnormal synaptic connections. In another embodiment, the neurological disorder is an neuromuscular disorder or a neurodegenerative disease. In a further embodiment, the nARIA polypeptide is NQDPIAV (Seq ID NO: 5) or the A-form of the cytoplasmic domain of nARIA. In a further embodiment, the neurological disorder is Alzheimer's Disease, Parkinson's Disease, Turrets Syndrome, Amyotrophic Lateral Sclerosis, Pick's Disease, Myasthenia Gravis, or Senility.

The present invention also provides a method for inducing neuronal regeneration which comprises contacting a target cell with a composition of nARIA and pharmaceutically acceptable carrier to induce the formation of a synaptic junction between a neuron and a target cell. In one embodiment, the target cell is a neuronal cell or a muscle cell.

The present invention also provides a method for the treatment of a neoplastic condition of a subject which comprises administering to the subject a pharmaceutically acceptable form of nARIA in a sufficient amount over a sufficient time period to induce differentiation of neuoplastic cells and thus treat the neoplastic condition.

The present invention also provides a method for determining whether a compound is capable of modulating the binding of an nARIA polypeptide to its receptor, which comprises: (a) incubating the compound under suitable conditions with an appropriate nARIA polypeptide-affinity derivative or receptor-affinity derivative under appropriate conditions such that an affinity complex may form; (b) measuring the amount of affinity complex formed so as to determine whether the compound is capable of modulating the binding of the nARIA polypeptide to is receptor.

In one embodiment, the affinity complex comprises an nARIA receptor bound to an affinity derivative. In another embodiment, the affinity complex comprises an nARIA polypeptide bound to an affinity derivative. In another embodiment, the measuring comprises binding of an antibody specific for nARIA to the affinity complex to measure the amount of affinity complex formed. In another embodiment, the affinity derivative comprises sepharose, cellulose, plastic, glass, glass beads, or a streptavidin-coated plastic.

The present invention also provides an assay for detecting neoplastic disease in a subject which comprises: a) obtaining a biological sample from the subject; b) contacting the sample with an agent that specifically binds to an expression product of a neuregulin gene or a neuregulin receptor; c) measuring the amount of agent bound by the sample; d) comparing the amount of agent bound measured in step c) with the amount of agent bound by a standard normal sample, a higher amount bound by the sample from the subject being indicative of the presence of neoplastic disease in the subject.

In one embodiment, the neuregulin receptor is erbB2, erbB3, or erbB4. In another embodiment, the agent specifically binds to an amino acid sequence of neuregulin which directs translocation to the nucleus. In another embodiment, an expression product of an neuregulin gene comprises a neuregulin protein, an extracellular domain of a neuregulin protein, a polypeptide encoded by the amino acid sequence shown in FIG. 2 (SEQ ID NO: 2) or 4 (SEQ ID NO: 4). In another embodiment, the agent is detectably labeled.

The present invention provides an assay for determining the amount of her 2 receptor in a bodily fluid from a subject and an assay for other heregulin receptors which comprises a) obtaining a bodily fluid from a subject or a sample from a subject (i.e. a brain punch biopsy, blood, serum, plasma, urine, etc.); b) contacting the sample with cells which are transfected with a reporter construct (the construct being CRD-neuregulin with a cytoplasmic tail whch has a detetable marker attached to it); c) measuring the detectable label in the nucleus of the cells and thereby determining the amount of her 2 receptor in the bodily fluid from the sample.

The neuregulin in the bodily fluid binds to a receptor on the surface of the transfected cell and there will be cleavage of the external domain and the cleavage of the internal cytoplasmic domain. The cytoplasmic domain will then be translocated into the nucleus and the detectable able will be available for detection in the nucleus. The detectable label may be green fluorescent protein or VP16.

Another assay which is provided for in the present invention is an assay which comprises obtaining a brain punch from a subject and performing immunohistochemistry on frozen sections or preserved sections of the tissue obtained using a detectably labeled antibody specific for the cytoplasmic domain of neuregulin and determining the percentage of nuclei that are showing label in the tissue sample.

The nuclear targeting domain of neuregulin may be found in Yang et al and begins at amino acid number 230 (KTKKQRKK).

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS

Example 1

Isolation and Sequence Analysis of nARIA

Novel members of the ARIA/NDF/heregulin family that would be expressed in neurons projecting to cholinoceptive neural targets were identified. Cloning efforts yielded 29 positives, including several which encoded variants with an entirely novel N-terminal sequence, distinguished by the absence of the usual Ig-like domains of the heregulin/NDF family. The predominance of the novel, Ig-less clones over the ARIA like clones was striking (11 vs 5 of 29 positives). We named the novel splice variant "nARIA" for neuronal nAChR Inducing Activity. All clones were isolated by two different and separate approaches as described below.

A different library was used in each screening protocol carried out to isolate and clone the nARIA gene. A chick E13 total brain cDNA library was screened with a rat DNA probe generated by PCR amplification. For the PCR amplification, degenerate primers corresponding to nucleotide sequences 523–542 (upper primer) and 1080–1100 (lower primer) of the published rat NDF sequence (Wen et al., 1992) were used to amplify a DNA fragment from a template of adult rat spinal cord cDNA. The upper and lower primers were within the immunoglobulin and transmembrane domains respectively. The amplified fragment was subcloned into the pCRII® vector (Invitrogen) and was sequenced, revealing an open reading frame. The predicted peptide encoded by this fragment contained the immunoglobulin to transmembrane domains of the heregulin β1 isoform and is distinct from the published NDF sequence, which is an α-isoform of heregulin. Screening of the cDNA library by random primed labeling of the amplified fragment resulted in three independent clones, of which only one contained a complete open reading frame. This open reading frame is 2055 nucleotides (FIG. 1 (SEQ ID NO: 1), nucleotides 608–2662) and encodes the nARIA transcript. The nucleotide sequences from base pair 1293 downstream to the poly-A tail of the nARIA clone are identical to ARIA a related cloned chicken gene (Falls et al., 1993).

On the protein level, identical sequences encode the portion of the molecule spanning from the EGF-like domain to the C-terminus in ARIA and nARIA. The break in homology occurs at a known splice site and the sequences upstream to the splice junction are unique to nARIA. Analysis of the predicted protein sequence did not produce a motif corresponding to an immunoglobulin domain. Instead, there was a cysteine rich region identified (8 cysteines in 34 amino acids). See FIG. 2 (SEQ ID NO: 2).

Example 2

Spatial and Temporal Expression of nARIA in Chick Development

A chick E5–E11 spinal cord cDNA library which we prepared was also screened. The probe for screening was generated by RT-PCR amplification from E8 chick spinal cord total RNA using primers corresponding to nucleotide sequences 264–281 (upper primer) and 1294–1313 (lower primer) of the published ARIA sequence (Falls, et al., 1993). The amplified PCR fragment was subcloned into a PGEM3Z vector and sequenced to confirm its identity. Screening of the chick E5–11 spinal cord primary cDNA library by random primed labeling using the PCR fragment as the template resulted in 26 clones. Of these, 11 contained the novel cysteine rich domain (nARIA like clones), 6 clones contained the immunoglobulin-like domain (ARIA like splice forms), while the remaining clones had unidentifiable sequences. The nARIA clones included 8 that were identical to the form obtained by the earlier screening and 3 additional isoforms that differed in the N-terminus, the EGF-like domain, the juxtamembrane linker, and/or the C-terminal region. The extracellular domains of these clones were fully sequenced and the intracellular portions were partially sequenced. Restriction mapping and Southern blotting were also used to confirm the relatedness of these molecules. A human cerebellar cDNA library was screened in the manner described above. This procedure resulted in the isolation of human nARIA (FIGS. 3 (SEQ ID NO: 3) & 4 (SEQ ID NO: 4)).

Multiple tissue Northern blots were screened with probes specific for unique domains of nARIA and were compared with those probed with an ARIA specific probe (FIG. 6). In particular, the ARIA probe detected ARIA in skeletal muscle (pectoral muscle) whereas expression of nARIA was found to be restricted to nervous tissue. The expression of nARIA represents a higher percentage of the total message in the cerebellum and spinal cord than in the forebrain or optic tectum. ARIA message is represented at a higher level in the forebrain and optic tectum than in the cerebellum and spinal cord (FIG. 7). The developmental expression patterns of nARIA and ARIA in spinal cord as detected by RT-PCR and Northern blot hybridization are different (FIGS. 8A–8B). The mRNA of nARIA is detectable by E3 and robust by E4 whereas initiation of ARIA and expression occurs later (E6–8) (FIGS. 9A–C).

In situ hybridization studies with probes specific for nARIA and ARIA (containing the cysteine rich domain or Ig-like domain respectively) also demonstrated different patterns of expression (FIGS. 10A–D). In particular, a positive signal is obtained in the presumptive preganglionic neurons with the nARIA probe but not with the ARIA probe. Therefore, the pattern of expression of ARIA and nARIA are different.

Example 3

Functional Analysis of Biological Activity—nARIA Activates Tyrosine Kinase Linked Receptor(s)

Initial experiments to characterize the functional properties of the nARIA protein focused upon the ability to activate protein tyrosine kinases. ARIA has been proposed to act, as other members of the NDF/heregulin family, through an interaction with specific tyrosine kinase-linked receptors (Falls, et al., 1993). This first step in transduction is assayed as tyrosine phosphorylation of a high molecular wight band, thought to represent phosphorylation of the receptor subunit(s). We examined the pattern of tyrosine phosphorylated proteins in extracts of lumbar sympathetic ganglia (LSG) neurons as well as several other cell lines with an anti-TYR-P antibody (4G10; UBI) (Ausubel et al., 1994; Falls, et al., 1993). Both recombinant ARIA an NARIA (from transiently transfected COS cells) induced time and dose dependent phosphorylation of 170–185 kD bands in the MCF7 and MDA-MB-453 cell lines (human carcinomas that overexpress erb-B2 receptor). ARIA appeared more potent than nARIA and somewhat less robust in phosphorylation of a 185 kD band in LSG. Differential effects of nARIA on glial cells and neurons differ from all other heregulin isoforms including ARIA, examined to date. nARIA's unique N-terminal sequence influences the binding of the isoform to the protein tyrosine kinase receptors thereby conferring distinct specificities.

Media conditioned by COS1 or HEK293 cells transiently transfected with the nARIA clone (sense configuration) activated tyrosine kinase activity in the breast tumor cell lines MCF7 or MDA-MB-453 above the basal levels of tyrosine kinase activity as determined by using the antisense configuration of nARIA. See FIGS. 11A–C. Furthermore, the levels of phosphorylation of the EGFR family members relative to one another was different between ARIA and nARIA. ARIA treatment resulted in a higher level of erB3/HER3 phosphorylation than nARIA. Treatment of acutely dispersed sympathetic neurons from E9 chicks with nARIA conditioned media resulted in increased tyrosine phosphorylation of an approximately 180 kD protein (FIG. 12).

Another assay to more clearly delineate between the biological activities of nARIA and ARIA involved the comparison of their effects on the expression of ligand-gated channels in primary neurons. These studies assayed the number of functional surface receptors for two transmitters (ACh and GABA) using an electrophysiological assay of transmitter gated macroscopic currents. The rationale for these experiments is based upon the pattern of expression of nARIA and ARIA, and on our previous studies of receptor regulation by spinal cord neurons (Role, 1988; Gardette et al, 1991). Treatment of primary cultures of sympathetic neurons from E11 chicks with recombinant nARIA for two days increased the magnitude of macroscopic currents activated by acetylcholine and appeared to decrease the currents gated by GABA (FIGS. 13A–D). In contrast, treatment with recombinant ARIA under the same conditions decreased the currents gated by acetylcholine and appeared to enhance GABA-evoked currents. The differential effects of nARIA vs ARIA on ACh gated currents, an index of the number of functional channels on the cell surface, was also reflected in the assays of the levels of expression of ACh receptor subunit encoding mRNA's.

Notably, a 24 hour treatment with recombinant nARIA increased the level of $\alpha 3$ subunit mRNA; in contrast, the level of $\alpha 3$ subunit mRNA was either slightly decreased or not altered by ARIA. The differential effect of nARIA and ARIA on transcription was not limited to the acetylcholine receptor subunits. Application of the differential display technique to primary cultures of sympathetic neurons treated for 24 hours with nARIA or ARIA suggested that the two growth factors differentially activate or suppress transcription of several distinct cDNAs.

The data presented herein suggests that the novel splice variant of the heregulin gene, nARIA may play a role in synaptic development that is unique from that of ARIA or other immunoglobulin-domain-containing splice variants. nARIA may potentially be used therapeutically or diagnostically. Alterations in the level of the production of nARIA may be indicative of a traumatic insult to the nervous system. Since the receptor for this factor is a known oncogene, changes in growth factor levels may be prognostic to some neoplastic conditions. Recombinant nARIA may be useful in cancer treatment regimens or for use in neuronal regeneration as described more fully herein. Other isoforms have been demonstrated to induce differentiation of breast tumor cell lines, promote survival of glial cells and increase the mitogenesis of some cell lines.

In has been demonstrated that the biological activity of nARIA is different than that of ARIA and is summarized in Table I. (The bold serves to highlight the differences in biological activity between ARIA and nARIA.)

TABLE I

Biological Activity and Effects of ARIA vs nARIA

| Biological Activities | ARIA | nARIA |
|---|---|---|
| Expression | Seen in chick nervous tissues and skeletal muscle Expression is higher in the forebrain and optic tectum than in the spinal cord and cerebellum | Seen only in nervous tissue at E13 Expression is higher in the spinal cord and cerebellum than in the forebrain and optic tectum |

TABLE I-continued

Biological Activity and Effects of ARIA vs nARIA

| Biological Activities | ARIA | nARIA |
|---|---|---|
| | Expression starts at E6 in the spinal cord | Expression starts at E4 in the spinal cord |
| | Expression starts at E8 in the cerebellum | Expression starts at E8 in the cerebellum |
| Activation of p185 phosphorylation | Seen in L6 rat myocytes | Seen in L6 rat myocytes |
| | Seen in PC12 cells (Fischbach, et al) | Not seen in PC12 cells |
| | Seen in sympathetic neurons | Seen in sympathetic neurons |
| | Seen in ciliary neurons (Fischbach, et al) | Not determined |
| | Seen in breast tumor cell lines MCF7 and MDA-MB-453 | Seen in breast tumor cell lines MCF7 and MDA-MB-453 |
| | Seen in rat O2A cells (Fischbach) | Not determined |
| Effects on ligand gated channels | Increases response to acetylcholine in E9 and decreases response in E11 sympathetic neurons | Increases response to acetylcholine in E9 and increases response in E11 sympathetic neurons |
| | Increases response to GABA in E9 and increases response in E11 sympathetic neurons. | Increases GABA responses in E9 and decreases responses in E11 sympathetic neurons |
| | Increases response to ACh in muscle cells (Fischbach et al.) | Not determined |
| Effects on transcription of nAChR subunits in rat medial habenula | No effect | Not determined |
| Effects on transcription of nAChR subunits in sympathetics | No effect on α3 Increases α5 and α7 | Increases α3 Increases α5 and α7 |
| Effects on sodium channel in muscle | Increases (Fischbach et al.) | Not determined |
| Effects on PC12 differentiation | Induces very short neurites in 10% of the cells (Fischbach et al.) | Not determined |
| | Reduces rate of replication by half (Fischbach et al.) | Not determined |
| Effects on glial cells | Increases the number of oligodendrocytes that develop from O2A precursors (Fischbach et al.) | Not determined |
| Effects on nAChR subunits in PC12 cells | "Like control" (Fischbach et al.) | Not determined |

Macroscopic, Single Channel and Synaptic Current Data Acquisition and Analysis

Single channel data acquisition and analysis was performed with an Axon Instruments system using Axobasic and PCLAMP 6.0 software. Additional programs were specifically designed for resolution of multiple channel classes of similar size and kinetics. Conductance, kinetics, NP0 and mean I analyses were performed as previously described (Listerud et al., 1991; Moss and Role, 1993; Moss et al., 1989; Simmons et al., 1988). Continuously recorded and evoked synaptic and macroscopic currents were stored on videotape and analyzed off line in software written in Axobasic.

An 80486 DX2-66 Mhz computer equipped with the Axobasic system was essential to all studies. The acquisition program sampled all events that conformed to the amplitude and rise-time criteria, both set up by the user. Each captured trace included 20 msec of pre-event baseline data. The system sampled events accurately up to 20 Hz—entirely adequate for capturing the relatively low frequency events in the experiments described herein. The analysis software provides amplitude, frequency, rise- and decay-time constant information for each current recorded.

Subsequent generation of histograms, cumulative plots fitting, and statistical analyses were performed with Microsoft Excel 3.0, Sigmaplot 4.1 (Jandel Scientific) and Systat. Synaptic current frequency information was divided into bins for plotting and statistical comparisons. Statistical analyses of differences between control and treatment groups were evaluated by a two-tailed test (Snedecor and Cochran, 1989). Synaptic current amplitude data were compared by plotting cumulative histograms. These plots were also utilized as estimated cumulative probability distributions for the determination of statistically significant differences between treatment groups using the Komolgorov-Simirnov test (Press et al., 1986).

Table II provides a comparison of synaptogenesis vs. recombinant nARIA or ARIA treatment in regulating nAChR gene expression. (Bold serves to highlight the differences.)

TABLE II

Comparison of Synaptogenesis vs. Recombinant nARIA or ARIA treatment in regulating nAChR gene expression.

| AChR subunit | α2 | α3 | α4 | α5 | α7 | β2 | β4 |
|---|---|---|---|---|---|---|---|
| Development in vivo | ND | 170% | 1 to ND | 500% | 1000% | +/− | 600% |
| Presynaptic input in vitro | — | 240% | — | 315% | 150% | — | 195% |
| Target contact in vitro | — | 1; 60% of control | — | 189% | 261% | ? | no▲ |
| Heart Kidney | | 148% | | 160% | 150% | | 143% |
| recombinant N-ARIA | — | 224% | — | 248% | 372% | ? | [0–400%] |
| recombinant ARIA | — | 1; 90% of control | — | 265% | 215% | ? | no▲ |

Table III provides a comparison of the regulation of ACh-gated currents induced by input and target vs nARIA and ARIA.

TABLE III

Comparison of the Regulation of ACh-Gated Currents Induced by Input & Target vs. nARIA and ARIA.

| Presynaptic input in vitro | | Target Contact in vitro: | |
|---|---|---|---|
| SMN | ↑1300% | Heart | ↓30% of control |
| VMN | ↑750% | | |
| Input Cond. Media | | Target Cond. Media | |
| SMN | ↑420% | Heart | ↓50% of control |
| VMN | ↑430% | Kidney | ↑225% |
| recombinant nARIA | ↑200–400% | recombinant ARIA | ↓60% of control |

Experimental Methods

Cell Culture

LSG Co-Cultures with Presynaptic Input and Target.

Dissociated embryonic sympathetic neurons from ED10 and ED17 were prepared and maintained in vitro as described in Role 1988 with modifications as noted herein. Under these conditions the neurons were devoid of nonneuronal cells and were both adrenergic and cholinoceptive. Innervation of sympathetic neurons by preganglionic microexplants was done according to previously described techniques (Gardette et al. 1991; Hasselmo and Bower, 1993). Assay of target effects on nAChR expression required coculture of atrial micro-explants (ED12) with LSG neurons in vitro. Changes in expression of subunit mRNAs were assayed after 3–4 days of coculture by quantitative RT-PCR (see below and Habecker and Landis, 1994).

Patch Clamp Recording

Recording of macroscopic and synaptic currents employed the whole-cell tight seal recording configuration of the patch clamp technique (Hammil et al., 1981). This techniques provided low noise recordings that allowed for resolution of elemental synaptic currents. Fabrication of patch electrodes, pipette and bath solutions were all as previously described (Moss and Role, 1993; Moss et al., 1989). Currents were recorded with an AXOPATCH 200A patch clamp amplifier and stored on videotape with a PCM digitizer (Instrutech VR-10B) for subsequent analysis off line. $I_{P(AChR)}$ is peak current.

Drug Application

Drugs and agonists were applied by microperfusion to small groups of cells via a large barreled delivery tube with continuous macroperfusion at 1 ml/min. This approach optimized speed of application (<30 msec), speed of removal and the ease of changing test solutions applied by the same device. A stable perfusion set-up was an essential component of the each recording set up.

Molecular Techniques

Identification of Subunit Gene Expression by PCR

The profile of subunit gene expression was analyzed by PCR amplification of cDNA using nAChR subunit specific primers according to our previously published techniques (Listerud et al., 1991). Briefly, total RNA was extracted by homogenization of tissue in 4M guanidine thiocyanate buffer followed by centrifugation through a 5.7M CsCl cushion. The isolated RNA was DNAse treated and reverse transcribed using oligo-dT primers. AMV-RT (reverse transcriptase) was used to amplify a fragment encoding the most variable portion of the nAChR subunits, the intracellular loop. The identity of the amplified products was verified by restriction mapping and/or Southern blotting (Ausubel et al., 1994).

Quantitative RT-PCR

Cell contents were collected by aspiration into DEPC containing solution and cDNA was synthesized by addition of random hexamer primers and Superscript® reverse transcriptase enzyme (BRL). The cDNA served as template for amplification by primers specific for the various nAChR subunits. The internal standard construct included sequences complimentary to all upstream and downstream primers used with an interposed multicloning site (MCS) linker. Thus, the efficiency of primer annealing to standard and to the cDNA template was equivalent. In order to detect the product of the reaction, trace amounts of isotope labeled nucleotides were added to the reaction mixture. After 23 rounds of amplification, an aliquot of the reaction mixture was removed and further amplified with fresh Taq polymerase and reaction mix. This step was repeated after another 23 cycles. The amplified fragment was separated from the unincorporated nucleotides by electrophoresis and the product was quantitated. The assay provided subunit specific quantification of $\alpha 2$, $\alpha 3$, $\alpha 4$, $\alpha 5$, $\alpha 7$, $\alpha 8$, $\beta 2$ and $\beta 4$ in individual samples which detected as little as 2 fg of each subunit.

COS Cell Transfection

Cells were tansfected according to established techniques (Falls et al., 1993). Briefly, pcDNA1-amp containing the nARIA or ARIA cDNA in sense or antisense orientation was introduced into COS cells using lipofectamine® (Gibco-BRL) per manufacturer's instructions. Twenty-four (24) hrs after transfection, the cells were washed and incubated in serum-free OPTI-MEM, (Gibco-BRL). After 48 hrs, the media was collected, centrifuged to remove debris and then concentrated 22-X using a Centriprep® 10 concentrator (Amicon). Aliquots were stored at −20° C. until use.

Tyrosine-Phosphorylation Assay

Cells were treated with L-15 media plus concentrated conditioned media from either sense, antisense, or non-transfected COS cells. After the desired incubation time, the cells were washed and lysed in 1% NP-40 buffer. The lysate was centrifuged and the protein in the supernatant was quantified with a Bradford analysis procedure (BioRad). Protein samples were electrophoresed on a 4% SDS-PAGE gel and electroblotted onto a PBDF membrane (S&S Inc). Then the membrane was probed for phosphotyrosine with a monoclonal antibody 4G10 (UBI), detected with a peroxidase-conjugated anti-mouse $IgG2_b$ antiserum (Boehringer-Mannheim) and visualized using the luminescent ECL® reagents (Amersham).

In Situ Hybridization

Cell-specific expression of AChR subunit mRNAs were assayed using in situ hybridization in tissue sections of spinal preganglionic nuclei with $^{35}$S-labeled complementary RNA probes as described (Devay et al., 1994; Ausubel et al, 1994). cDNAs encoding the non-conserved regions between transmembrane-spanning regions, TM3 and TM4, for each subunit have been subcloned into pGEM-3Z plasmids. Antisense riboprobes were transcribed in the presence of $^{35}$S-VTP using the Promega transcription kit. Hybridization was assayed by autoradiography, and Nissl staining allowed visualization of the cell bodies. $^{35}$S-labeled RNA probes provided good signal resolution with low background due to the high specific activity (cpm/probe molecule) and also due to the relatively low energy of $^{35}$S emission. Determination of hybridization involved comparison between parallel assays with antisense cRNA, sense RNA and RNase pre-treatment of the tissue. Non-isotopic labeling protocol utilizing Digoxigenin-11-UTP in place of the $^{35}$S-UTP was also used. The protocols were very similar (Bertrand et al., 1991).
Antisense Oligonucleotide Design and Experimental Protocols Antisense oligonucleotides for AChR subunits α2, α3, α4, α5 and α7 were targeted to a 15 base sequence spanning the initiation site of each subunit mRNA. The region upstream and including the ATG was divergent among the subunit sequences and in no case included <4 base mismatch with all chick cDNA sequences registered in GCG. Control oligos included missense sequences of identical composition of oligos mutated at 3 of the 15 bases (same GCG ratio). The uptake, metabolism, hybridization and block of subunit expression by oligonucleotides were studied in some detail to determine optimal conditions for specific block. Briefly, neurons were pretreated with an irreversible nAChR ligand (bromoacetylcholine bromide; BAC) and then incubated for 6–48 hrs with 10 μM oligo in heat inactivated medium) (Gardette et al., 1991; Listerud et al., 1991). The d-oligos were taken up and intact 15-mer within the cells was maximal within 6 hrs and still detected up to 48 hrs. α2, α3, α4, α5 and α7 have all been studied with this technique to determine their contribution to medial habenula nucleus (MHN) and LSG somatic nAChRs with reliable functional block by 24–48 hours. Antisense oligonucleotides were also designed to inhibit the expression of nARIA and ARIA. These oligos were directed against the translation start site or sequence within the N-terminal domain since the sequences are maximally divergent in this region. To optimize the antisense mediated block, and minimize the confounding contribution of pre-existent nARIA and ARIA, antisense was introduced just prior to the initial surge in expression of these factors during development (=ED4 for nARIA; =ED8 for ARIA). Treatment of preganglionic tissue of these ages with the antisense oligos effectively knocked out the expression of these factors and allowed us to ascertain the extent to which each of these factors contributed to developmental changes in nAChR expression.

A question remains as to whether ARIA or nARIA is required for regulation of nAChR channels by presynaptic input. This idea is tested by the selective block of nARIA or ARIA synthesis by antisense-mediated deletion. To optimize the antisense treatment, the region containing the presynaptic neurons is removed prior to the initial surge in nARIA and ARIA expression (E4 and E8, cord; E4 septal region). In this manner we may succeed in blocking the major increase in expression, thereby obviating effects of pre-existent nARIA or ARIA. Presynaptic microexplants are treated for 24–48 hrs in vitro with antisense oligos targeted to the initiation region of nARIA or ARIA mRNA. Then, nARIA or ARIA activity may be assayed in co-culture with LSG or MHN neurons (assay of nAChR macroscopic and single channel currents as above). The efficacy of antisense constructs is confirmed by quantitative RT-PCR of control and antisense-treated explants for nARIA, ARIA and transcripts unaltered by the treatment (e.g. actin). Specificity of the antisense is evaluated by assay of oligomers, equivalent in size and composition but with 20–25% mismatched bases. Presynaptic properties (e.g. electrical activity, transmitter release/mini amplitude) may be tested to control for other non-specific effects of the antisense.
Comparison of the Affinity of nARIA vs ARIA for Heparin Sulfate Proteoglycan.

MCF7 breast tumor cells were treated with conditioned media from either ARIA or nARIA transiently transfected COS1 cells. Some of the media was prebound with heparin attached to glass beads. Prior to treatment, the beads were pelleted by centrifugation to remove any heparin associated proteins. The supernatant was used to treat the MCF7 cells and tyrosine phosphorylation of the ARIA/nARIA receptor was analyzed. See FIG. 15. It appears that the ARIA is binding to heparin and is removed from the media by centrifugation. The nARIA lane shows a slight drop in signal which is unaffected by increasing concentrations of heparin (from 6 μg –60 μg). It is possible that this slight drop is an artifact of differential binding between the lanes and thus nARIA does not bind heparin.

Heparin is a component of both the cellular surface and the extracellular matrix. The difference in the binding affinities of nARIA and ARIA for heparin have two implications. (1) Heparin can affect the affinity of the ligand for the receptor as has been previously shown for HB-EGF. In this case, heparin may increase the affinity for the receptor. Accordingly, a given amount of ARIA may have higher affinity and thus more cellular activity and effect than the equivalent amount of nARIA. This implication may extend to other possible effects of the physiological concentration of the ligand. (2) The lack of affinity for heparin may result in greater solubility of nARIA in vivo since the molecule will not be bound to the extracellular heparin. This possibility may influence the localization of the ligand effects and the point concentration of the ligand.
Conclusions The series of experiments described herein are some examples illustrating possible uses of nARIA. As discussed above herein, there are many other possible therapeutic, diagnostic and pharmacologic uses of nARIA. The biological role of nARIA has been shown to be distinct from that of ARIA and from other members of the heregulin/NDF family. Therefore, nARIA may be useful in therapeutic treatments and as a diagnostic tool for abnormal neuronal conditions. In addition, a comparison of the expression levels and activities of the members of the NDF/heregulin/ARIA family may prove to be useful in the characterization and treatment of neuronal disorders and abnormal conditions and neurological developmental questions which are at this time unanswered.

Example 4

The n-ARIA Isoform of Neuregulin is both Necessay and Suficient for the Induction of Acetylcholine-Receptors in Neurons It is clear that the n-ARIA isoform of neuregulin is both necessary and sufficient for the induction of acetylcholine-receptors (nAChR) in neurons. The induction of nAChR expression normally occurs at specific sites within the CNS and PNS during synapse formation and can be mimicked by presynaptic input or presynaptic0input conditioned media. Definitive evidence has been uncovered showing that the expression is mediated by n-ARIA. The timing and pattern of expression as well as the primary structure and functional effects of n-ARIA differ importantly from the other neuregulins.
The Expression Profile of n-ARIA is Distinct from that of the Ia-Domain Containing Forms:

The n-ARIA sequence is unique. An extracellular Ig-like motif, common to all other neuregulins, is replaced by a highly conserved cys rich domain (98% identical chick to human and linked to a β1 type EGF-like domain.

n-ARIA is the only neuregulin isoform for which expression is restricted to the nervous system (both PCR and Northern analyses).

n-ARIA expression, unlike the Ig containing forms, is apparent at the earliest stages of neuronal differentiation (E2–E3 in chick; PCR and Northern analyses).

The development of isoform specific antibodies and the asessment of the distribution of n-ARIA protein in the CNS and PNS has been performed. A polyclonal sheep antibody wa raised which is specific to the cysteine rich domain containing isoforms of the "neu"-regulin gene. This antibody was developed against a peptide sequence encoding the hydrophilic portion within the highly conserved domain. The antibody is capable of recognizing both the denatured and natural protein states on solid matrix support (FIG. 16). Imunohistochemical studies demonstrate that this antibody recognizes both avian and mammalian homologues of the nARIA protein. Immunohistochemical studies have also demonstrated that: Unlike the Ig containing forms, n-ARIA is largely (but not exclusively) expressed by cholinergic and/or cholinoceptive neurons. n-ARIA expression is prominent in medial septal cholinergic nuclei, basal forebrain, deep cerebellar neuclei, cerebellar Purkinje neurons, and retinal ganglion neurons as well as in cranial, somatic and visceral motor nuclei.

n-ARIA protein appears to be targeted to axons and axon terminals as soon as such projections can be detected either in vitro or in vivo. n-ARIA immunoreactivity is localized in motor nerve terminal at the neuromuscular junction and "double" staining indicates that n-ARIA expression aligns with (post synaptic) α bungarotoxin binding, which reveals the distribution of muscle AchRs. n-ARIA immunoreactivity is also detected in axonal terminals and en passant synapses on CNS and PNS neurons (FIG. 17).

The Functional Profile of n-ARIA is Distinct from that of the Ig-Domain Containing Forms:

n-ARIA is more soluble than the Ig-domain containing forms and unaffected by heparin and less avidly bound by extracellular matrix proteins.

The activity of n-ARIA in inducing tyrosine phosphorylation in neurons is more potent, more raid and more persistent than Ig-domain containing forms.

Figure 18:
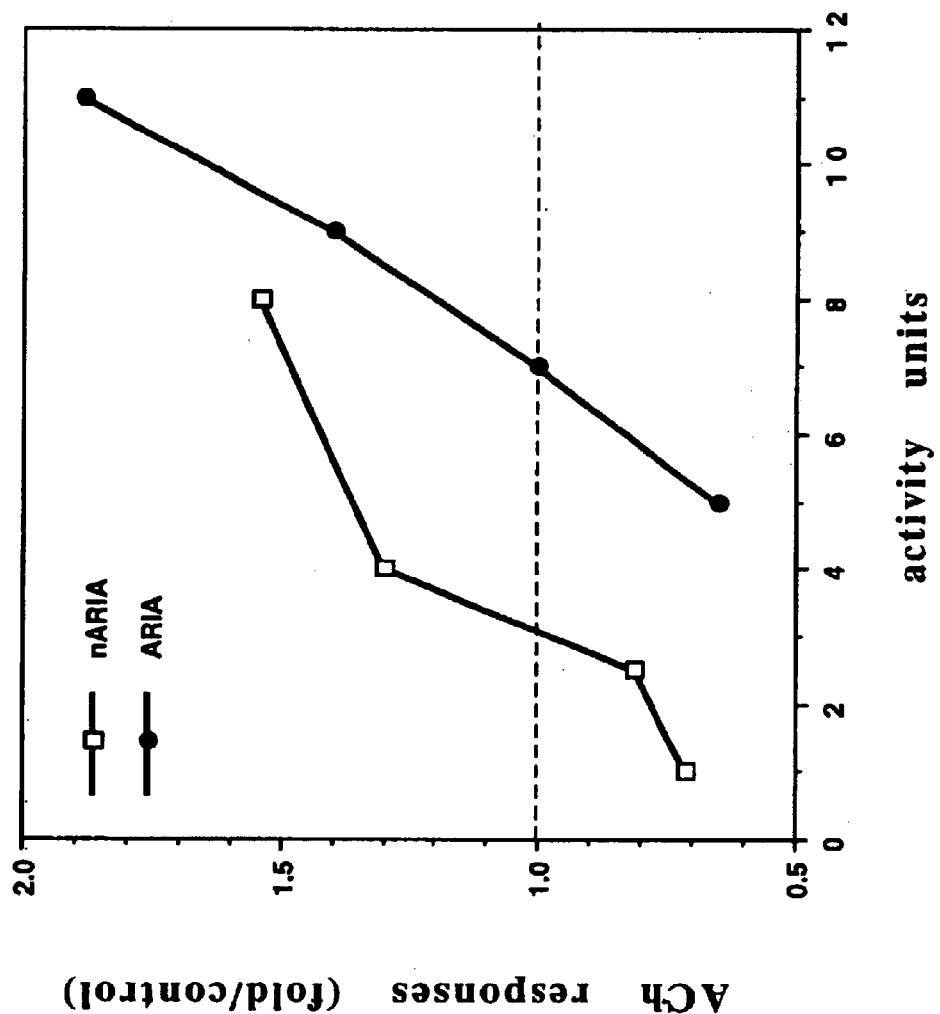

The induction of specific nAChR subunits and the enhancement of n-AChR-currents by presynatic input are specifically mimicked by recombinant n-ARIA protein. The activity of n-ARIA in inducing receptor expression in neurons is more potent and more persistent than Ig-domain containing forms (FIG. 18).

The ability to enhance α3 type nAChR subunit gene expression is unique to the n-ARIA isoform.

The ability to enhance α3 type nAChR subunit gene expression is unique to the n-ARIA isoform.

Most importantly, the induction of specific nAChR-currents by presynaptic input are selectively blocked by prior exposure of the input to n-ARIA specific antisense-oligonucleotides (FIG. 19) or n-ARIA antibodies.

The n-ARIA Isoforms

The role of n-ARIA in the differentiation and synaptic function of the septal cholinergic neurons that project to hippocampus and amygdala has been investigated. Specifically, evidence suggests that n-ARIA might collaborate with other growth factors, previously implicated in the differentiated function and perhaps, survival of CNS cholinergic neurons.

n-ARIA may induce several parameters of differentiated phenotype in central cholinergic neurons The effects of n-ARIA±target-derived growth factors, on CH synthesis and release have been examined. Transient depletion of n-ARIA (in vitro by antisense or antibody treatments to "knock down" endogenous n-ARIA) has been utilized to initially test for n-ARIA dependent changes cholinergic neurons.

Genomic probes to n-ARIA (i.e. the sequence encoding the crucial cys rich domain) have been developed. The effects of an n-ARIA-selective gene knock out was examined by using homologous recombination with subsequent excision of the selectable marker employing the Cre-LOXP approach. The n-ARIA exon-specific knock-outs are expected to survive embryogenesis as, unlike other neuregulins (including ARIA), expression is confined to the nervous system, allowing determination of the role of n-ARIA in differentiation, synaptic funtion and survival of CNS cholinergic neurons.

Example 5

Products of the neuregulin gene and their receptors, the erbBs, (erbB2, 3 and 4) control multiple critical biological processes. Dysregulation of Neuregulin-erbB signaling is associated with major human cancers, specifically in breast, ovarian prostate and lunch cancer. In some patients this is accompanined by the appearance of soluble erbBS in the circulation and/or elevated levels of auto-antibodies recognizing the erbBs. If soluble erbBs are predictive of dysregulated erbB-neuregulin expression of function, then sensitive assays for these proteins in patients' blood has potential to provide non-invasive prognostic information on disease status, both in detecting primary disease and in monitoring disease-free status following traditional therapies. Recently we demonstrated that interactions between neuregulin and erbB expressing cells induces membrane to nuclear translocation of the cytoplasmic domain of neuregulin. We constructed a neuregulin-green fluorescent protein fusion protein that allows us to detect erbB-neuregulin interactions. By coupling this assay with fluorescence activated cell sorting, we are devising a sensitive rapid and high throughput assay for the presence of erbBs in biological fluids. A further modification of this assay detects nuclear targeting of neuregulin-Gal4-regulated reporter gene. The level of reporter gene expression in dependent of the concentration of extracellular stimuli (e.g. erbbs), providing a means of not only detecting soluble erbBs in biological fluids, but quantifying levels. In addition, using reporter gene expression provides an amplification step that significantly increases the sensitivity of the assay.

Role of HEN1 in Neurogenesis and Recent Data on Neuregulin

We found that an embryonic neuronal specific basis-helix-loop-helix protein, HEN1 (also known as NSCL1 or NHLH), interacts with "LIM only" proteins. Examination of the expression patterns of XHEN1 and XLMO-3, the *Xenopus* homologs of these human genes, reveals extensive overlap during early neurogenesis. Co-expression of these two genes in *Xenopus* embryos induces a cascade of expression of neuronal specific basic-helix-loops-helix proteins that lead to neuronal differentiation. Recently, I tested whether neuregulin (NRG) cytoplasmic domain might mediate "back signaling". An intense subnuclear localization was observed in cells transfected with the NRG cytoplasmic domain. A similar observation was made in primary neuron immunostained with an antibody against the cytoplasmic tail of NFRG. This nuclear translocation requires a NLS motif at the beginning of the cytoplasmic domain, which includes eight amino acids: KTKKQRKK. One of the functions of this nuclear translocation was to induce apoptosis. Furthermore, a novel gene (CNIP) was found to bind to the cytoplasmic domain of NRG, which might be the modulator for the functions of NRG cytoplasmic domain.

CNIP: A Novel Interactor Protein Specific for the Cytoplasmic Domain of CRD Neuregulin The neuregulin (NRG) gene encodes a number of splice variants that are epidermal growth factor (EGF)-related polypeptides. The protein structure of most NRG isoforms includes 3 general domains:
1. The variable extracellular domain, including the EGF-like domain but differing amongst NRG isoforms by the inclusion of a cysteine rich or an Ig-like domain (referred to as CRD- or Ig-NRG, respectively,
2. A conserved transmembrane domain and
3. A cytoplasmic domain of unknown functions.

We have begun to explore whether the cytoplasmic domain of CR NRG (also known as nARIA or neuregulin) might mediate "back signaling" by interaction with specific cellular proteins. The interaction "hunt" for the cytoplasmic domain of NRG was performed using a *Xenopus* cDNA library. cDNAs from the strongest 14 of 4000 positives obtained were analyzed. All 14 interactors encode the same product. To test the specificity of the putative interactor, a panel of control baits were screened for binding with the gene product: only lexA-CRD-NRG cytoplasmic domain interacted strongly. Interactions with the cytoplasmic domains of TGFβ receptor, G proteins, cyclin, cyclin dependent kinase or Myc proteins do not occur. The expression pattern of the CRD-NRG Interactor Protein (CNIP was examined in *Xenopus* and found to be strikingly similar to that of CRD-NRG. Thus CNIP is prominently expressed in the nervous system, especially in the hindbrain, eyes and spinal cord. In view of the specificity of thei interactions as well as their overlapping patterns of expression with the nervous system CNIP-NRG interactions may occur in vivo.

Novel Functions of the Cytoplasmic Domain of Neuregulin

Neuregulins (NRGs) comprise a large family of EGF-like growth factors expressed in both the CNS and PNS. The NRG 1 gene encodes multiple splice variants including secreted and transmembrane isoforms. The external (N-terminal) portion of both membrane anchored and secreted NRG isoforms includes a characteristic Ig-like or cysteine rich domain, and an EGF-like domain that is essential for NRG-ErbB interactions. Membrane anchored and secreted NRG isoforms identified to date include one of three distinct (a, b or c-type) cytoplasmic domains. Although the cytoplasmic domains are highly conserved (85% identity form chick to human), the biological function is unknown.

We tested whether NRG cytoplasmic domain(s) might mediate "back signaling" in NRG expressing cells, following interaction of the tethered ligands with erbB receptors. And intense subnuclear localization was observed in cell transfected with the NRG cytoplasmic domain. A similar observation was made in primary neuron immunostained with an antibody against the cytoplasmic tail of NRG. This nuclear translocation requires a NLS motif at the beginning of the cytoplasmic domain, which includes eight amino acids: KTKKQRKK. The motif is highly conserved (the same sequence for human, rat, mouse, chick and Xenapus NRG). The nuclear translocation was augmented by activation of PKC, or cell expressing erbB receptors. One of the functions of this nuclear translocation was to induce apoptosis. Furthermore, a novel gene (CNIP) was found to bind to the cytoplasmic domain of NRG, which might be the modulator for the functions of NRG cytoplasmic domain.

CRD-NRG in Mouse Perpheral Nervous System Development.

Synaptogenesis at nerve-muscle junctions involves the redistribution of preexisting surface acetylcholine receptors (AchRs), as well as increased local synthesis and insertion of new receptors. The latter increase in nAChR expression is induced by members of the neuregulin (NRG) family (Fischbach and colleagues *Cell,* 72: 801; 1993). We have characterized herein an NRG isoform in chicks, mice and humans in which a highly conserve cysteinse-rich domain replaces the Ig-motif found in other NRGs; we have termed this variant CRD-NRG. CRD-NRG appears to be both a necessary and sufficient signal for the control of neuronal nAChR expression during synaptogenesis (Neuron, 20: 255; 1998). In situ hybridization analysis in embryonic mice reveals that CRD-NRG is highly expressed in all cranial nerve nuclei, visceral and somatic motor neurons, and in numerous CNS regions, including the olfactory and vomeronasal sensory neurons, the main and accessory olfactory and vomeronasal sensory neurons, the main and accessory olfactory bulbs, hippocampus, amygdala, thalamus, and hypothalamus, as well as septal cholinergic and dopaminergic nuclei, we now evaluate the role of NRG1 signaling in the development of the peripheral nervous system using CRD-NRG specific know out mice by in situ, immunocytological, and immunohistochemical studies.

Neuregulins, originally referred to as ARIA, heregulin (HRG), neu differentiation factor (NDF), glial growth factor (GGF), and sensorimotor-derived factor (SMDF), constitute a large family of structurally related glycoproteins which are produce as a consequence of alternative splicing of the neuregulin-1 (NRG-1) gene. Neuregulins function as ligands for the erbb family of receptor tyrosine kinases. Targeted disruptions of the entire NRG-1 gene, and of the genes for its three receptors, erb2, erb3, erb 4 have been generated (Gassmann et al., 1995, Lee et al. 1995, Meyer and Birchmeter, 1995, Kramer et al. 1996, Riethcacher et al. 1997, and Erickson et al., 1997). The phenotype of these mice demonstrated the multiple essential roles of this signaling system in the formation of the peripheral nervous system and the heart.

As many as 14 different neuregulin cDNAs have been isolated (Fischback and Rose, 1997). While all known NRG isoforms contain an EGF-like repeat which is considered essential for NRG-1 activity, isoforms may or may not be have a kringle domain, an Ig-like domain, a spacer domain, a transmembrane domain, and/or a variety of different cytoplasmic tails. However, all isoforms can be broadly classified into two currently mutually exclusive categories: isoforms which contain an If-like domain N-terminal to the EGF-like domain (Ig-NRGs), such as ARIA, HRG, NDF, and Ggf, and isoforms which contain a cysteine-rich domain N-terminal to the EGF-like domain (CRD-NRFs), sucha s SMDF.

Different classes of isoforms show distinct patterns of spatial and temporal expression during embryogenesis (Meyer et al. 1997), suggesting that the different isoforms could be mediating distinct biological signals. Analysis of mice null for Ig-containing NRGs and comparative analysis of mice null for all NRGs or just Ig-containing NRFs provides further evidence to support this conclusion (Meyer et al 1997, Sandrock et al. 1997).

We have found by in situ hybridization analysis in embryonic mice that CRD-NrG is highly expressed in all cranial nerve nuclei, visceral and somatic motor neurons, and in numerous CNS regions, including the olfactory and vomeronasal sensory organs, the main and accessory olfactory bulbs, hippocampus, amygdala, thalamus, and hypothalamus, as well as septal cholinergic and dopaminergic nuclei. In addition, we have generated mice which are homozygous hull exclusively for all CRD-containing NRG-1 isoforms. We now present evidence for distinct and essential roles of CRD-mediated NRG-1 signaling in the development of the peripheral and central nervous systems.

Example 6

Neuregulins constitute a large family of structurally related glycoproteins produced by alternative splicing of the neuregulin-1 gene.[1,2] Neuregulin signaling, mediated by activation of the erbB family of receptor tyrosine kinases, has been implicated in the inductive interactions between pre- and post-synaptic partners at developing nerve-muscle and nerve-nerve synapses.[1,3-5] Gene targeting to selectively disrupt cysteine rich domain (CRD) containing NRG-1 isoforms in mice reveals that CRD-NRG-1 is required for synaptogenesis in the peripheral nervous system. In CRD-NRG-1$^{(-/-)}$ mice, peripheral projections defasciculate and display aberrant branching patterns upon arrival within their targets. The profuse sprouts of motor projections are transiently associated with broad bands of postsynaptic ACh receptor clusters. Schwann cell precursors, that initially accompany peripheral projections, are absent from axonal terminations within muscle. Following an aborted attempt at synapse formation, sensory and motor nerves withdraw and eventually degenerate. Our data demonstrate the essential role of CRD-NRG-1 mediated signaling for coordinating nerve, target, and Schwann cell interactions in the formation and maintenance of peripheral synapses.

Alternative splicing generates at least fifteen different neuregulin-1 (NRG-1) cDNAs.[1,6] All identified NRG-1 isoforms can be broadly classified into three mutually exclusive categories: Type I and II isoforms that contain an Ig-like domain (Ig-NRGs) and Type III isoforms that contain a cysteine-rich domain (CRD-NRGs) N-terminal to a common EGF-like sequence (FIG. 20A).[3,6-11] Although different NRG-1 isoforms show distinct patterns of spatial and temporal expression during embryogenesis (data not shown), it is not clear to what extent these isoforms mediate distinct biological responses.[3,11] Mice homozygous for disruptions of all NRG-1 isoforms, all Ig-NRG-1 isoforms, or all isoforms containing a cytoplasmic tail die at E10.5 from heart defects, prior to significant expression of CRD-NRG-1 isoforms.[12,15] As such, these mice provide no direct evidence as to the possible functions of CRD-NRG-1 isoforms in neural development or synaptogenesis.

CRD-NRG-1 isoforms are the predominant NRG-1 transcripts in the murine nervous system after E10.5. In particular, the temporal pattern of CRD-NRG-1 expression in hindbrain and spinal cord visceral and somatic motor neurons, as well as in cranial and trunk sensory ganglia, suggests an important role for this isoform in synapse formation (FIG. 20E. b & data not shown).[3,5,10,11] To assess the potential role of CRD-NRG-1 isoforms in neural development, we generated mice selectively lacking all NRG-1 isoforms that contain a CRD domain within the N-terminus.

Experimental Method

CRD-NRG-1 $^{(+/-)}$ embryonic stem (ES) cells were isolated following homologous recombination with a mutated CRD-encoding exon that included a nonsense mutation/frameshift and a novel XbaI site inserted into the codon immediately 3' of the last methionine (FIG. 1B). These ES cells were used to generate germline chimeras following injection into mouse blastocysts. Male chimeras transmitting the mutant alleie were used to produce fertile heterozygote offspring.

Figure 20A:
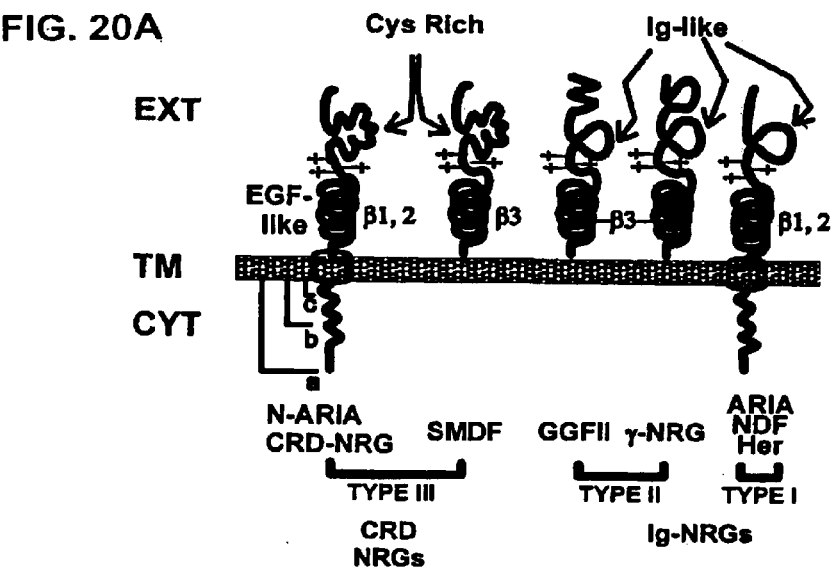
Figure 20B:
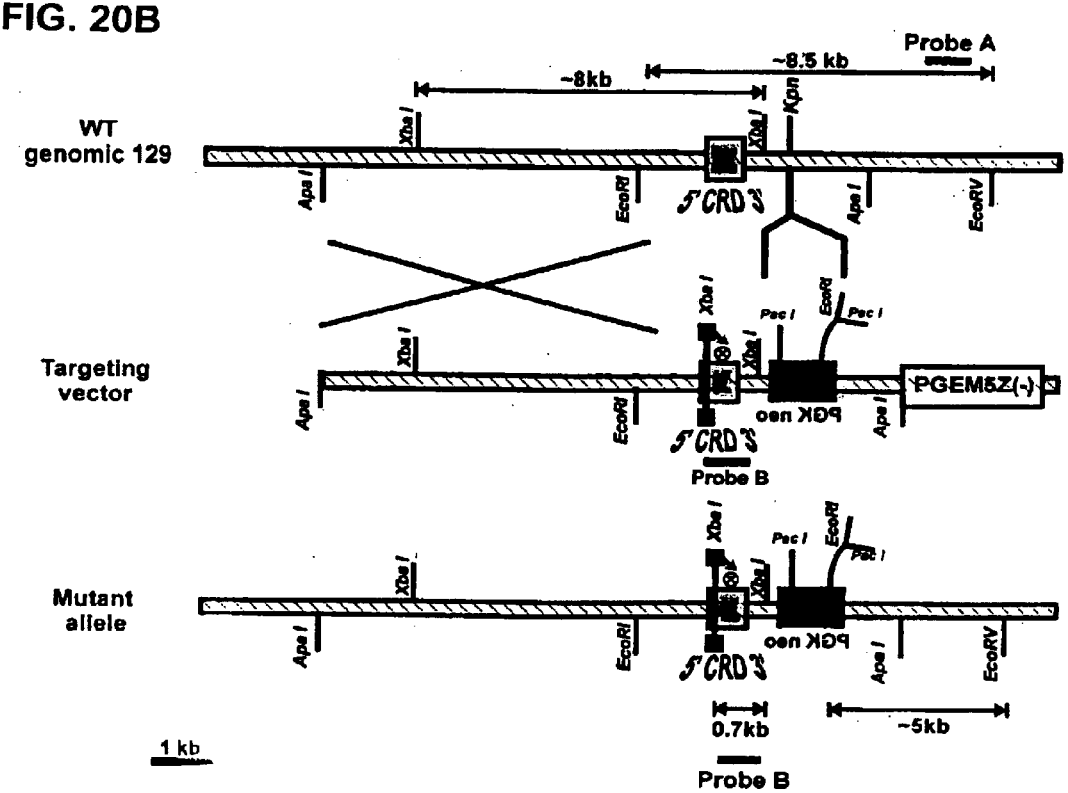
Figure 20C:
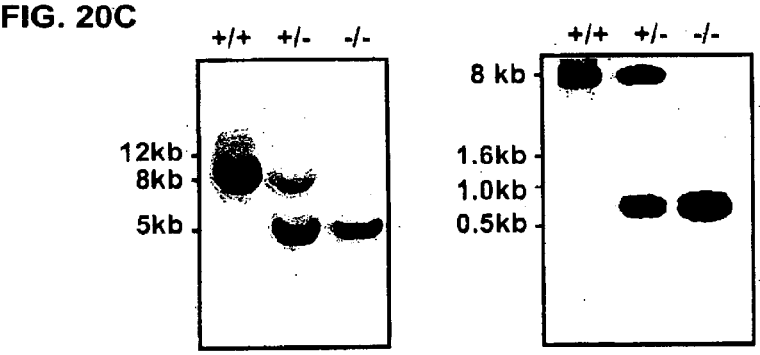
Figure 20D:
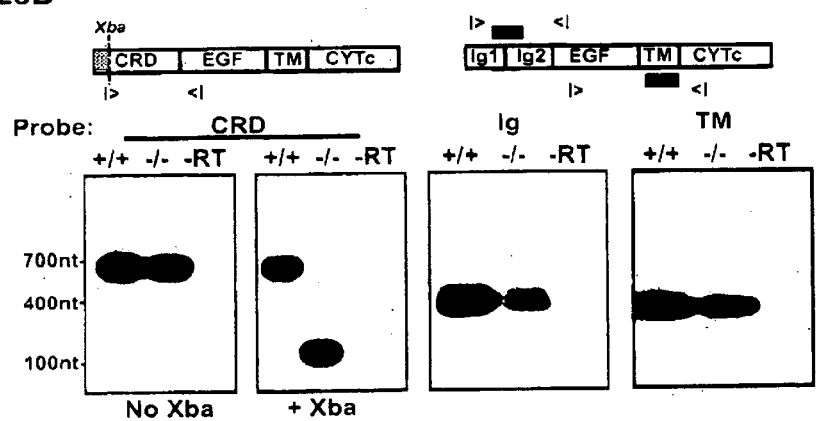
Figure 20E:
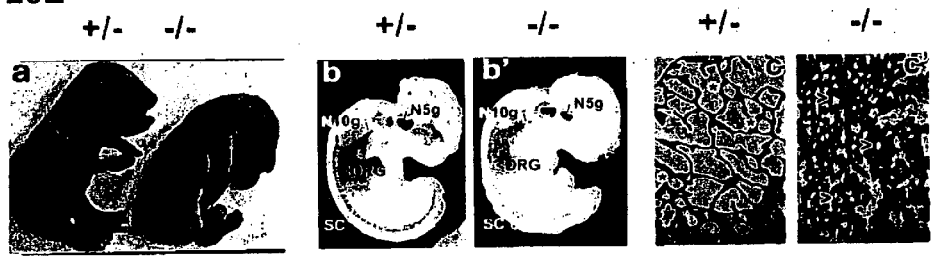

CRD-NRG-1$^{(+/-)}$ mice were interbred to produce homozygote CRD-NRG-1$^{(-/-)}$ mice. In the resulting litters, cleaned, dead pups were consistently found among viable, healthy littermates (FIG. 20E. a). Genotype analysis identified the dead pups as CRD-NRG-1$^{(-/-)}$ (22% of first 132 P0 pups) (FIG. 20C). As expected, mutant animals expressed both Ig-containing and mutant CRD-containing mRNAs (FIG. 20D). In situ hybridization revealed that the spatial and temporal expression pattern of the nonsense mutation containing-CRD-NRG-1 mRNA was not altered in the mutants (FIG. 20E, b vs. b¹, & data not shown).

CRD-NRG-1$^{(-/-)}$ pups were iimp, and limb movement was not detectable (FIG. 20E, a). These pups did not breathe, rapidly became cyanotic, and finally were unresponsive to all stimuli despite the presence of a heartbeat for several minutes after birth. Histological analysis confirmed that hearts of CRD-NRG-1 $^{(-/-)}$ mice were normal but that the lung alveoli failed to expand, confirming that CRD-NRG-1$^{(-/-)}$ pups never take a breath (data not shown and FIG. 20E. c vs. c').

Figure 21A:
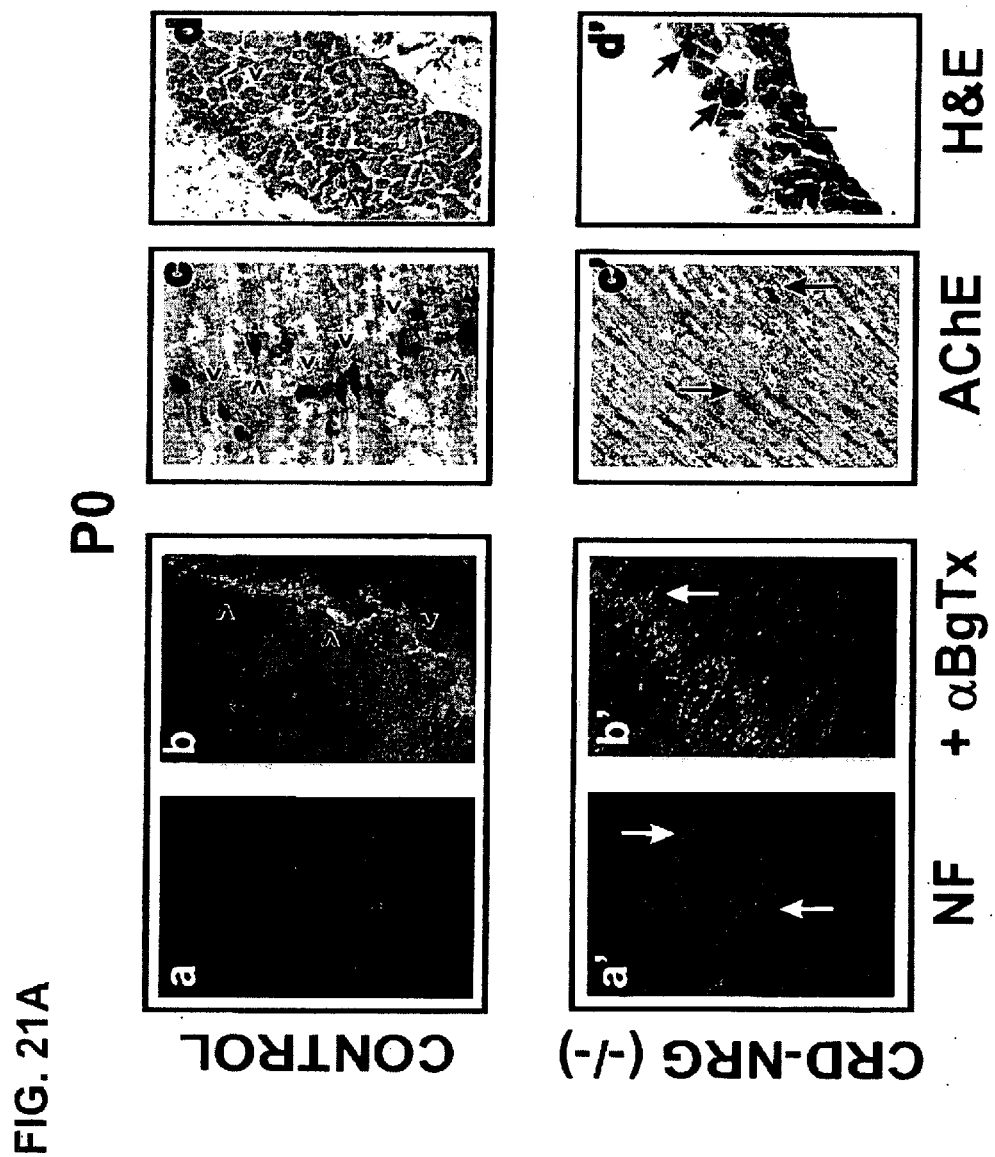
Figure 21B:
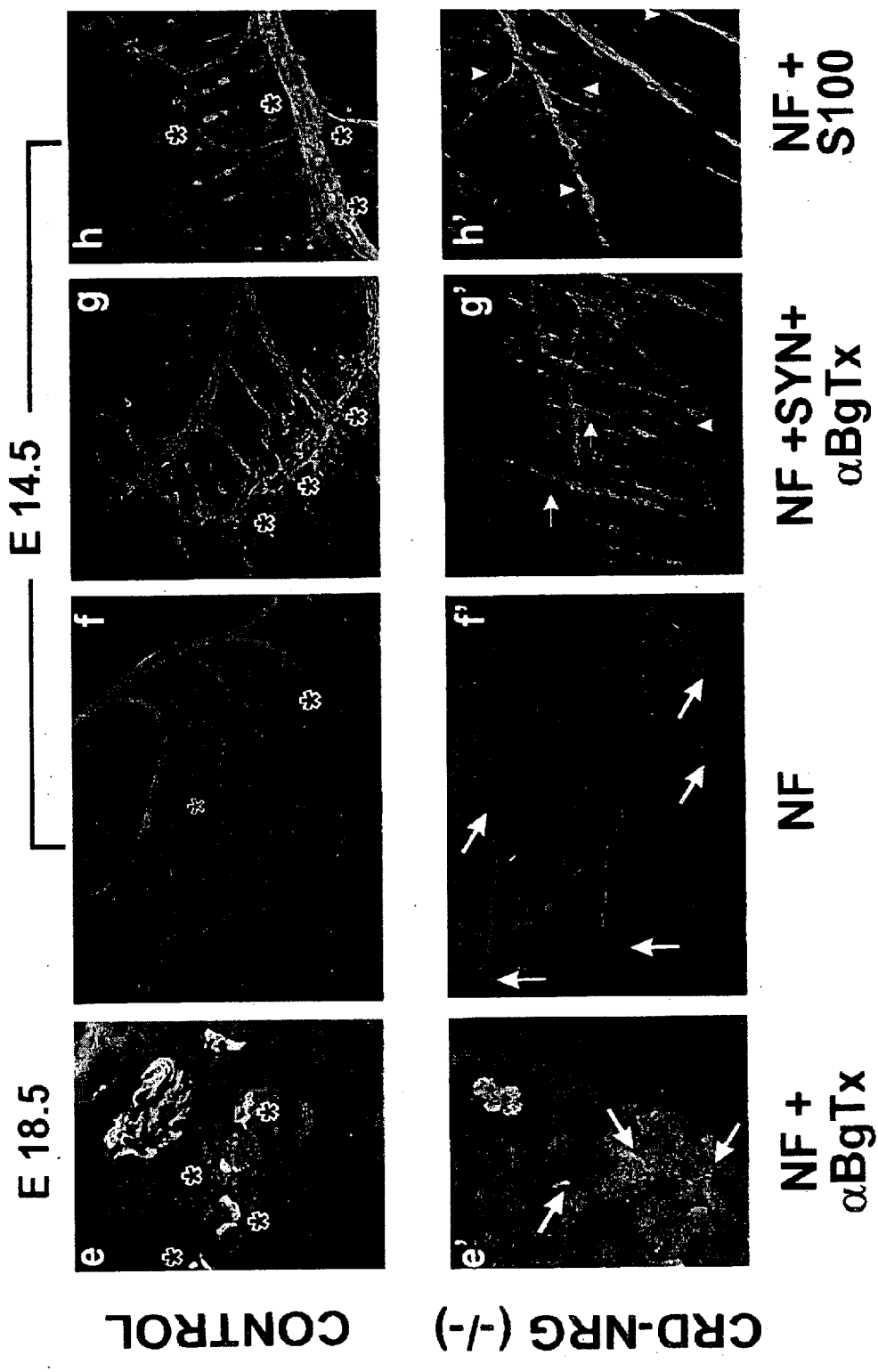

Examination of P0 mutant diaphragms revealed only remnants of nerve-muscle synapses (FIG. 21A, a vs. a). Mutants had decreased skeletal muscle mass, and mutant skeletal muscle had central nuclei with prominent nucleoli compared to the elongated, eccentric, peripheral nuclei in control muscle (FIG. 21A, d vs. d' and data not shown). CRD-NRG-1$^{(-/-)}$ mice lacked an intradiaphragmatic phrenic nerve plexus (FIG. 21A, a vs. a'). Bands of α-bungarotoxin (αBgTx) positive acetylcholine receptor (ACHR) clusters, reminiscent of end-plate zones, were present but abnormally broad (~6 times wider than littermate controls) (FIG. 21A. b vs. b). These diffuse bands of AChR clusters, the absence of associated nerve, and the scattered neurofilament(+) fragments indicate prior presence, and subsequent degeneration, of motor projections. Indeed, examination of diaphragms from E14.5, E15.5, E18.5, and P0 mutant mice revealed elaborate phrenic nerve arborization at E14.5 and progressive loss of these nerve fibers during subsequent stages of development (FIG. 21B, f vs. f, and data not shown). Phrenic nerve processes in E14.5 CRD-NRG-1$^{(-/-)}$ mice were grossly abnormal with extensive defasciculation, aberrant axonal branching patterns, and projections extending as far as the most lateral borders of the diaphragm (FIG. 21B, f vs. f). Although post-synaptic AChR clusters were sometimes detected subjacent to neurofilament(+) and synaptophysin(+) structures in mutant E14.5 diaphragms, these clusters were typically more diffuse and more often devoid of associated nerve than age-matched controls (FIG. 21B, g vs g').

A similar pattern of defective nerve-muscle interaction was detected in intercostal and limb muscle groups (e.g., scattered αBgTx(+)-AChR clusters and lack of co-localization with nerve; FIG. 2B, e vs. e' and data not shown). Acetylcholinesterase (AChE), which is normally enriched at the site of nerve-muscle contact following the establishment of synapses, was scattered and faint in mutant muscle (FIG. 21A, c vs. c').[16] Thus, in CRD-NRG-1^ mice, motor axons initially extend to and contact the target muscle and some aspects of pre- and post-synaptic specializations were evident. However, as these preliminary synaptic interactions were not sustained, we next examined if the number of motor neurons was affected.

Somatic motor neurons were visualized by in situ hybridization to the vesicular ACh transporter (VAT) mRNA.[17] The number of VAT(+) cell bodies within the ventral horn of C1–C6 of E18.5 mutants was 60% less than that of controls (FIG. 22A. a vs. a', b). A dramatic reduction in the diameter of peripheral nerves arising from motor pools at other spinal cord levels, including those within intercostal and hindlimb muscles, was also evident in E18.5 CRD-NRG-1 $^{(-/-)}$ animals compared to controls (FIG. 21B. e vs. e' and data not shown). Likewise. E18.5 but not E14.5. cervical dorsal root ganglia and their peripheral sensory projections were dramatically decreased in size in CRD-NRG-1 $^{(-/-)}$ compared with control animals (FIG. 22B, d vs. d' and data not shown). The observed degeneration of peripheral sensory and motor nerve projections by E18.5 is likely to account for the abnormal morphology of forelimbs and absence of all limb movement, evident in both E18.5 and P0 CRD-NRG-1 $^{(-/-)}$ mice (FIG. 20E, a and data not shown).

We next examined the development of the sensory and motor projections prior to arrival in their respective target fields. At E1 1, whole mount immunostaining of mutant embryos with β-Tubulin III, a pan-neuronal marker, revealed that initial projections of both sensory and motor neurons were fasciculated (FIG. 23B, h vs. h').[18] At later stages and at more caudal levels of mutant embryos, these terminal projections displayed dramatic defasciculation, aberrant and irregular branching, and markedly increased terminal sprouting (FIG. 22B, f vs. f). Likewise, in caudal hindlimb muscle of older mutant animals, supernumerary terminal motor sprouts were visualized with VAT Ab staining (FIG. 22B, g vs. g'). The VAT(+) sprouts and AChR clusters, visualized as αBgTx "hot spots," were each detected without the complementary marker of nerve-muscle synapse formation (data not shown). Finally, at later times and at more rostral levels of mutant embryos, the terminal projections of sensory and motor neurons were smaller, bulb-shaped, and compact, when compared to the more splayed nerve endings in control animals (FIG. 22A, c vs c': 22B, e vs e').

Taken together, these data indicate a temporal and rostral-caudal pattern whereby the initial trajectory and outgrowth of peripheral nerves in CRD-NRG-1 $^{(-/-)}$ mice are grossly normal. However, once within the terminal fields, projections defasciculate, displaying profuse and aberrant branching, and subsequently, appear bulbous and then fragmented, consistent with their ultimate retraction and degeneration.

Peripheral nerves projecting to their targets are lined by neural crest-derived Schwann cell precursors that express erbBS, p75 NGF receptor, and S100β.[19,20,21] At E18.5, mutant embryos lacked erbB3/p75-expressing cells in both dorsal and ventral roots (FIG. 22B, d vs. d' and data not shown). Likewise, S100β expressing cells were absent from intramuscular branches of the phrenic nerve in E14.5 mutant diaphragms (FIG. 2B, h vs h'). Although erb83(+) cells were detected along nerve roots in E11 mutant mice, the progressive, rostral-caudal loss of these cells was evident by E12 (FIG. 3B, h vs. h'; FIG. 4B, j vs. j'). The spatial pattern of Schwann cell precursor loss was revealed by examination of more caudal structures in older CRD-NRG-1$^{(-/-)}$ animals. In peripheral hindlimb muscle of E18.5 CRD-NRG-I$^{(-/-)}$ mice, S100β(+) cells lined the VAT(+) axons and preterminal branches but were not detected at the site of VAT (+)nerve terminations (FIG. 22B, I) In contrast, in control embryos VAT(+) preterminal nerve branches and nerve terminations were always associated with S100p (+) staining (FIG. 22B, I¹).

Figure 23A:
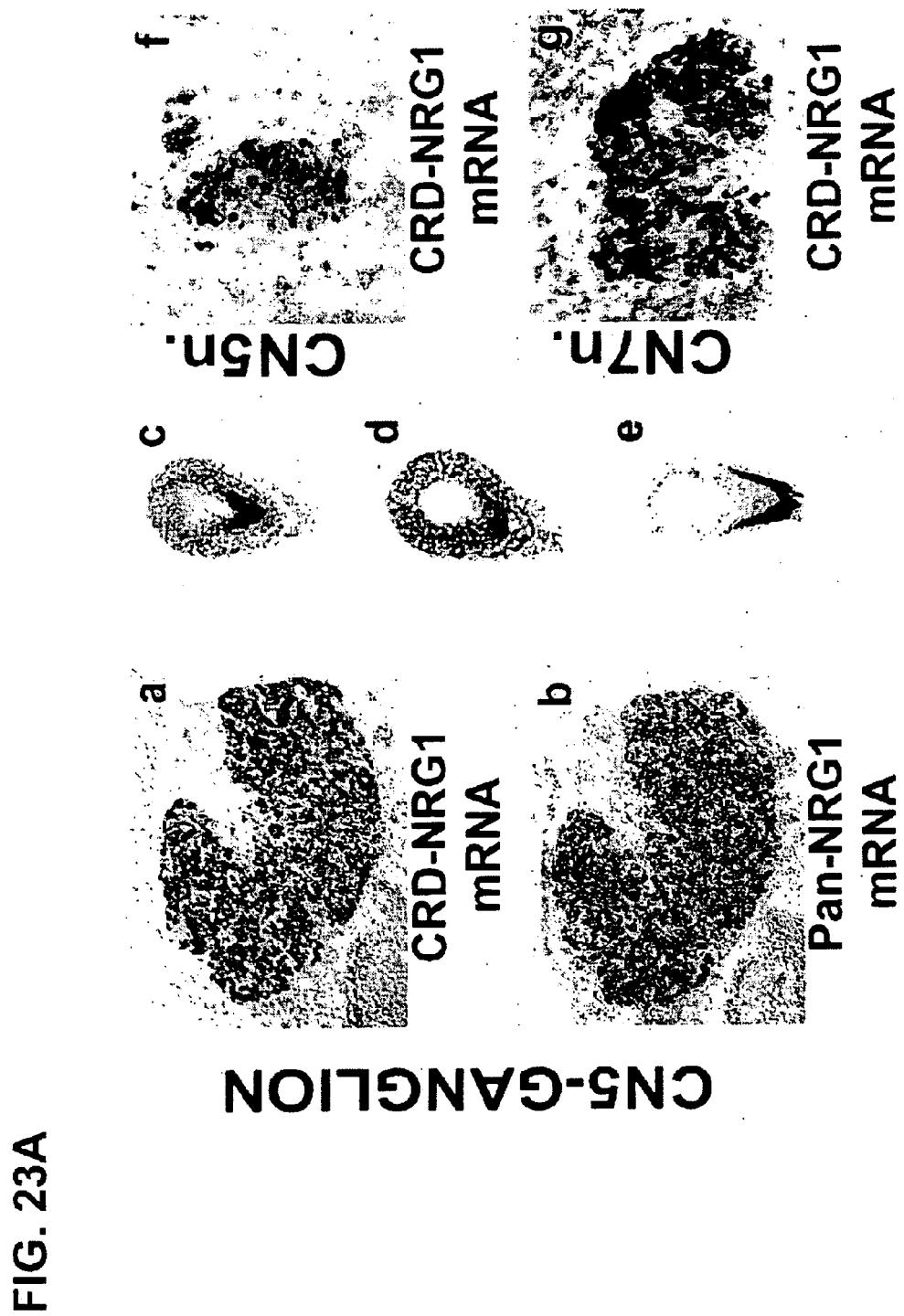
Figure 23B:
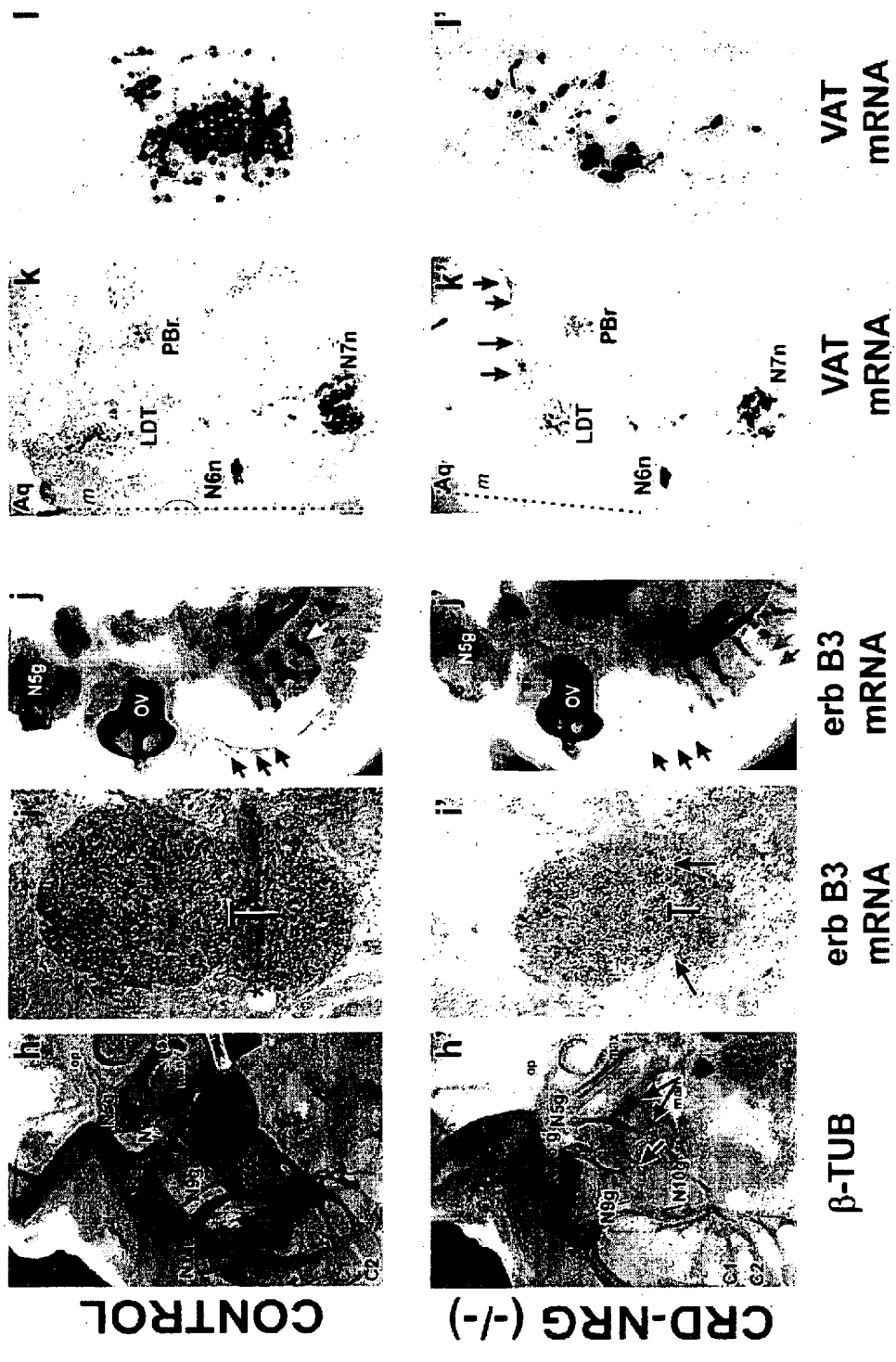

Cranial sensory ganglia strongly express CRD-NRG-1 isoforms (FIG. 20E. b: FIG. 23A, a, b, and data not shown).[11] CRD-NRG-1. erbBS and erbB4 mRNA have been detected in the peripheral targets of these ganglia, including vibrissa follicles (FIG. 23A, c-e).[11] The fate of these neuronal populations and their associated erbB3(+) Schwann cells was significantly altered in CRD-NRG-1 $^{(-/-)}$ mice. Both neural crest and otic placode-derived cellular elements of cranial ganglia appear to form in CRD-NRG-1 $^{(-/-)}$ mice, but their initial projections were markedly less robust in mutants (FIG. 23B, h vs. h'). As cranial nerves enter their target fields, the pattern of nerve defasciculation and extensive branching was seen (FIG. 23B, h vs. h'). The subsequent demise of cranial nerve projections was apparent by E12.5, and by E14.5. cranial ganglia (including the trigeminal and geniculate) and their associated nerves were dramatically reduced in size in CRD-NRG-1 $^{(-/-)}$ mice (FIG. 23B. i vs. i' and data not shown). Furthermore, cranial nerve projections were nearly devoid of associated Schwann cell precursors in CRD-NRG-1 $^{(-/-)}$ mice compared with controls (FIG. 23B, i vs. i' and data not shown). Examination of cranial nerves at earlier stages of development reveals the initial appearance and subsequent loss of erbB3(+) cells along the ascending spinal accessory (N11n) nerve and the coalescence of vagus nerve (N10n) and in the ganglia and along the peripheral projections of the trigeminal (N5g), geniculate (N7g), glossopharyngeal (N9g), and vagal N10g) ganglia (FIG. 23B, j vs. j and data not shown).

CRD-NRG-1 is expressed in VAT(+) cells of cranial motor nuclei, such as the trigeminal (N5N), facial (N7N), and dorsal motor nucleus of the vagus (FIG. 23A, f & g and data not shown). At E18.5 the number and distribution of VAT(+) neurons within the brainstem of CRD-NRG-1 $^{(-/-)}$ embryos was abnormal with the most striking changes seen in the motor nuclei of cranial nerves N5N and N7N (FIG. 4B, k vs. k'; i vs. i'). Preliminary analysis of other VAT(+) neurons within brainstem and forebrain nuclei also indicates possible changes in development and synaptogenesis (D. W. and L. W. R., in preparation).

In summary, CRD-NRG-1 is an essential, nerve-derived component of peripheral synaptogenesis. The phenotype associated with the selective disruption of CRD-NRG-1 mediated signaling is distinct from all other NRG-1 ligand or receptor knockouts reported to date. CRD-NRG-1 $^{(-/-)}$ mice die within minutes of birth, unable to breathe due to the lack of functional phrenic nerve-diaphragm synapses. The defects in CRD-NRG-1 $^{(-/-)}$ mice are evident as a temporal progression and in a rostral-caudal pattern during embryogenesis. Thus, both motor and sensory nerve projections initially emanate from hindbrain to lumbar spinal cord levels. However, with the arrival of projections within their respective targets, mutant peripheral nerves branch extensively, and Schwann cell precursors, initially associated with peripheral projections, do not survive. By parturition, CRD-NRG-I $^{(-/-)}$ mice have severe deficits in the number and extent of motor and sensory neurons, consistent with extensive neural degeneration. At birth, skeletal muscle targets display features of immaturity similar to those found in human myotubutar myopathy.[22] Genetic defects in a muscle phosphatase have been implicated in the severe X-linked form of this disease.[23]

NRG-1 signaling has long been implicated as an important component for survival and differentiation during Schwann cell development.[2,13,19] TOss of Schwann cell precursors is a phenotype shared by CRD-NRG-1 $^{(-/-)}$ and erbBS null mice.[21] The early effects of postnatal axotomy on Schwann cell apoptosis are partially reversed by exogenous NRG-1 protein.[20,24] Furthermore, previous studies comparing NRG-1 $^{(-/-)}$ mice and 1 g-NRG-1 $^{(-/-)}$ mice led to the proposal that ncn-1 g containing NRG isoforms might be required for Schwann cell survival.[11] The unique neural specificity of CRD-NRG-1 expression in mouse and the progressive loss of erbB3(+) Schwann cell precursors along peripheral nerve projections in CRD-NRG-1 $^{(-/-)}$ mice implicate CRD-NRG-1 isoforms as the essential, nerve-derived trophic signal for erbBS-mediated Schwann cell survival.

Sensory and motor neurons are critically dependent on target-derived trophic support during early development[25,26] Likewise, the development and terminal differentiation of target muscle requires interaction with motor nerve. The phenotype of CRD-NRG-1 $^{(-/-)}$ mice demonstrates that CRD-NRG-1 isoforms are necessary components comprising the reciprocal cascades of these cellular interactions. Birth, initial differentiation and peripheral projections of motor and sensory neurons proceed apace in the absence of CRD-NRG-1 isoforms. Initial aspects of post-synaptic organization, such as clustering of AChRs in muscle, are also detected in CRD-NRG-1 $^{(-/-)}$ mice. The AChR-cluster inducing signal, agrin, acts through MuSK receptor complexes in skeletal muscle.[29,30] It is noteworthy that mice in which these genes are disrupted show abnormalities in neuromuscular junction formation, but motor projections neither withdraw nor degenerate.[29,30]

In contrast, the genetic disruption of CRD-NRG-1 results in both pre- and post-synaptic defects consistent with loss of reciprocal, inter-dependent nerve and target-derived trophic support. Furthermore, the target-derived support that appears to be required for the persistence of the incoming nerves is not constitutively available but must be elicited by a nerve-derived signal. We propose that this nerve-derived signal is CRD-NRG-1. As Schwann cell precursors might also provide essential trophic support for developing nerves, and these cells fail to survive in CRD-NRG-1 $^{(-/-)}$ ice, it is possible that Schwann cell precursors and/or peripheral targets respond individually or synergistically to a common nerve-derived, CRD-NRG-1-mediated signal that normally elicits context-dependent, trophic and synaptogenesis.

Methods

Generation of CRD-/-Mice. A mouse 129/SV genomic library (Lamba EMBL3, Stratagene) was screened with a mouse CRD-specific probe. Positive clones were mapped and sequenced revealing that the CRD-domain is encoded by a single exon. PCR-mediated site-directed mutagenesis and standard protocols in molecular biology were used to create the targeting vector. ES cells were electroporated, selected for G418 resistance (150 µg/ml active substance), and screened by Southern blot for homologous recombination. ES clones, in which homologous recombination resulted in replacement of one of the wild-type NRG-1 alleles with the mutant gene, were injected in C57/BL6/J blastocysts. Chimeric males were mated with 129/Sv females to generate heterozygotes on a pure 129/Sv background.

RT-PCR. Total brain/spinal cord RNA was isolated using Trizol (Gibco BRL) following the manufacturers protocol, and first-strand cDNA was made using Superscript II reverse transcriptase following the manufacturers protocol (Gibco BRL). Mouse-specific primers and oligonucleotide probes corresponded to the following: from Genbank L41827, CRD 5' primer (549–565), CRD-probe (582–605); from Genbank u02318: Ig 5' primer (499–518), Ig/CRD 31 primer (885–903), egf-cyt primers (913–931), (1184–1203), Ig probe (608–631), TM probe (1080–1103). Note that all primer pairs span exon-intron boundaries.

In Situ Hybridization and Cell Counts. In situ hybridization (ISH) probes were as follows: mouse probes specific for CRD domain (corresponding to Genbank AF045654, 607-1206), PAN-NRG-1 (corresponding to Genbank AF045654, 867-1277), erbB3 (Corresponding to Genbank u29339, 3321-4113), erbB4 (corresponding to Genbank L07868, 3088-3957), VAT (gift of Dr. J. Dedman; Genbank AF019045, 945-2157) or rat 75 NGF receptor (gift of Dr. Moses Chao). Embryos were fixed in 4% paraformaldehyde by transcardial perfusion, followed by post-fixation overnight at 4° C. Following cryoprotection in 30% sucrose, embryos were embedded in OCT and 12 µm sections were cut on a cryostat. ISH was done as previously described.[31] For cell counts, 10 µm transverse serial sections were cut through C1–C6 and stained for VAT. Total number of nuclei of VAT(+) cells in every sixth section was then counted. Counts between ages are not strictly comparable as total cell numbers were not corrected for split or multiple nucleoli. We feel our counts reflect a conservative estimate of the cell loss, as motor neurons with retracted processes are included. Whole-mount ISH was done as previously described.[32]

Histological Analysis and Immunostaining. Lung was fixed overnight in 4% paraformaldehyde and embedded in paraffin. 8 µm sections were cut and stained with H&E. Diaphragm was sandwiched between liver, flash-frozen in liquid-nitrogen cooled isopentane, and 6 µm sections were stained with H&E. AChE staining was done as described previously.[33] Whole-mount immunostaining using monoclonal antibody to β-Tubulin III (Sigma) was done as previously described.[34] After staining, embryos were dehydrated and cleared in cedarwood oil. Whole-mount diaphragm staining was done as previously described.[29,30] Immunofluorescence labeling employed monoclonal anti-neurofilament NF-60 & 168 antibodies (Sigma), anti-S100β antibody (DAKO), FITC-conjugated alpha btx (Molecular Probes), anti-synaptophysin antibody (gift of Dr. Pietro de Camilli), and rhodamine or FITC-conjugated anti-mouse or anti-rabbi antibodies (Jackson Immunoresearch).

REFERENCES

References to Examples 1–5

Abuchowski et al., In: "Enzymes as Drugs", Holcenberg et al., eds. Wiley-Interscience, New York, N.Y., 367–383 (1981).

Arenella, L. S., Oliva, J. M. Jacob, M. H. (1993) Reduced levels of acetylcholine receptor expression in chick ciliary ganglion neurons developing in the absence of innervation. J. Neuroscience 13(10): 4525–37.

Ausubel, F., Brent, R., Kingston, R., Moore, D., Seidman, J. G., Smith, J. and Struhl, K. eds. (1994) Current protocols in Molecular Biology Green Publishing Associates, Inc.

Berg, D. K., Boyd, R. T., Halvorsen, S. W. Higgins, L. S., Jacob, M. H., Margiotta, J. F. (1989) Regulating the number and function of neuronal acetylcholine receptors. Trends Neurosci. 12: 16–21.

Bertrand, D., Cooper, S., Valera, D. and Ballivet, M. (1991) Electrophysiology of neuronal nicotinic acetylcholine receptors expressed in Xenopus oocytes following nuclear injection of genes or cDNAs. Med Neurosci. 4: 174–193.

Betz, H. (1990) Homology and analogy in transmembrane channel design: lessons from synaptic membrane proteins. Biochemistry 29: 3591–99.

Boulter, J., Evans, K., Goldman, D., Martin, G., Treco., D., Heinemann, S., Patrick, J. (1986) Isolation of a cDNA clone coding for a possible neural nicotinic acetylcholine receptor-subunit. Nature 319: 368–74.

Boyd, R. T., Jacob, M. H., Couturier, S., Ballivet, M., Berg, K. D. (1988) Expression and regulation of neuronal acetylcholine receptor mRNA in chick ciliary ganglia. Neuron 1: 495–502.

Brussaard, A. B., Yang, X., Doyle, J. P., Huck, S., Role. L. W. (1994) Developmental regulation of multiple nicotinic AChR channel subtypes in embryonic chick habenula neurons: Contributions of both the 2 and 4 subunit genes. Pflugers Archiv. (In press.).

Brussaard, A. B., McGehee, D. S. and Role, L. W. (1994b) Presynaptic input, in the absence of target contact, recapitulates a subset of the modifications of nAChR channels induced in vivo to enhance synaptic transmission. (to be submitted to J. Physiol.)

Carpenter et al., Toxicol. Appl. Pharmacol., 18: 35–40 (1971).

Clarke, P. B. S., Hamill, G. S., Nadi, N. S., Jacobowitz, D. M., Pert, A. (1986) 3H-nicotine-and 125I-alpha-bungarotoxin-labeled nicotinic receptors in the interpeduncular nucleus of rats. II. Effects of habenular deafferentation. J. Comp. Neur. 251: 407–13.

Conroy, W. G., Vernallis, A. B., Berg, D. K., (1992) The 5 gene product assembles with multiple acetylcholine receptor subunits to form distinctive receptor subtypes in brain. Neuron 9: 679–91.

Deneris, E. S., Connolly, J., Rogers, S. W., Duviosin, R. (1991) Pharmacological and functional diversity of neuronal nicotinic acetylcholine receptors. Trends Pharmacol. Sci 12: 34–40.

Devay, P., Qu, X. and Role, L. W. (1994) Developmental regulation of nAChR subunit gene expression during establishment of pre- and post-synaptic connections of lumbar sympathetic neurons of embryonic chicken. Devel. Biol. 162: 56–70.

Engisch, K. L., Fischbach, G. D. (1994) The development of ACH- and GABA-activated currents in embryonic chick ciliary ganglion neurons in the absence of innervation in vivo. J. Neurosci. 1992, 12: 1115–25.

Falls, D., Rosen, K., Corfas, G., Lane, W. and Fischbach, G. D (1993) ARIA, a protein that stimulates acetylcholine receptor synthesis, is a member of the Neu ligand family. Cell 72: 801–815.

Fischbach, G. D., Role, L. W. and Hurre, R. I. (1984) The accumulation of acetylcholine receptors at nerve-muscle synapses in culture. In: Cellular and Molecular Biology of Neuronal Development. I. Black (ed.), Plenum Press. pp 107–115.

Gardette, R., Listerud, M. D., Brussaard, A. B., Role, L. W. (1991) Developmental changes in transmitter sensitivity and synaptic transmission in embryonic chicken sympathetic neurons innervated in vitro. Dev. Biol. 147: 83–95.

Grynkiewicz, G., Poenie, M. and Tsien, R. Y. (1985) A new generation of Ca2+ indicators with greatly improved fluorescence properties, J. Biol. Chem. 260: 3440–3450.

Habecker, B. and Landis, S. (1994) Noradrenergic Regulation of Cholinergic Differentiation. Science 264: 1602–1604.

Hammil, O. P., Marty, A., Neher, E., Sakemann, B. and Sigworth, F. J. (1981) Improved patch-clamp techniques for high-resolution current recording from cells and cell-free membrane patches. Pflugers Arch. 391: 85–100.

Hasselmo, M. E. and Bower, J. M. (1993) Acetylcholine and memory. Trends in Neurosci. 16: 218–222.

Heinemann, S., Boulter, J., Deneris, E., Connoly, J., Duvousin, R., Papke, R., Patrick, J. (1990) The brain nicotinic acetylcholine receptor gene family. Progr. Brain Res. 86: 195–203.

Holmes, W. E., Sliwkowski, M. X., Akita, R. W., Henzel, W. J., Lee, J., Park, J. W., Yansura, D., Abadi, N., Raab, H., Lewis, G. D., et al. (1992) Identification of heregulin, a specific activator of p185erbB2. Science 256: 1205–1210.

Jacob, M. H. (1991) Acetylcholine receptor expression in developing chick ciliary ganglion neurons. J. Neurosci. 11: 1701–12.

Katre et al., Proc. Natl. Acad. Sci. USA 84: 1487–1491 (1987).

Köhler and Milstein Eur. J. Immunol. 6: 511–519 (1976).

Kriegler, M. (1990) Gene Transfer and Expression: A Laboratory Manual, Stockton Press, New York, N.Y.

Levey, M. S., Brumwell, C., Dryer, S., Jacob, M. (1994) Innervation and target tissue interactions differentially regulate acetylcholine receptor subunit transcript levels in Lipscombe, D., Madison, D. V., Poenie, M., Reuter, H., Tsien, R. W. and Tsien, R. Y. (1988) Imaging of cytosolic Ca2+ transients arising from Ca2+ stores and Ca2+ channels in sympathetic neurons. Neuron 1: 355–365.

Listerud, M., Brussard, A. B., Devay, P., Colman, D. R., Role, L. W. (1991) Functional contribution of neuronal AChR subunits by antisense oligonucleotides. Science 254: 1518–21.

Marchionni, M. A., Goodearl, A. D., Chen, M. S., Bermingham, M. O., Kirk, C., Hendricks, M., Danehy, F., Misumi, D., Sudhalter, J., Kobayashi, K., et al., (1993) Glial growth factors are alternatively spliced erbB2 ligands expressed in the nervous system. Nature 362: 312–318.

Mandelzys, A., Pie, B., Deneris, E. S., Cooper, E. (1994) The developmental increase in ACh current densities on rat sympathetic neurons correlates with changes in nicotinic Ach receptor a-subunit gene expression and occurs independently of innervation. J. Neurosci. 15: 2357–64.

Margiotta, J. F., Gurantz, D. (1989) Changes in the number, function and regulation of nicotinic acetylcholine receptors during neuronal development. Dev. Biol. 135: 326–39.

McGehee, D. S., and Role, L. W. (1995) Physiological Diversity of nicotinic acetylcholine receptors expressed by vertebrate neurons. Annual Review of Physiology (in press).

McGehee, D. S., Yang, X., Devay, P., Heath, M. J. S., Role, L. W. Nicotine potentiates synaptic transmission through presynaptic aBgTx sensitive acetylcholine receptors. Soc. Neurosci. Abstr. 19: 463.

Moss, B. L. and Role, L. W. (1993) Enhanced ACh sensitivity is accompanied by changes in ACh receptor channel properties and segregation of ACh receptor subtypes on sympathetic neurons during innervation in vivo. J. Neurosci. 13: 13–28.

Moss, B. L., Schuetze, S. M., Role. L. W. (1989) Functional properties and developmental regulation of nicotinic acetylcholine receptors on embryonic chicken sympathetic neurons. Neuron 3: 597–607.

Nef, P., Oneyser, S., Alliod, D., Couturier, S., Ballivet, M. (1988) Genes expressed in the brain define three distinct neuronal nicotinic acetylcholine 3-receptors. EMBO J. 7: 595–601.

Newmark et al., J. Appl. Biochem. 4: 185–189 (1982).

Press, W., Flannery, B., Teukolsky, S. and Vettering, W. P. (1986) Are two distributions different? Komolgorov-Smirnov test. In Numerical Recipes: The Art of Scientific Computing (New York: Cambridge Univ. Press) pp 472–475.

Ramirez-Latorre, J., Qu, Z., and Role, L. W. (1993) Participation of 5 in neuronal nicotinic AChR channels. Soc. Neurosci. Abstr. 19: 1533.

Role, L. W. (1988) Neural regulation of acetylcholine sensitivity of embryonic sympathetic neurons. Proc. Natl. Acad. Sci. USA 85: 2825–2829.

Role, L. W. (1992) Diversity in primary structure and function of neuronal nicotinic acetylcholine receptor channels. Curr. Opin. Neurobiol. 2: 254–62.

Sambrook, J., Fritsch, E. F. and Maniatis, T. (1989). Molecular cloning: a laboratory manual (Cold Spring Harbor Laboratory Press, Cold Spring Harbor, N.Y.), 2nd Ed.

Sargent, P. B. (1993) The diversity of neuronal nicotinic acetylcholine receptors. Ann Rev. Neurosci. 16: 403–33.

Seguela, P., Wadiche, J., Dineley-Miller, K., Dani, J. A., Patrick, J. W., (1993) Molecular cloning, functional properties and distribution of rat brain 7: a nicotinic cation channel highly permeable to calcium. J. Neurosci. 13: 596–604.

Sendecor and Cochran, (1989)

Simmons, L. K., Moss, B. L., Schuetze, S. M. and Role, L. W. (1988) Developmental regulation and modulation of neuronal nicotinic acetylcholine receptor channels in Nicotinic Acetylcholine Receptors in the Nervous System. NATO ASI series H: Cell Biology. Vol. 25H, Ed. F. Clementi, C. Gotti & E Sher, Springer-Verlag, Berlin-Heidelberg, pp 379–392.

Smith, M. A., Margiotta, J. F., Berg, D. K. (1983) Differential regulation of acetylcholine sensitivity and -bungarotoxin-binding sites on ciliary ganglion neurons in cell culture. J. Neurosci. 7: 149–70.

Tsien, R. Y. (1989) Fluorescent probes of cell signalling. Ann. Rev. Neurosci. 12: 227–253.

Vernallis, A. B., Conroy, W. g., Berg, D. K. (1993) Neurons assemble acetylcholine receptors with as many as three kinds of subunits while maintaining subunit segregation among receptor subtypes. Neuron. 10: 451–64.

Wada, E., Wada, K., Boulter, J., Deneris, E., Heinemann, S., Patrick, J., Swanson, L. W. (1989) Distribution of 2, 3, 4, and β2 neuronal nicotinic receptor subunit mRNAs in the central nervous system: a hybridization histochemical study in the rat. J. Comp. Neurol. 284: 314: 35.

Wen, D., Peles, E., Cupples, R., Suggs, S. V., Bacus, S. S., Luo, Y., Trail, G., Hu, S. Silbiger, S. M., Ben Levy, R. et al., (1992). New differentiation factor: a transmembrane glycoprotein containing an EGF domain and an immunoglobulin homology unit. Cell 69: 559–572.

Wen, D., Suggs, S. V., Karunagaran, D., Liu, N., Cupples, R. L., Luo, Y., Janssen, A. M., Ben-Baruch, N., Trollinger, D. B., Jacobsen, V. L., Meng, S.-Y., Lu, H. S., Hu, S., Chang, D., Yang, W., Yanigahara, D., Koski, R. A., and Yarden, Y. (1994) Mol. Cell. Biol. 14: 1909–1919.

References to Example 6

1. Fischbach G. D. & Rosen KM ARIA: a neuromuscular junction neuregulin. Annu RevNeurosci. 20, 429–458 (1997).
2. Marchionni M. A. et al. Neuregulins as potential neuroprotective agents. Ann. N.Y. Acad. ScL 825, 348–365 (1997)
3. Yang, X., Kuo, Y., Devay, P Yu. C. & Role, L. W. A cysteine-rich isoform of neureguiin controls the level of expression of neuronal nicotinic receptor channels during synaptogenesis. Neuron 20, 255–270 (1998).
4. Ozaki, M., Sasner, M., Yano, R. Lu, H. S., & Buonanno, A. Neuregulin-beta induces expression of an NMDA receptor subunit. Nature 390, 691–694(1997).
5. Sandrock AW Jr. et al. Maintenance of acetylcholine receptor number by neuregulins at the neuromuscuiar junction in vivo. Science 276, 599–603(1997).
6. Marchionni M. A. et al. Gliai growth factors a real alternatively spliced erbB2 ligands expressed in the nervous system. Nature 362. 312–318 (1993).
7. Wen D. et al. Neu differentiation factor: a transmembrane glycoprotein containing an EGF domain and an immunogiobulin homology unit. Cell 69, 559–572(1992).
8. Holmes W. E. et a/., Identification of heregulin. a specific activator of p185erbB2. Science 256, 1205–1210 (1992).
9. Falls, D. L, Rosen, K. M. Corfas, G., Lane, W. S.,& Fischbach, G. D. ARIA, a protein that stimulates acetylcholine receptor synthesis, is a member of the neu ligand family. Cell 72, 801–815 (1993).
10. Ho, W. H., Armanini M. P. Nuijens. A., Phillips, H. S., & Osheroff, P. L. Sensory and motor neuron-derived factor. A novel heregulin variant highly expressed in sensory and motor neurons. J Biol Chem. 270. 14523–14532 (1995).
11. Meyer D. et a/., Isoform-specific expression and function of neuregulin. Development 124, 3575–3586(1997).
12. Kramer R. et a/., Neuregulins with an Ig-like domain are essential for mouse myocardial and neuronal development Proc Natl Acad Sci USA 93, 4833–4838 (1996).
13. Meyer D., & Birchmeier. C Multiple functions of neuregulin in development. Nature 378. 286–390(1995).
14. Erickson S. L. et ai ErbBS is required for normal cerebellar and cardiac development: a comparison with ErbB2-and heregulin-deficient mice. Development 124, 4999–5011 (1997).
15. Liu X. et al. Domain-specific gene disruption reveals critical regulation of neuregulin signaling by its cytoplasmic tail. Proc. Natl. Acad. Sc/., in press.
17. Hall Z. W. & Sanes J. R. Synaptic structure and development: the neuromuscular junction. Cell 72Suppl, 99–121 (1993). 17. Naciff J. M., Misawa H., & Dedman J. R. Molecular characterization of the mouse vesicular acetylcholine transporter gene. Neuroreport 8, 3467–3473 (1997).
18. Easter, S. S. Jr., Ross, L. S. & Frankfurter, A. Initial tract formation in the mouse brain. JNeurosci. 13, 285–299 (1993).
19. Jessen K R. & Mirsky R. Origin and early development of Schwann cells. Microsc Res Tech. 41. 393–402(1998)
20. Grinspan, J. B. Marchionni. M A. Reeves., M., Coulaloglou, M., & Scherer, S. S. Axonal interactions regulate Schwann ceil apopfosis in developing peripheral nerve: neuregulin receptors and the role of neuregulins. J. Neurosci. 16, 6107–6118 (1996).
21. Riethmacher D. ef a/. Severe neuropathies in mice with targeted mutations in the ErbB3 receptor. Nature 389. 725–730 (1997).
22. Helliwell, T. R., Ellis, I. H., & Appleton, R. E. Myotubular myopathy: morphological, immunohistochemical and clinical variation. Neuromuscul Disord. 8, 152–161 (1998).
23. Laporte J, et al. A gene mutated in X-linked myotubular myopathy defines a new putative tyrosine phosphatase family conserved in yeast. Nat Genet. 13: 175–182(1996).
24. Trachtenberg J. T. & Thompson W. J. Schwann cellapoptosis at developing neuromuscular junctions is regulated by glial growth factor. Nature 379, 174–177 (1996).
25. Oppenheim R. W. Cell death during development of the nervous system. Annu Rev Neurosci. 14, 453–501(1991).
26. Grieshammer, U., Lewandoski. M., Prevette, D., Oppenheim, R. W., & Martin, G. R. Muscle-specific cell ablation conditional upon Cre-mediated DMA recombination in transgenic mice leads to massive spinal and cranial motoneuron loss. Dev. Biol. 197, 234–247(1998).
27. Jo. S. A., Zhu, X., Marchionni. M. A. & Burden, S. J. Neuregulins are concentrated at nerve-muscle synapses and activate ACh-receptor gene expression. Nature 373. 158–161 (1995).
28. Moscoso L M. et al. Synapse-associated expression of an acetylcholine receptor-inducing protein. ARIA/heregulin, and its putative receptors. ErbB2 and ErbBS, in developing mammalian muscle. Dev Biol. 172, 158–169(1995).

29. DeChiara T. M. et al. The receptor tyrosine kinase MuSK is required for neuromuscular junction information in vivo. Cell 85, 501–512 (1996).
30. Gautam M. et al. Defective neuromuscular synaptogenesis in agrin-deficient mutant mice. Cell, 525–535 (1996).
31. Wang, F., Nemes, A., Mendelsohn. M., & Axel, R. Odorant receptors govern the formation of a precise topographic map. Cell 93, 47–60 (1998).
32. Streit A. et al. Preventing the loss of competence for neural induction: HGF/SF, L5 and Sox-2.Development 124, 1191–1202 (1997).
33. Karnovsky, M. J. & Roots L. A "direct-coloring" thiocholine method for cholinesterases. J. Histochem. Cytochem. 12, 219–221 (1964).
34. Lumsden, A. & Keynes R Segmental patterns of neuronal development in the chick hindbrain. Nature 337. 424–428 (1989).

What is claimed is:

1. A method for determining whether an agent is capable of modulating the binding of a nARIA polypeptide having the sequence identified as SEQ ID. NO:4 to a receptor selected from the group consisting of erbB2, erbB3 and erbB4, which method comprises:

(a) contacting the nARIA polypeptide with the agent and a receptor selected from the group consisting of erbB2, erbB3 and erbB4, under conditions permitting the binding of the nARIA polypeptide to the receptor;

(b) measuring the amount of nARIA polypeptide in step (a) bound to the receptor; and (c) comparing the amount so measured in step (b) to the amount of the nARIA polypeptide which would bind to the receptor if in the absence of such agent, a difference in the amounts indicating that the agent modulates the binding of the nARIA polypeptide to the receptor.

2. The method of claim 1, wherein the nARIA polypeptide is bound to an affinity derivative.

3. The method of claim 1, wherein the receptor is bound to an affinity derivative.

4. The method of claim 3, wherein step (b) comprises the use of an antibody specific for the nARIA polypeptide.

5. The method of claim 2 or 3, wherein the affinity derivative is selected from the group consisting of sepharose, cellulose, plastic, glass, glass beads or steptavidin-coated plastic.

* * * * *

SEQUENCE LISTING

<160> NUMBER OF SEQ ID NOS: 5

<210> SEQ ID NO 1
<211> LENGTH: 3212
<212> TYPE: DNA
<213> ORGANISM: CHICKEN nARIA

<400> SEQUENCE: 1

```
cggatgctgc tgctactgtc acttctgccg ctgccgctgt tgttacagat tttgcttttg      60
ctccttctac cgcatgacaa ttgttttcct cgcctaagca gataccagcc tcagatgctc     120
aaggtgagag tcttgccttt cgctctgggc tattggttca cttaatccgg tcaatttgtt     180
cgctgctcgt ggttgtcttt ctccccgccc tccttccccc tgttttgttt tgtttcgctt     240
gctttcgggg ggacgctcct tccctcagtc agaagagctg gaattgcttg agaggcgtat     300
aaggaattat aaaagtggcc aggaaacacg agcgcagtga ctgcagagct gcccttggct     360
tcggcaaggc agcgtgagcg gcagagggct cgggcagggg gcgggggtc tccttttcc      420 cgtgcgttcc tcttctccca gttcggatga tgttgctgtt tcggacctct cgctgactcc     480
tgccctgtga tttttgctga gcgctgtgac tgttactccg tctctttctg tctgtgtttc     540
acagtaatgg actgtgatag agttaaggcc ttttggaggt gagctgtgtc acagctgatg     600
cttaaacatg tctgaagtag gcaccgagac tttccccagc ccctcggctc agctgagccc     660
tgatgcatcc cttggcgggc tcccggctga ggagaacatg ccggggcccc acagagagga     720
cagcagggtc ccaggtgtgg caggcctggc ctcgacctgc tgcgtgtgcc tggaagcaga     780
gcgactgaag ggctgcctca actctgagaa gatctgcatc gcccctatcc tggcttgcct     840
gctcagcctc tgcctctgca ttgctggcct caagtgggtc tttgtggaca agattttga     900 gtatgactct cctacacacc ttgaccctgg gaggatagga caagacccaa ggagcactgt     960
ggatcctaca gctctgtctg cctgggtgcc ttcggaggtg tatgcctcac ccttccccat    1020
acctagcctt gagagcaagg ctgaagtgac agtgcaaact gacagctcgc tcgtgccctc    1080
caggcccttc cttcagcctt ctctctacaa ccgcatccta gatgtcgggt tgtggtcctc    1140
tgccacaccg tcactgtcac catcctccct ggagcctacc acggcatctc aggcacaagc    1200
aacagaaacc aatctccaaa ctgctccaaa actttccact tctacatcta caactgggac    1260
aagtcatctc acaaaatgtg acataaagca gaaagccttc tgtgtaaatg ggggagagtg    1320
ctacatggta aaagacctcc caaaccctcc acgatacct a tgcaggtgcc caaatgaatt    1380
tactggtgat cgctgccaaa actacgtaat ggccagcttc tacaagcatc ttgggattga    1440 atttatgaa gctgaggaac tgtaccagaa acgggtgctg accataactg gcatttgcat    1500
tgctcttcta gtagttggca tcatgtgtgt ggtggcctac tgcaaaacca agaagcagag    1560 gaaaagttg catgaccgcc ttcggcagag ccttcgctca gagaggaaca acgttatgaa    1620
catggcaaat gggccacacc accccaaccc accaccagac aatgtccagc tggtgaatca    1680
```

-continued

```
gtacgtttca aaaaacataa tctccagtga acgtgtcgtt gagcgagaaa ccgagacctc    1740
gttttccaca agccactaca cctcaacaac tcatcactcc atgacagtca cccagacgcc    1800
tagccacagc tggagtaatg gccataccga agcattctc tccgaaagcc actccgtgct    1860
cgtcagctcc tcagtggaga atagcaggca caccagccca acagggccac gaggccgcct    1920
caatggcatt ggtgggccaa gggaaggcaa cagcttcctc cggcatgcaa gagagacccc    1980
tgactcctac cgagactctc ctcacagtga aggtatgtc tcagctatga ccacaccagc     2040
tcgcatgtca cccgttgatt tccacactcc aacttctccc aagtcccctc catctgaaat    2100
gtcaccacca gtttccagct tgaccatctc catcccttcg gtggcggtga gtcccttat    2160 ggacgaggag agaccgctgc tgttggtgac cccaccacgg ctgcgtgaga agtacgacaa    2220
ccaccttcag caattcaact ccttccacaa caatcccacc catgagagca acagtctgcc    2280
acccagtcct ctgaggatag tggaggatga agagtatgag accacgcagg agtacgaacc    2340
agcacaggag cctccaaaga aactcaccaa cagccggagg gtgaaaagaa caaagcccaa    2400
tggccatatt tccagcaggg tagaagtgga ctccgacaca agctctcaga gcactagctc    2460
tgagagcgaa acagaagatg aaagaatagg tgaggataca ccatttctta gcatacaaaa    2520
tcccatggca accagtctgg agccagccgc tgcatatcgg ctggctgaga acaggactaa    2580
cccggcaaat cgcttctcca caccagaaga gttgcaagca aggttgtcca gtgtaatagc    2640
taaccaagac cctattgctg tataagacat aaacaaaaca catagattca catgtaaaac    2700 tttatttat ataatgaagt attccacctt taaattaaac aatttatttt attttagcaa     2760
ttccgctgat agaaaacaag agtggaaaaa gaaacttta taaattaagt atacgtatgt     2820
acaaatgtgt tatgtgccat atgtagcaat ttttacagt atttccaaaa tggggaaaga     2880
tatcaatggt gcctttatgt tatgttatgt tgagagcaag ttttgtacag ctacaatgat    2940
tgctgtcccg tagtattttg caaaaccttc tagccctcag ttgttctggc tttttttgtgc   3000 attgcattat aatgactgga tgtatgattt gcaagaattg cagaagtccc catttgcttg    3060
ttgtggaatc cccagatcaa aaagccctgt tatggcactc acaccctatc cacttcacca    3120
ggaaaaaaaa aaaatcaaaa aaaaaaaaa aaaaaaaga aagaaagag aaaaaagaaa       3180 agaaaaagaa aaaaaagct gaaaaaataa aa                                   3212
```

<210> SEQ ID NO 2
<211> LENGTH: 1070
<212> TYPE: PRT
<213> ORGANISM: CHICKEN nARIA
<220> FEATURE:
<221> NAME/KEY: UNSURE
<222> LOCATION: (32)
<223> OTHER INFORMATION: Wherein Xaa = unclear results
<220> FEATURE:
<221> NAME/KEY: UNSURE
<222> LOCATION: (42)
<223> OTHER INFORMATION: Wherein Xaa = unclear results
<220> FEATURE:
<221> NAME/KEY: UNSURE
<222> LOCATION: (113)
<223> OTHER INFORMATION: Wherein Xaa = unclear results
<220> FEATURE:
<221> NAME/KEY: UNSURE
<222> LOCATION: (163)
<223> OTHER INFORMATION: Wherein Xaa = unclear results
<220> FEATURE:
<221> NAME/KEY: UNSURE
<222> LOCATION: (182)
<223> OTHER INFORMATION: Wherein Xaa = unclear results

```
<220> FEATURE:
<221> NAME/KEY: UNSURE
<222> LOCATION: (199)
<223> OTHER INFORMATION: Wherein Xaa = unclear results
<220> FEATURE:
<221> NAME/KEY: UNSURE
<222> LOCATION: (888)
<223> OTHER INFORMATION: Wherein Xaa = unclear results
<220> FEATURE:
<221> NAME/KEY: UNSURE
<222> LOCATION: (934)
<223> OTHER INFORMATION: Wherein Xaa = unclear results
<220> FEATURE:
<221> NAME/KEY: UNSURE
<222> LOCATION: (984)
<223> OTHER INFORMATION: Wherein Xaa = unclear results
<220> FEATURE:
<221> NAME/KEY: UNSURE
<222> LOCATION: (1067)
<223> OTHER INFORMATION: Wherein Xaa = unclear results

<400> SEQUENCE: 2
```

Gly Cys Cys Cys Tyr Cys His Phe Cys Arg Cys Arg Cys Cys Tyr Arg
 1               5                  10                  15

Phe Cys Phe Cys Ser Phe Tyr Arg Met Thr Ile Val Phe Leu Ala Xaa
            20                  25                  30

Ala Asp Thr Ser Leu Arg Cys Ser Arg Xaa Glu Ser Cys Leu Ser Leu
        35                  40                  45

Trp Ala Ile Gly Ser Leu Asn Pro Val Asn Leu Phe Ala Ala Arg Gly
50                  55                  60

Cys Leu Ser Pro Arg Pro Pro Ser Pro Cys Phe Val Leu Phe Arg Leu
65                  70                  75                  80

Leu Ser Gly Gly Arg Ser Phe Pro Gln Ser Glu Glu Leu Glu Leu Leu
                85                  90                  95

Glu Arg Arg Ile Arg Asn Tyr Lys Ser Gly Gln Glu Thr Arg Ala Gln
            100                 105                 110

Xaa Leu Gln Ser Cys Pro Trp Leu Arg Gln Gly Ser Val Ser Gly Arg
        115                 120                 125

Gly Leu Gly Gln Gly Ala Gly Gly Leu Leu Phe Pro Val Arg Ser Ser
130                 135                 140

Ser Pro Ser Ser Asp Asp Val Ala Val Ser Asp Leu Ser Leu Thr Pro
145                 150                 155                 160

Ala Leu Xaa Phe Leu Leu Ser Ala Val Thr Val Thr Pro Ser Leu Ser
                165                 170                 175

Val Cys Val Ser Gln Xaa Trp Thr Val Ile Glu Leu Arg Pro Phe Gly
            180                 185                 190

Gly Glu Leu Cys His Ser Xaa Cys Leu Asn Met Ser Glu Val Gly Thr
        195                 200                 205

Glu Thr Phe Pro Ser Pro Ser Ala Gln Leu Ser Pro Asp Ala Ser Leu
210                 215                 220

Gly Gly Leu Pro Ala Glu Asn Met Pro Gly Pro His Arg Glu Asp
225                 230                 235                 240

Ser Arg Val Pro Gly Val Ala Gly Leu Ala Ser Thr Cys Cys Val Cys
                245                 250                 255

Leu Glu Ala Glu Arg Leu Lys Gly Cys Leu Asn Ser Glu Lys Ile Cys
            260                 265                 270

Ile Ala Pro Ile Leu Ala Cys Leu Leu Ser Leu Cys Leu Cys Ile Ala
        275                 280                 285

Gly Leu Lys Trp Val Phe Val Asp Lys Ile Phe Glu Tyr Asp Ser Pro
290                 295                 300

-continued

```
Thr His Leu Asp Pro Gly Arg Ile Gly Gln Asp Pro Arg Ser Thr Val
305                 310                 315                 320

Asp Pro Thr Ala Leu Ser Ala Trp Val Pro Ser Glu Val Tyr Ala Ser
                325                 330                 335

Pro Phe Pro Ile Pro Ser Leu Glu Ser Lys Ala Glu Val Thr Val Gln
            340                 345                 350

Thr Asp Ser Ser Leu Val Pro Ser Arg Pro Phe Leu Gln Pro Ser Leu
        355                 360                 365

Tyr Asn Arg Ile Leu Asp Val Gly Leu Trp Ser Ser Ala Thr Pro Ser
370                 375                 380

Leu Ser Pro Ser Ser Leu Glu Pro Thr Thr Ala Ser Gln Ala Gln Ala
385                 390                 395                 400

Thr Glu Thr Asn Leu Gln Thr Ala Pro Lys Leu Ser Thr Ser Thr Ser
                405                 410                 415

Thr Thr Gly Thr Ser His Leu Thr Lys Cys Asp Ile Lys Gln Lys Ala
            420                 425                 430

Phe Cys Val Asn Gly Gly Glu Cys Tyr Met Val Lys Asp Leu Pro Asn
        435                 440                 445

Pro Pro Arg Tyr Leu Cys Arg Cys Pro Asn Glu Phe Thr Gly Asp Arg
450                 455                 460

Cys Gln Asn Tyr Val Met Ala Ser Phe Tyr Lys His Leu Gly Ile Glu
465                 470                 475                 480

Phe Met Glu Ala Glu Glu Leu Tyr Gln Lys Arg Val Leu Thr Ile Thr
                485                 490                 495

Gly Ile Cys Ile Ala Leu Leu Val Val Gly Ile Met Cys Val Val Ala
            500                 505                 510

Tyr Cys Lys Thr Lys Lys Gln Arg Lys Lys Leu His Asp Arg Leu Arg
        515                 520                 525

Gln Ser Leu Arg Ser Glu Arg Asn Asn Val Met Asn Met Ala Asn Gln
530                 535                 540

Pro His His Pro Asn Pro Pro Asp Asn Val Gln Leu Val Asn Gln
545                 550                 555                 560

Tyr Val Ser Lys Asn Ile Ile Ser Ser Glu Arg Val Val Glu Arg Glu
                565                 570                 575

Thr Glu Thr Ser Phe Ser Thr Ser His Tyr Thr Ser Thr Thr His His
            580                 585                 590

Ser Met Thr Val Thr Gln Thr Pro Ser His Ser Trp Ser Asn Gly His
        595                 600                 605

Thr Glu Ser Ile Leu Ser Glu Ser His Ser Val Leu Val Ser Ser Ser
610                 615                 620

Val Glu Asn Ser Arg His Thr Ser Pro Thr Gly Pro Arg Gly Arg Leu
625                 630                 635                 640

Asn Gly Ile Gly Gly Pro Arg Glu Gly Asn Ser Phe Leu Arg His Ala
                645                 650                 655

Arg Glu Thr Pro Asp Ser Tyr Arg Asp Ser Pro His Ser Glu Arg Tyr
            660                 665                 670

Val Ser Ala Met Thr Thr Pro Ala Arg Met Ser Pro Val Asp Phe His
        675                 680                 685

Thr Pro Thr Ser Pro Lys Ser Pro Ser Glu Met Ser Pro Pro Val
690                 695                 700

Ser Ser Leu Thr Ile Ser Ile Pro Ser Val Ala Val Ser Pro Phe Met
705                 710                 715                 720
```

-continued

```
Asp Glu Glu Arg Pro Leu Leu Val Thr Pro Pro Arg Leu Arg Glu
                725             730             735
Lys Tyr Asp Asn His Leu Gln Gln Phe Asn Ser Phe His Asn Asn Pro
            740                 745                 750
Thr His Glu Ser Asn Ser Leu Pro Pro Ser Pro Leu Arg Ile Val Glu
            755                 760                 765
Asp Glu Glu Tyr Glu Thr Thr Gln Gly Tyr Glu Pro Ala Gln Glu Pro
    770                 775                 780
Pro Lys Lys Leu Thr Asn Ser Arg Arg Val Lys Arg Thr Lys Pro Asn
785                 790                 795                 800
Gly His Ile Ser Ser Arg Val Glu Val Asp Ser Asp Thr Ser Ser Gln
                805                 810                 815
Ser Thr Ser Ser Glu Ser Glu Thr Glu Asp Glu Arg Ile Gly Glu Asp
            820                 825                 830
Thr Pro Phe Leu Ser Ile Gln Asn Pro Met Ala Thr Ser Leu Glu Pro
        835                 840                 845
Ala Ala Ala Tyr Arg Leu Ala Glu Asn Arg Thr Asn Pro Ala Asn Arg
    850                 855                 860
Phe Ser Thr Pro Glu Glu Leu Gln Ala Arg Leu Ser Ser Val Ile Ala
865                 870                 875                 880
Asn Gln Asp Pro Ile Ala Val Xaa Asp Ile Asn Lys Thr His Arg Phe
                885                 890                 895
Thr Cys Lys Thr Leu Phe Tyr Ile Met Lys Tyr Ser Thr Phe Lys Leu
            900                 905                 910
Asn Asn Leu Phe Tyr Phe Ser Asn Ser Ala Asp Arg Lys Gln Glu Trp
        915                 920                 925
Lys Lys Lys Leu Leu Xaa Ile Lys Tyr Thr Tyr Val Gln Met Cys Tyr
    930                 935                 940
Val Pro Tyr Val Ala Ile Phe Tyr Ser Ile Ser Lys Met Gly Lys Asp
945                 950                 955                 960
Ile Asn Gly Ala Phe Met Leu Cys Tyr Val Glu Ser Lys Phe Cys Thr
                965                 970                 975
Ala Thr Met Ile Ala Val Pro Xaa Tyr Phe Ala Lys Pro Ser Ser Pro
            980                 985                 990
Gln Leu Phe Trp Leu Phe Cys Ala Leu His Tyr Asn Asp Trp Met Tyr
        995                 1000                1005
Asp Leu Gln Glu Leu Gln Lys Ser Pro Phe Ala Cys Cys Gly Ile Pro
    1010                1015                1020
Arg Ser Lys Ser Pro Val Met Ala Leu Thr Pro Tyr Pro Leu His Gln
1025                1030                1035                1040
Glu Lys Lys Lys Ile Lys Lys Lys Lys Lys Arg Lys Glu Arg
                1045                1050                1055
Glu Lys Arg Lys Glu Lys Glu Lys Lys Ser Xaa Lys Asn Lys
            1060                1065                1070
```

<210> SEQ ID NO 3
<211> LENGTH: 1351
<212> TYPE: DNA
<213> ORGANISM: HUMAN nARIA

<400> SEQUENCE: 3

```
cggcctgtaa gatgctgtat catttggttg ggggggcctc tgcgtggtaa tggaccgtga      60
gagcggccag gccttcttct ggaggtgagc cgatggagat ttattcccca gacatgtctg     120
aggtcgccgc cgagaggtcc tccagcccct ccactcagct gagtgcagac ccatctcttg     180
```

```
atgggcttcc ggcagcagaa gacatgccag agccccagac tgaagatggg agaacccctg      240
gactcgtggg cctggccgtg ccctgctgtg cgtgcctaga agctgagcgc ctgagaggtt      300
gcctcaactc agagaaaatc tgcattgtcc ccatcctggc ttgcctggtc agcctctgcc      360
tctgcatcgc cggcctcaag tgggtatttg tggacaagat ctttgaatat gactctccta      420
ctcaccttga ccctgggggg ttaggccagg accctattat ttctctggac gcaactgctg      480
cctcagctgt gtgggtgtcg tctgaggcat acacttcacc tgtctctagg gctcaatctg      540
aaagtgaggt tcaagttaca gtgcaaggtg acaaggctgt tgtctccttt gaaccatcag      600
cggcaccgac accgaagaat cgtattttg ccttttcttt cttgccgtcc actgcgccat      660
ccttcccttc acccacccgg aaccctgagg tgagaacgcc caagtcagca actcagccac      720
aaacaacaga aactaatctc caaactgctc ctaaactttc tacatctaca tccaccactg      780
ggacaagcca tcttgtaaaa tgtgcggaga aggagaaaac tttctgtgtg aatggagggg      840
agtgcttcat ggtgaaagac ctttcaaacc cctcgagata cttgtgcaaa ggcggaggag      900
ctgtaccaga agagagtgct gaccataacc ggcatctgca tcgccctcct tgtggtcggc      960
atcatgtgtg tggtggccta ctgcaaaacc aagaaacagc ggaaaaagct gcatgaccgt     1020
cttcggcaga gccttcggtc tgaacgaaac aatacgatga acattgccaa tgggcctcac     1080
catcctaacc caccccccga gaatgtccag ctggtgaatc aatacgtatc taaaaacgtc     1140
atctccagtg agcatattgt tgagagagaa gcagagacat ccttttccac cagtcactat     1200
acttccacag cccatcactc cactactgtc acccagactc ctagccacag ctggagcaac     1260
ggacacactg aaagcatcct ttccgaaagc cactctgtaa tcgtgatgtc atccgtagaa     1320
aacagtaggc acagcagccc aactggggcc g                                    1351
```

<210> SEQ ID NO 4
<211> LENGTH: 449
<212> TYPE: PRT
<213> ORGANISM: HUMAN nARIA
<220> FEATURE:
<221> NAME/KEY: UNSURE
<222> LOCATION: (16)
<223> OTHER INFORMATION: Wherein Xaa = unclear results
<220> FEATURE:
<221> NAME/KEY: UNSURE
<222> LOCATION: (338)
<223> OTHER INFORMATION: Wherein Xaa = unclear results
<220> FEATURE:
<221> NAME/KEY: UNSURE
<222> LOCATION: (347)
<223> OTHER INFORMATION: Wherein Xaa = unclear results
<220> FEATURE:
<221> NAME/KEY: UNSURE
<222> LOCATION: (362)
<223> OTHER INFORMATION: Wherein Xaa = unclear results
<220> FEATURE:
<221> NAME/KEY: UNSURE
<222> LOCATION: (377)
<223> OTHER INFORMATION: Wherein Xaa = unclear results
<220> FEATURE:
<221> NAME/KEY: UNSURE
<222> LOCATION: (383)
<223> OTHER INFORMATION: Wherein Xaa = unclear results
<220> FEATURE:
<221> NAME/KEY: UNSURE
<222> LOCATION: (387)
<223> OTHER INFORMATION: Wherein Xaa = unclear results
<220> FEATURE:
<221> NAME/KEY: UNSURE
<222> LOCATION: (414)
<223> OTHER INFORMATION: Wherein Xaa = unclear results

```
<220> FEATURE:
<221> NAME/KEY: UNSURE
<222> LOCATION: (423)
<223> OTHER INFORMATION: Wherein Xaa = unclear results
<220> FEATURE:
<221> NAME/KEY: UNSURE
<222> LOCATION: (442)
<223> OTHER INFORMATION: Wherein Xaa = unclear results

<400> SEQUENCE: 4

Ala Cys Lys Met Leu Tyr His Leu Val Gly Ala Ser Ala Trp Xaa
1               5                   10                  15

Trp Thr Val Arg Ala Ala Arg Pro Ser Ser Gly Gly Glu Pro Met Glu
            20                  25                  30

Ile Tyr Ser Pro Asp Met Ser Glu Val Ala Ala Glu Arg Ser Ser Ser
                35                  40                  45

Pro Ser Thr Gln Leu Ser Ala Asp Pro Ser Leu Asp Gly Leu Pro Ala
            50                  55                  60

Ala Glu Asp Met Pro Glu Pro Gln Thr Glu Asp Gly Arg Thr Pro Gly
65                  70                  75                  80

Leu Val Gly Leu Ala Val Pro Cys Cys Ala Cys Leu Glu Ala Glu Arg
                85                  90                  95

Leu Arg Gly Cys Leu Asn Ser Glu Lys Ile Cys Ile Val Pro Ile Leu
                100                 105                 110

Ala Cys Leu Val Ser Leu Cys Leu Cys Ile Ala Gly Leu Lys Trp Val
                115                 120                 125

Phe Val Asp Lys Ile Phe Glu Tyr Asp Ser Pro Thr His Leu Asp Pro
130                 135                 140

Gly Gly Leu Gly Gln Asp Pro Ile Ile Ser Leu Asp Ala Thr Ala Ala
145                 150                 155                 160

Ser Ala Val Trp Val Ser Ser Glu Ala Tyr Thr Ser Pro Val Ser Arg
                165                 170                 175

Ala Gln Ser Glu Ser Glu Val Gln Val Thr Val Gln Gly Asp Lys Ala
                180                 185                 190

Val Val Ser Phe Glu Pro Ser Ala Ala Pro Thr Pro Lys Asn Arg Ile
                195                 200                 205

Phe Ala Phe Ser Phe Leu Pro Ser Thr Ala Pro Ser Phe Pro Ser Pro
210                 215                 220

Thr Arg Asn Pro Glu Val Arg Thr Pro Lys Ser Ala Thr Gln Pro Gln
225                 230                 235                 240

Thr Thr Glu Thr Asn Leu Gln Thr Ala Pro Lys Leu Ser Thr Ser Thr
                245                 250                 255

Ser Thr Thr Gly Thr Ser His Leu Val Lys Cys Ala Glu Lys Glu Lys
                260                 265                 270

Thr Phe Cys Val Asn Gly Gly Glu Cys Phe Met Val Lys Asp Leu Ser
            275                 280                 285

Asn Pro Ser Arg Tyr Leu Cys Lys Gly Gly Ala Val Pro Glu Glu
                290                 295                 300

Ser Ala Asp His Asn Arg His Leu His Arg Pro Pro Cys Gly Arg His
305                 310                 315                 320

His Val Cys Gly Gly Leu Leu Gln Asn Gln Glu Thr Ala Glu Lys Ala
                325                 330                 335

Ala Xaa Pro Ser Ser Ala Glu Pro Ser Val Xaa Thr Lys Gln Tyr Asp
        340                 345                 350

Glu His Cys Gln Trp Ala Ser Pro Ser Xaa Pro Thr Pro Arg Glu Cys
            355                 360                 365
```

-continued

```
Pro Ala Gly Glu Ser Ile Ala Ile Xaa Lys Arg His Leu Gln Xaa Ala
    370                 375                 380

Tyr Cys Xaa Glu Arg Ser Arg Asp Ile Leu Phe His Gln Ser Leu Tyr
385                 390                 395                 400

Phe His Ser Pro Ser Leu His Tyr Cys His Pro Asp Ser Xaa Pro Gln
                405                 410                 415

Leu Glu Gln Arg Thr His Xaa Lys His Pro Phe Arg Lys Pro Leu Cys
            420                 425                 430

Asn Arg Asp Val Ile Arg Arg Lys Gln Xaa Ala Gln Gln Pro Asn Trp
        435                 440                 445

Gly

<210> SEQ ID NO 5
<211> LENGTH: 7
<212> TYPE: PRT
<213> ORGANISM: HUMAN nARIA

<400> SEQUENCE: 5

Asn Gln Asp Pro Ile Ala Val
  1               5
```